(12) United States Patent
Matsumoto et al.

(10) Patent No.: US 8,871,484 B2
(45) Date of Patent: Oct. 28, 2014

(54) NITRILE HYDRATASE VARIANT

(75) Inventors: Kazuya Matsumoto, Mobara (JP);
Yasushi Kazuno, Varsity Park (SG);
Daisuke Mochizuki, Mobara (JP);
Junko Tokuda, Chiba (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 427 days.

(21) Appl. No.: 13/128,323

(22) PCT Filed: Nov. 12, 2009

(86) PCT No.: PCT/JP2009/006055
§ 371 (c)(1),
(2), (4) Date: May 9, 2011

(87) PCT Pub. No.: WO2010/055666
PCT Pub. Date: May 20, 2010

(65) Prior Publication Data
US 2011/0212506 A1 Sep. 1, 2011

(30) Foreign Application Priority Data
Nov. 14, 2008 (JP) ................................. 2008-292819

(51) Int. Cl.
*C12N 9/14* (2006.01)
*C12N 9/88* (2006.01)

(52) U.S. Cl.
CPC ....................................... *C12N 9/88* (2013.01)
USPC ...................................................... 435/195

(58) Field of Classification Search
None
See application file for complete search history.

(56) References Cited

U.S. PATENT DOCUMENTS

| | | |
|---|---|---|
| 5,807,730 A | 9/1998 | Ito et al. |
| 2007/0009985 A1 | 1/2007 | Yamaki et al. |
| 2007/0231868 A1 | 10/2007 | Watanabe et al. |

FOREIGN PATENT DOCUMENTS

| | | |
|---|---|---|
| JP | 9-275978 A | 10/1997 |
| JP | 2003-088384 | 3/2003 |
| JP | 2004-194588 A | 7/2004 |
| JP | 2005-160403 A | 6/2005 |
| JP | 2005-295815 | 10/2005 |
| JP | 2007-143409 A | 6/2007 |
| JP | 2008-253182 A | 10/2008 |
| WO | WO 2004/056990 A1 | 7/2004 |
| WO | WO 2005/116206 A1 | 12/2005 |

OTHER PUBLICATIONS

International Search Report (PCT/ISA/210) issued on Feb. 9, 2010, by Japanese Patent Office as the International Searching Authority for International Application No. PCT/JP2009/006055.

Miyanaga et al., "Mutational and structural analysis of cobalt-containing nitrile hydratase on substrate and metal binding", Eur. J. Biochem., 2004, pp. 429-438, vol. 271, No. 2.

Takarada, H. et al., "Mutational Study on αGln90 of Fe—Type Nitrile Hydratase From *Rhodococcus* Sp. N771", Bioscience Biotechnology and Biochemistry, vol. 70, No. 4, pp. 881-889 (Apr. 2006) XP002677583.

Piersma, S.R. et al., "Arginine 56 Mutation in the β Subunit of Nitrile Hydratase: Importance of Hydrogen Bonding to the Non-Heme Iron Center", Journal of Inorganic Biochemistry, vol. 80, No. 3-4, pp. 283-288 (Jul. 1, 2000) XP002677584.

Extended European Search Report dated Jul. 9, 2012, issued in corresponding European Patent Application No. 09825919.5-2404. (7 pages).

*Primary Examiner* — Sheridan Swope
(74) *Attorney, Agent, or Firm* — Buchanan, Ingersoll & Rooney PC

(57) ABSTRACT

A nitrile hydratase variant of the present invention comprises substitution of at least one amino acid with another amino acid to improve two or more properties of nitrile hydratase by substitution of one amino acid.

1 Claim, No Drawings

US 8,871,484 B2

NITRILE HYDRATASE VARIANT

TECHNICAL FIELD

The present invention relates to a nitrile hydratase variant, a gene encoding the nitrile hydratase variant, a DNA containing the gene, a plasmid containing the gene, a transformant by means of the plasmid, and a method for producing a nitrile hydratase variant using the transformant.

BACKGROUND ART

In recent years, a nitrile hydratase has been discovered which is an enzyme having the nitrile-hydrating activity to convert a nitrile group of various compounds to an amide group by hydration, and a number of microorganism strains producing the above-mentioned enzyme have been disclosed. In order to produce an amide compound from a nitrile compound using a nitrile hydratase on an industrial scale, it is important to reduce the production costs for this enzyme in the total production costs for producing the amide compound. More specifically, it is necessary to increase the activity value in a unit weight of the preparation obtained from the enzyme production.

As a method for increasing the activity value by increasing the amount of the enzyme in the enzyme preparation, attempts have already been made to clone the gene encoding the above-mentioned enzyme for the purpose of expressing a large amount of the enzyme through genetic engineering methods.

For example, there are produced a plasmid expressing a large number of the Pseudonocardia thermophila-derived nitrile hydratase in the transformant and a transformant strain transformed with the plasmid. In addition, it has been made possible to produce a nitrile hydratase by means of these transformant strains, and to produce a corresponding amide compound by bringing the transformant strain or the nitrile hydratase obtained therefrom into contact with the nitrile compound (see Patent Document 1).

On the other hand, when high activation of enzyme molecule itself can be achieved, the activity value of the enzyme preparation can be further enhanced.

Attempts have heretofore been made to search for a nitrile hydratase variant with improved substrate specificity, enzyme stability or the like by introducing mutation into a specific amino acid residue in the amino acid sequence of the nitrile hydratase without damaging its activity (see Patent Document 2 to 4).

Furthermore, a nitrile hydratase variant derived from Rhodococcus rhodochrous has been disclosed in Patent Documents 5 and 6.

RELATED DOCUMENT

Patent Document

Patent Document 1: Japanese Patent Laid-open No. H9 (1997)-275978
Patent Document 2: Japanese Patent Laid-open No. 2004-194588
Patent Document 3: Japanese Patent Laid-open No. 2005-160403
Patent Document 4: WO 2004/056990
Patent Document 5: Japanese Patent Laid-open No. 2007-143409
Patent Document 6: Japanese Patent Laid-open No. 2008-253182

DISCLOSURE OF THE INVENTION

However, as compared to a wild nitrile hydratase disclosed in Patent Document 1, specific mutants in which both of the initial reaction rate and enzyme stability are improved have not been known. It is expected that the production costs for producing the amide compound can be reduced by improving the initial reaction rate and enzyme stability at the same time.

An object of the present invention is to provide a nitrile hydratase having high initial reaction rate and enzyme stability.

That is, the present invention is specified by matters described in below.

[1] A nitrile hydratase variant comprising substitution of at least one amino acid with another amino acid to improve two or more properties of nitrile hydratase by substitution of one or more and three or less amino acids.

[2] The nitrile hydratase variant according to [1], wherein the properties to be improved are the initial reaction rate and thermal stability.

[3] The nitrile hydratase variant according to [1] or [2], comprising an α-subunit defined in SEQ ID No: 1 in the Sequence Listing and a β-subunit defined in SEQ ID No: 2 in the Sequence Listing, and substitution of at least one amino acid with another amino acid selected from substitution sites of the amino acid consisting of the following (a) to (l):
 (a) 92nd of α-subunit;
 (b) 94th of α-subunit;
 (c) 197th of α-subunit;
 (d) 4th of β-subunit;
 (e) 24th of β-subunit;
 (f) 79th of β-subunit;
 (g) 96th of β-subunit;
 (h) 107th of β-subunit;
 (i) 226th of β-subunit;
 (j) 110th of β-subunit and 231st of β-subunit;
 (k) 206th of β-subunit and 230th of β-subunit; and
 (l) 13th of α-subunit, 27th of α-subunit and 110th of β-subunit.

[4] The nitrile hydratase variant according to [3], comprising substitution of at least one amino acid with another amino acid selected from substitution sites of the amino acid consisting of the following (m) to (u):
 (m) in case of (b) or (g), 13th of α-subunit;
 (n) in case of (b) or (h), 27th of α-subunit;
 (o) (d) and (f);
 (p) in case of (f), 230th of β-subunit;
 (q) (a) and (i);
 (r) in case of (i), 13th of α-subunit and 206th of β-subunit;
 (s) in case of (a) and (d), 206th of β-subunit;
 (t) in case of (c) and (h), 230th of β-subunit; and
 (u) in case of (f), 230th of β-subunit and 231st of β-subunit.

[5] The nitrile hydratase variant according to [3], further comprising substitution of at least one amino acid with another amino acid selected from the group consisting of (a), (c), (f), (i), (h), 230th of the β-subunit and 231st of the β-subunit in case of (e) is substituted with another amino acid.

[6] The nitrile hydratase variant according to any one of [1] to [5], wherein Ile is substituted by Leu when 13th amino acid of the α-subunit is substituted,
Met is substituted by Ile when the 27th amino acid of the α-subunit is substituted,
Asp is substituted by Glu when the 92nd amino acid of the α-subunit is substituted, Met is substituted by Ile when the 94th amino acid of the α-subunit is substituted, Gly is substituted by Cys when the 197th amino acid of the α-subunit is substituted, Val is substituted by Met when the 4th amino acid of the β-subunit is substituted, Val is substituted by Ile when the 24th amino acid of the β-subunit is substituted, His is substituted by Asn when the 79th amino acid of the β-subunit is substituted, Gln is substituted by Arg when the 96th amino acid of the β-subunit is substituted, Pro is substituted by Met when the 107th amino acid of the β-subunit is substituted, Glu is substituted by Asn when the 110th amino acid of the β-subunit is substituted, Pro is substituted by Leu when the 206th amino acid of the β-subunit is substituted, Val is substituted by Ile when the 226th amino acid of the β-subunit is substituted, Ala is substituted by Glu when the 230th amino acid of the β-subunit is substituted, and Ala is substituted by Val when the 231st amino acid of the β-subunit is substituted.

[7] The nitrile hydratase variant according to any one of [3] to [6], further comprising substitution of at least one amino acid selected from substitutions of the amino acid consisting of the following (aa) to (br):

(aa) 36th Thr in the α-subunit is substituted by Met and 126th Phe in the α-subunit is substituted by Tyr;

(ab) 148th Gly in the α-subunit is substituted by Asp and 204th Val in the α-subunit is substituted by Arg;

(ac) 51st Phe in the β-subunit is substituted by Val and 108th Glu in the β-subunit is substituted by Asp;

(ad) 118th Phe in the β-subunit is substituted by Val and 200th Ala in the β-subunit is substituted by Glu;

(ae) 160th Arg in the β-subunit is substituted by Trp and 186th Leu in the β-subunit is substituted by Arg;

(af) 6th Leu in the α-subunit is substituted by Thr, 36th Thr in the α-subunit is substituted by Met, and 126th Phe in the α-subunit is substituted by Tyr;

(ag) 19th Ala in the α-subunit is substituted by Val, 71st Arg in the α-subunit is substituted by His, and 126th Phe in the α-subunit is substituted by Tyr;

(ah) 36th Thr in the α-subunit is substituted by Met, 148th Gly in the α-subunit is substituted by Asp, and 204th Val in the α-subunit is substituted by Arg;

(ai) 10th Thr in the β-subunit is substituted by Asp, 118th Phe in the β-subunit is substituted by Val, and 200th Ala in the β-subunit is substituted by Glu;

(aj) 37th Phe in the β-subunit is substituted by Leu, 108th Glu in the β-subunit is substituted by Asp, and 200th Ala in the β-subunit is substituted by Glu;

(ak) 37th Phe in the β-subunit is substituted by Val, 108th Glu in the β-subunit is substituted by Asp, and 200th Ala in the β-subunit is substituted by Glu;

(al) 41st Phe in the β-subunit is substituted by Ile, 51st Phe in the β-subunit is substituted by Val, and 108th Glu in the β-subunit is substituted by Asp;

(am) 46th Met in the β-subunit is substituted by Lys, 108th Glu in the β-subunit is substituted by Arg, and 212th Ser in the β-subunit is substituted by Tyr;

(an) 48th Leu in the β-subunit is substituted by Val, 108th Glu in the β-subunit is substituted by Arg, and 212th Ser in the β-subunit is substituted by Tyr;

(ao) 127th Leu in the β-subunit is substituted by Ser, 160th Arg in the β-subunit is substituted by Trp, and 186th Leu in the β-subunit is substituted by Arg;

(ap) 6th Leu in the α-subunit is substituted by Thr, 19th Ala in the α-subunit is substituted by Val, 126th Phe in the α-subunit is substituted by Tyr, 46th Met in the β-subunit is substituted by Lys, 108th Glu in the β-subunit is substituted by Arg, and 212th Ser in the β-subunit is substituted by Tyr;

(aq) 6th Leu in the α-subunit is substituted by Thr, 19th Ala in the α-subunit is substituted by Val, 126th Phe in the α-subunit is substituted by Tyr, 48th Leu in the β-subunit is substituted by Val, 108th Glu in the β-subunit is substituted by Arg, and 212th Ser in the β-subunit is substituted by Tyr;

(ar) 6th Leu in the α-subunit is substituted by Ala, 19th Ala in the α-subunit is substituted by Val, 126th Phe in the α-subunit is substituted by Tyr, 127th Leu in the β-subunit is substituted by Ser, 160th Arg in the β-subunit is substituted by Trp, and 186th Leu in the β-subunit is substituted by Arg;

(as) 6th Leu in the α-subunit is substituted by Thr, 36th Thr in the α-subunit is substituted by Met, 126th Phe in the α-subunit is substituted by Tyr, 10th Thr in the β-subunit is substituted by Asp, 118th Phe in the β-subunit is substituted by Val, and 200th Ala in the β-subunit is substituted by Glu;

(at) 19th Ala in the α-subunit is substituted by Val, 71st Arg in the α-subunit is substituted by His, 126th Phe in the α-subunit is substituted by Tyr, 37th Phe in the β-subunit is substituted by Leu, 108th Glu in the β-subunit is substituted by Asp, and 200th Ala in the β-subunit is substituted by Glu;

(au) 19th Ala in the α-subunit is substituted by Val, 71st Arg in the α-subunit is substituted by His, 126th Phe in the α-subunit is substituted by Tyr, 37th Phe in the β-subunit is substituted by Val, 108th Glu in the β-subunit is substituted by Asp, and 200th Ala in the β-subunit is substituted by Glu;

(av) 36th Thr in the α-subunit is substituted by Met, 148th Gly in the α-subunit is substituted by Asp, 204th Val in the α-subunit is substituted by Arg, 41st Phe in the β-subunit is substituted by Ile, 51st Phe in the β-subunit is substituted by Val, and 108th Glu in the β-subunit is substituted by Asp;

(aw) 148th Gly in the α-subunit is substituted by Asp, 204th Val in the α-subunit is substituted by Arg, 108th Glu in the β-subunit is substituted by Asp, and 200th Ala in the β-subunit is substituted by Glu;

(ax) 36th Thr in the α-subunit is substituted by Gly and 188th Thr in the α-subunit is substituted by Gly;

(ay) 36th Thr in the α-subunit is substituted by Ala and 48th Asn in the α-subunit is substituted by Gln;

(az) 48th Asn in the α-subunit is substituted by Glu and 146th Arg in the β-subunit is substituted by Gly;

(ba) 36th Thr in the α-subunit is substituted by Trp and 176th Tyr in the β-subunit is substituted by Cys;

(bb) 176th Tyr in the β-subunit is substituted by Met and 217th Asp in the β-subunit is substituted by Gly;

(bc) 36th Thr in the α-subunit is substituted by Ser, and 33rd Ala in the β-subunit is substituted by Val;

(bd) 176th Tyr in the β-subunit is substituted by Ala and 217th Asp in the β-subunit is substituted by Val;

(be) 40th Thr in the β-subunit is substituted by Val and 218th Cys in the β-subunit is substituted by Met;

(bf) 33rd Ala in the β-subunit is substituted by Met and 176th Tyr in the β-subunit is substituted by Thr;

(bg) 40th Thr in the β-subunit is substituted by Leu and 217th Asp in the β-subunit is substituted by Leu;

(bh) 40th Thr in the β-subunit is substituted by Ile and 61st Ala in the β-subunit is substituted by Val;

(bi) 61st Ala in the β-subunit is substituted by Thr and 218th Cys in the β-subunit is substituted by Ser;

(bj) 112th Lys in the β-subunit is substituted by Val and 217th Asp in the β-subunit is substituted by Met;

(bk) 61st Ala in the β-subunit is substituted by Trp and 217th Asp in the β-subunit is substituted by His;

(bl) 61st Ala in the β-subunit is substituted by Leu and 112th Lys in the β-subunit is substituted by Ile;

(bm) 146th Arg in the β-subunit is substituted by Gly and 217th Asp in the β-subunit is substituted by Ser;

(bn) 171st Lys in the β-subunit is substituted by Ala and 217th Asp in the β-subunit is substituted by Thr;

(bo) 150th Ala in the β-subunit is substituted by Ser and 217th Asp in the β-subunit is substituted by Cys;

(bp) 61st Ala in the β-subunit is substituted by Gly and 150th Ala in the β-subunit is substituted by Asn;

(bq) 61st Ala in the β-subunit is substituted by Ser and 160th Arg in the β-subunit is substituted by Met; and (br) 160th Arg in the β-subunit is substituted by Cys and 168th Thr in the β-subunit is substituted by Glu.

[8] A gene encoding the nitrile hydratase variant according to any one of [1] to [7].

[9] A gene encoding a nitrile hydratase variant having a gene encoding the α-subunit defined in SEQ ID No: 3 in the Sequence Listing and a gene encoding the β-subunit defined in SEQ ID No: 4 in the Sequence Listing, comprising substitution of at least one base selected from substitution sites of the base consisting of the following (a) to (l):

(a) 274th to 276th of the base sequence of SEQ ID No: 3;
(b) 280th to 282nd of the base sequence of SEQ ID No: 3;
(c) 589th to 591st of the base sequence of SEQ ID No: 3;
(d) 10th to 12th of the base sequence of SEQ ID No: 4;
(e) 69th to 71st of the base sequence of SEQ ID No: 4;
(f) 235th to 237th of the base sequence of SEQ ID No: 4;
(g) 286th to 288th of the base sequence of SEQ ID No: 4;
(h) 319th to 321st of the base sequence of SEQ ID No: 4;
(i) 676th to 678th of the base sequence of SEQ ID No: 4;
(j) 328th to 330th of the base sequence of SEQ ID No: 4 and 691st to 693rd of the base sequence of SEQ ID No: 4;
(k) 616th to 618th of the base sequence of SEQ ID No: 4, and 688th to 690th of the base sequence of SEQ ID No: 4; and
(l) 37th to 39th of the base sequence of SEQ ID No: 3, 79th to 81st of the base sequence of SEQ ID No: 3, and 328th to 330th of the base sequence of SEQ ID No: 4.

[10] The gene encoding a nitrile hydratase variant according to [9], further comprising substitution of at least one base selected from substitution sites of the base consisting of the following (m) to (u):

(m) in case of (b) or (g), 37th to 39th of the base sequence of SEQ ID No: 3;
(n) in case of (b) or (h), 79th to 81st of the base sequence of SEQ ID No: 3;
(o) (d) and (f);
(p) in case of (f), 688th to 690th of the base sequence of SEQ ID No: 4;
(q) (a) and (i);
(r) in case of (i), 37th to 39th of the base sequence of SEQ ID No: 3 and 616th to 618th of the base sequence of SEQ ID No: 4;
(s) in case of (a) and (d), 616th to 618th of the base sequence of SEQ ID No: 4;
(t) in case of (c) and (h), 688th to 690th of the base sequence of SEQ ID No: 4; and
(u) in case of (f), 688th to 690th of the base sequence of SEQ ID No: 4 and 691st to 693rd of the base sequence of SEQ ID No: 4.

[11] The gene encoding a nitrile hydratase variant according to [9], further comprising substitution of at least one base with another base selected from substitution sites of the base consisting of (a), (c), (f), (i), (h), 688th to 690th of the base sequence of SEQ ID No: 4, and 691st to 693rd of the base sequence of SEQ ID No: 4, in case of (e), are substituted with another base.

[12] The gene encoding a nitrile hydratase variant according to any one of [9] to [11], wherein ATC is substituted by CTC when 37th to 39th of the base sequence of SEQ ID No: 3 are substituted by another base, ATG is substituted by ATC when 79th to 81th of the base sequence of SEQ ID No: 3 are substituted by another base, GAC is substituted by GAG when 274th to 276th of the base sequence of SEQ ID No: 3 are substituted by another base, ATG is substituted by ATC when 280th to 282th of the base sequence of SEQ ID No: 3 are substituted by another base, GGC is substituted by TGC when 589th to 591th of the base sequence of SEQ ID No: 3 are substituted by another base, GTG is substituted by ATG when 10th to 12th of the base sequence of SEQ ID No: 4 are substituted by another base, GTC is substituted by ATC when 69th to 71th of the base sequence of SEQ ID No: 4 are substituted by another base, CAC is substituted by AAC when 235th to 237th of the base sequence of SEQ ID No: 4 are substituted by another base, CAG is substituted by CGT when 286th to 288th of the base sequence of SEQ ID No: 4 are substituted by another base, CCC is substituted by ATG when 319th to 321st of the base sequence of SEQ ID No: 4 are substituted by another base, GAG is substituted by AAC when 328th to 330th of the base sequence of SEQ ID No: 4 are substituted by another base, CCG is substituted by CTG when 616th to 618th of the base sequence of SEQ ID No: 4 are substituted by another base, GTC is substituted by ATC when 676th to 678th of the base sequence of SEQ ID No: 4 are substituted by another base, GCG is substituted by GAG when 688th to 690th of the base sequence of SEQ ID No: 4 are substituted by another base, and GCC is substituted by GTC when 691th to 693th of the base sequence of SEQ ID No: 4 are substituted by another base.

[13] The gene encoding a nitrile hydratase variant according to any one of [9] to [12], comprising substitution of at least one base selected from substitution sites of the base consisting of the following (aa) to (br), and having the nitrile hydratase activity:

(aa) 106th to 108th ACG of the base sequence of SEQ ID No: 3 are substituted by ATG, and 376th to 378th TTC of the base sequence of SEQ ID No: 3 are substituted by TAC;

(ab) 442nd to 444th GGC of the base sequence of SEQ ID No: 3 are substituted by GAC, and 610th to 612th GTC of the base sequence of SEQ ID No: 3 are substituted by CGC;

(ac) 151st to 153rd TTC of the base sequence of SEQ ID No: 4 are substituted by GTC, and 322nd to 324th GAG of the base sequence of SEQ ID No: 4 are substituted by GAT;

(ad) 352nd to 354th TTC of the base sequence of SEQ ID No: 4 are substituted by GTC, and 598th to 600th GCC of the base sequence of SEQ ID No: 4 are substituted by GAG;

(ae) 478th to 480th CGG of the base sequence of SEQ ID No: 4 are substituted by TGG, and 556th to 558th CTG of the base sequence of SEQ ID No: 4 are substituted by CGG;

(af) 16th to 18th CTG of the base sequence of SEQ ID No: 3 are substituted by ACG, 106th to 108th ACG of the base sequence of SEQ ID No: 3 are substituted by ATG, and 376th to 378th TTC of the base sequence of SEQ ID No: 3 are substituted by TAC;

(ag) 55th to 57th GCG of the base sequence of SEQ ID No: 3 are substituted by GTG, 211th to 213th CGT of the base sequence of SEQ ID No: 3 are substituted by CAT, and 376th to 378th TTC of the base sequence of SEQ ID No: 3 are substituted by TAC;

(ah) 106th to 108th ACG of the base sequence of SEQ ID No: 3 are substituted by ATG, 442nd to 444th GGC of the base sequence of SEQ ID No: 3 are substituted by GAC, and 610th to 612th GTC of the base sequence of SEQ ID No: 3 are substituted by CGC;

(ai) 28th to 30th ACC of the base sequence of SEQ ID No: 4 are substituted by GAC, 352nd to 354th TTC of the base sequence of SEQ ID No: 4 are substituted by GTC, and 598th to 600th GCC of the base sequence of SEQ ID No: 4 are substituted by GAG;

(aj) 109th to 111th TTC of the base sequence of SEQ ID No: 4 are substituted by CTC, 322nd to 324th GAG of the base sequence of SEQ ID No: 4 are substituted by GAT, and 598th to 600th GCC of the base sequence of SEQ ID No: 4 are substituted by GAG;

(ak) 109th to 111th TTC of the base sequence of SEQ ID No: 4 are substituted by GTC, 322nd to 324th GAG of the base sequence of SEQ ID No: 4 are substituted by GAT, and 598th to 600th GCC of the base sequence of SEQ ID No: 4 are substituted by GAG;

(al) 121st to 123rd TTC of the base sequence of SEQ ID No: 4 are substituted by ATC, 151st to 153rd TTC of the base sequence of SEQ ID No: 4 are substituted by GTC, and 322nd to 324th GAG of the base sequence of SEQ ID No: 4 are substituted by GAT;

(am) 136th to 138th ATG of the base sequence of SEQ ID No: 4 are substituted by AAG, 322nd to 324th GAG of the base sequence of SEQ ID No: 4 are substituted by CGG, and 634th to 636th TCC of the base sequence of SEQ ID No: 4 are substituted by TAC;

(an) 142nd to 144th CTG of the base sequence of SEQ ID No: 4 are substituted by GTG, 322nd to 324th GAG of the base sequence of SEQ ID No: 4 are substituted by CGG, and 634th to 636th TCC of the base sequence of SEQ ID No: 4 are substituted by TAC;

(ao) 379th to 381st CTG of the base sequence of SEQ ID No: 4 are substituted by TCG, 478th to 480th CGG of the base sequence of SEQ ID No: 4 are substituted by TGG, and 556th to 558th CTG of the base sequence of SEQ ID No: 4 are substituted by CGG;

(ap) 16th to 18th CTG of the base sequence of SEQ ID No: 3 are substituted by ACG, 55th to 57th GCG of the base sequence of SEQ ID No: 3 are substituted by GTG, 376th to 378th TTC of the base sequence of SEQ ID No: 3 are substituted by TAC, 136th to 138th ATG of the base sequence of SEQ ID No: 4 are substituted by AAG, 322nd to 324th GAG of the base sequence of SEQ ID No: 4 are substituted by CGG, and 634th to 636th TCC of the base sequence of SEQ ID No: 4 are substituted by TAC;

(aq) 16th to 18th CTG of the base sequence of SEQ ID No: 3 are substituted by ACG, 55th to 57th GCG of the base sequence of SEQ ID No: 3 are substituted by GTG, 376th to 378th TTC of the base sequence of SEQ ID No: 3 are substituted by TAC, 142nd to 144th CTG of the base sequence of SEQ ID No: 4 are substituted by GTG, 322nd to 324th GAG of the base sequence of SEQ ID No: 4 are substituted by CGG, and 634th to 636th TCC of the base sequence of SEQ ID No: 4 are substituted by TAC;

(ar) 16th to 18th CTG of the base sequence of SEQ ID No: 3 are substituted by GCG, 55th to 57th GCG of the base sequence of SEQ ID No: 3 are substituted by GTG, 376th to 378th TTC of the base sequence of SEQ ID No: 3 are substituted by TAC, 379th to 381st CTG of the base sequence of SEQ ID No: 4 are substituted by TCG, 478th to 480th CGG of the base sequence of SEQ ID No: 4 are substituted by TGG, and 556th to 558th CTG of the base sequence of SEQ ID No: 4 are substituted by CGG;

(as) 16th to 18th CTG of the base sequence of SEQ ID No: 3 are substituted by ACG, 106th to 108th ACG of the base sequence of SEQ ID No: 3 are substituted by ATG, 376th to 378th TTC of the base sequence of SEQ ID No: 3 are substituted by TAC, 28th to 30th ACC of the base sequence of SEQ ID No: 4 are substituted by GAC, 352nd to 354th TTC of the base sequence of SEQ ID No: 4 are substituted by GTC, and 598th to 600th GCC of the base sequence of SEQ ID No: 4 are substituted by GAG;

(at) 55th to 57th GCG of the base sequence of SEQ ID No: 3 are substituted by GTG, 211th to 213th CGT of the base sequence of SEQ ID No: 3 are substituted by CAT, 376th to 378th TTC of the base sequence of SEQ ID No: 3 are substituted by TAC, 109th to 111th TTC of the base sequence of SEQ ID No: 4 are substituted by CTC, 322nd to 324th GAG of the base sequence of SEQ ID No: 4 are substituted by GAT, and 598th to 600th GCC of the base sequence of SEQ ID No: 4 are substituted by GAG;

(au) 55th to 57th GCG of the base sequence of SEQ ID No: 3 are substituted by GTG, 211th to 213th CGT of the base sequence of SEQ ID No: 3 are substituted by CAT, 376th to 378th TTC of the base sequence of SEQ ID No: 3 are substituted by TAC, 109th to 111th TTC of the base sequence of SEQ ID No: 4 are substituted by GTC, 322nd to 324th GAG of the base sequence of SEQ ID No: 4 are substituted by GAT, and 598th to 600th GCC of the base sequence of SEQ ID No: 4 are substituted by GAG;

(av) 106th to 108th ACG of the base sequence of SEQ ID No: 3 are substituted by ATG, 442nd to 444th GGC of the base sequence of SEQ ID No: 3 are substituted by GAC, 610th to 612th GTC of the base sequence of SEQ ID No: 3 are substituted by CGC, 121st to 123rd TTC of the base sequence of SEQ ID No: 4 are substituted by ATC, 151st to 153rd TTC of the base sequence of SEQ ID No: 4 are substituted by GTC, and 322nd to 324th GAG of the base sequence of SEQ ID No: 4 are substituted by GAT;

(aw) 442nd to 444th GGC of the base sequence of SEQ ID No: 3 are substituted by GAC, 610th to 612th GTC of the base sequence of SEQ ID No: 3 are substituted by CGC, 322nd to 324th GAG of the base sequence of SEQ ID No: 4 are substituted by GAT, and 598th to 600th GCC of the base sequence of SEQ ID No: 4 are substituted by GAG;

(ax) 106th to 108th ACG of the base sequence of SEQ ID No: 3 are substituted by GGG, and 562nd to 564th ACC of the base sequence of SEQ ID No: 3 are substituted by GGC;

(ay) 106th to 108th ACG of the base sequence of SEQ ID No: 3 are substituted by GCG, and 142nd to 144th AAC of the base sequence of SEQ ID No: 3 are substituted by CAA;

(az) 142nd to 144th AAC of the base sequence of SEQ ID No: 3 are substituted by GAA, and 436th to 438th CGG of the base sequence of SEQ ID No: 4 are substituted by GGG;

(ba) 106th to 108th ACG of the base sequence of SEQ ID No: 3 are substituted by TGG, and 526th to 528th TAC of the base sequence of SEQ ID No: 4 are substituted by TGC;

(bb) 526th to 528th TAC of the base sequence of SEQ ID No: 4 are substituted by ATG, and 649th to 651st GAC of the base sequence of SEQ ID No: 4 are substituted by GGC;

(bc) 106th to 108th ACG of the base sequence of SEQ ID No: 3 are substituted by TCG, and 97th to 99th GCG of the base sequence of SEQ ID No: 4 are substituted by GTG;

(bd) 526th to 528th TAC of the base sequence of SEQ ID No: 4 are substituted by GCC, and 649th to 651st GAC of the base sequence of SEQ ID No: 4 are substituted by GTC;

(be) 118th to 120th ACG of the base sequence of SEQ ID No: 4 are substituted by GTG, and 652nd to 654th TGC of the base sequence of SEQ ID No: 4 are substituted by ATG;

(bf) 97th to 99th GCG of the base sequence of SEQ ID No: 4 are substituted by ATG, and 526th to 528th TAC of the base sequence of SEQ ID No: 4 are substituted by ACC;

(bg) 118th to 120th ACG of the base sequence of SEQ ID No: 4 are substituted by CTG, and 649th to 651st GAC of the base sequence of SEQ ID No: 4 are substituted by CTC;

(bh) 118th to 120th ACG of the base sequence of SEQ ID No: 4 are substituted by ATT, and 181st to 183rd GCC of the base sequence of SEQ ID No: 4 are substituted by GTC;

(bi) 181st to 183rd GCC of the base sequence of SEQ ID No: 4 are substituted by ACG, and 652nd to 654th TGC of the base sequence of SEQ ID No: 4 are substituted by TCC;

(bj) 334th to 336th AAG of the base sequence of SEQ ID No: 4 are substituted by GTG, and 649th to 651st GAC of the base sequence of SEQ ID No: 4 are substituted by ATG;

(bk) 181st to 183rd GCC of the base sequence of SEQ ID No: 4 are substituted by TGG, and 649th to 651st GAC of the base sequence of SEQ ID No: 4 are substituted by CAC;

(bl) 181st to 183rd GCC of the base sequence of SEQ ID No: 4 are substituted by CTC, and 334th to 336th AAG of the base sequence of SEQ ID No: 4 are substituted by ATT;

(bm) 436th to 438th CGG of the base sequence of SEQ ID No: 4 are substituted by GGG, and 649th to 651st GAC of the base sequence of SEQ ID No: 4 are substituted by AGC;

(bn) 511th to 513th AAG of the base sequence of SEQ ID No: 4 are substituted by GCG, and 649th to 651st GAC of the base sequence of SEQ ID No: 4 are substituted by ACC;

(bo) 448th to 450th GCG of the base sequence of SEQ ID No: 4 are substituted by TCG, and 649th to 651st GAC of the base sequence of SEQ ID No: 4 are substituted by TGT;

(bp) 181st to 183rd GCC of the base sequence of SEQ ID No: 4 are substituted by GGC, and 448th to 450th GCG of the base sequence of SEQ ID No: 4 are substituted by AAT;

(bq) 181st to 183rd GCC of the base sequence of SEQ ID No: 4 are substituted by TCG, and 478th to 480th CGG of the base sequence of SEQ ID No: 4 are substituted by ATG; and (br) 478th to 480th CGG of the base sequence of SEQ ID No: 4 are substituted by TGT, and 502nd to 504th ACG of the base sequence of SEQ ID No: 4 are substituted by GAG.

[14] A linked DNA comprising further DNA containing a promoter sequence necessary for the expression of the gene in the upstream region of the 5'-terminal of the gene encoding a nitrile hydratase variant according to any one of [9] to [13], and a ribosome binding sequence contained in SEQ ID No: 7 in the downstream region of the 3'-terminal of the promoter.

[15] A plasmid comprising the DNA according to [14].

[16] A transformant obtained by transformation of a host cell using the plasmid according to [15].

[17] A method for producing a nitrile hydratase variant, comprising cultivating the transformant according to [16] in a culture medium and producing a nitrile hydratase variant based on the nitrile hydratase gene carried by the plasmid in the transformant.

According to the present invention, a nitrile hydratase composed of an α-subunit defined in SEQ ID No: 1 in the Sequence Listing and a β-subunit defined in SEQ ID No: 2 in the Sequence Listing comprises substitution of at least one amino acid with another amino acid, selected from substitution sites of the amino acid consisting of the above (a) to (l). Thus, both of the initial reaction rate and enzyme stability of the nitrile hydratase are improved, so that the activity value in a unit weight of the enzyme preparation can be increased, and at the same time the risk of enzyme deactivation due to temperature variation or the like for the industrial use can be reduced. Accordingly, the amide compound can be stably produced with a smaller amount of the enzyme, so that the production costs for producing the amide compound can be reduced.

According to the present invention, it is possible to provide a novel nitrile hydratase variant in which the initial reaction rate and enzyme stability are improved than those of the wild nitrile hydratase, and to reduce the production costs for the enzyme in the total production costs for producing the amide compound.

DESCRIPTION OF EMBODIMENTS

The above and other objects, features and advantages will be more apparent from the following description of the preferred embodiments. The present invention will be described in more detail below.

The nitrile hydratase variant of the present invention comprises substitution of at least one amino acid with another amino acid to improve two or more properties of the nitrile hydratase by the substitution of one or more three or less amino acids.

The term "properties" to be improved in the nitrile hydratase variant of the present invention refer to properties relating to the reaction itself for hydrating a nitrile group to convert it into an amide group, and enzyme stability. The term "properties" relating to the reaction itself refer to the activity of the enzyme, the substrate specificity, Vmax, Km, and the initial reaction rate. The enzyme stability includes thermal stability, stability against the substrate, and stability against the product.

The nitrile hydratase variant of the present invention preferably comprises substitution of at least one amino acid with another amino acid to improve properties of the thermophilic bacteria-derived nitrile hydratase. As the thermophilic bacteria, suitably used are those belonging to the genus *Psuedonocardia*. A specific example includes *Psuedonocardia thermophila*.

More specifically, the nitlile hydratase variant includes at least one amino acid substituted with another amino acid, selected from substitution sites of (a) to (l) as shown in Table I, in the nitrile hydratase consisting of the α-subunit defined in SEQ ID No: 1 in the Sequence Listing and the β-subunit defined in SEQ ID No: 2 in the Sequence Listing. Thus, the nitrile hydratase variant of the present invention is provided with higher initial reaction rate and enzyme stability than the wild nitrile hydratase as described in Patent Document 1.

TABLE 1

(Table I)

|     | SEQ ID No. | No. | Before Substitution | After Substitution |
|-----|------------|-----|---------------------|--------------------|
| (a) | 1          | 92  | Asp                 | Glu                |
| (b) | 1          | 94  | Met                 | Ile                |
| (c) | 1          | 197 | Gly                 | Cys                |
| (d) | 2          | 4   | Val                 | Met                |

TABLE 1-continued (Table I)

| | SEQ ID No. | No. | Before Substitution | After Substitution |
|---|---|---|---|---|
| (e) | 2 | 24 | Val | Ile |
| (f) | 2 | 79 | His | Asn |
| (g) | 2 | 96 | Gln | Arg |
| (h) | 2 | 107 | Pro | Met |
| (i) | 2 | 226 | Val | Ile |
| (j) | 2 | 110 | Glu | Asn |
| | 2 | 231 | Ala | Val |
| (k) | 2 | 206 | Pro | Leu |
| | 2 | 230 | Ala | Glu |
| (l) | 1 | 13 | Ile | Leu |
| | 1 | 27 | Met | Ile |
| | 2 | 110 | Glu | Asn |

A plurality of substitutions of the amino acid of (a) to (l) shown in Table I may be combined, or may be combined with substitutions of the amino acid at the different sites other than (a) to (l). For example, in case of (e), at least one amino acid selected from the group consisting of (a), (c), (f), (i), (h), 230th of the β-subunit and 231st of the β-subunit may be substituted with another amino acid. Examples of substitution of the amino acid which can be combined with (a) to (l) include those in Table II.

TABLE 2

(Table II)

| | SEQ ID No. | No. | Before Substitution | After Substitution |
|---|---|---|---|---|
| (m-1) | 1 | 13 | Ile | Leu |
| | 1 | 94 | Met | Ile |
| (m-2) | 1 | 13 | Ile | Leu |
| | 2 | 96 | Gln | Arg |
| (n-1) | 1 | 27 | Met | Ile |
| | 1 | 94 | Met | Ile |
| (n-2) | 1 | 27 | Met | Ile |
| | 2 | 107 | Pro | Met |
| (o) | 2 | 4 | Val | Met |
| | 2 | 79 | His | Asn |
| (p) | 2 | 79 | His | Asn |
| | 2 | 230 | Ala | Glu |
| (q) | 1 | 92 | Asp | Glu |
| | 2 | 226 | Val | Ile |
| (r) | 1 | 13 | Ile | Leu |
| | 2 | 206 | Pro | Leu |
| | 2 | 226 | Val | Ile |
| (s) | 1 | 92 | Asp | Glu |
| | 2 | 4 | Val | Met |
| | 2 | 206 | Pro | Leu |
| (t) | 1 | 197 | Gly | Cys |
| | 2 | 107 | Pro | Met |
| | 2 | 230 | Ala | Glu |

TABLE 2-continued (Table II)

| | SEQ ID No. | No. | Before Substitution | After Substitution |
|---|---|---|---|---|
| (u) | 2 | 79 | His | Asn |
| | 2 | 230 | Ala | Glu |
| | 2 | 231 | Ala | Val |
| (v) | 1 | 92 | Asp | Glu |
| | 2 | 24 | Val | Ile |
| | 2 | 226 | Val | Ile |
| (w) | 1 | 197 | Gly | Cys |
| | 2 | 24 | Val | Ile |
| | 2 | 107 | Pro | Met |
| | 2 | 230 | Ala | Glu |
| (x) | 2 | 24 | Val | Ile |
| | 2 | 79 | His | Asn |
| | 2 | 230 | Ala | Glu |
| | 2 | 231 | Ala | Val |

The nitrile hydratase variant of the present invention may further comprise mutation in any one nitrile hydratase variant of the above (a) to (x) at sites (aa) to (br) of the amino acid of the nitrile hydratase of SEQ ID Nos: 1 and 2 as shown in Table III.

TABLE 3

(Table III)

| | SEQ ID No. | No. | Before Substitution | After Substitution |
|---|---|---|---|---|
| (aa) | 1 | 36 | Thr | Met |
| | 1 | 126 | Phe | Tyr |
| (ab) | 1 | 148 | Gly | Asp |
| | 1 | 204 | Val | Arg |
| (ac) | 2 | 51 | Phe | Val |
| | 2 | 108 | Glu | Asp |
| (ad) | 2 | 118 | Phe | Val |
| | 2 | 200 | Ala | Glu |
| (ae) | 2 | 160 | Arg | Trp |
| | 2 | 186 | Leu | Arg |
| (af) | 1 | 6 | Leu | Thr |
| | 1 | 36 | Thr | Met |
| | 1 | 126 | Phe | Tyr |
| (ag) | 1 | 19 | Ala | Val |
| | 1 | 71 | Arg | His |
| | 1 | 126 | Phe | Tyr |
| (ah) | 1 | 36 | Thr | Met |
| | 1 | 148 | Gly | Asp |
| | 1 | 204 | Val | Arg |
| (ai) | 2 | 10 | Thr | Asp |
| | 2 | 118 | Phe | Val |
| | 2 | 200 | Ala | Glu |
| (aj) | 2 | 37 | Phe | Leu |
| | 2 | 108 | Glu | Asp |
| | 2 | 200 | Ala | Glu |
| (ak) | 2 | 37 | Phe | Val |
| | 2 | 108 | Glu | Asp |
| | 2 | 200 | Ala | Glu |

TABLE 3-continued

(Table III)

| | SEQ ID No. | No. | Before Substitution | After Substitution |
|---|---|---|---|---|
| (al) | 2 | 41 | Phe | Ile |
| | 2 | 51 | Phe | Val |
| | 2 | 108 | Glu | Asp |

TABLE 4

(Table III-1)

| | | | | |
|---|---|---|---|---|
| (am) | 2 | 46 | Met | Lys |
| | 2 | 108 | Glu | Arg |
| | 2 | 212 | Ser | Tyr |
| (an) | 2 | 48 | Leu | Val |
| | 2 | 108 | Glu | Arg |
| | 2 | 212 | Ser | Tyr |
| (ao) | 2 | 127 | Leu | Ser |
| | 2 | 160 | Arg | Trp |
| | 2 | 186 | Let, | Arg |
| (ap) | 1 | 6 | Leu | Thr |
| | 1 | 19 | Ala | Val |
| | 1 | 126 | Phe | Tyr |
| | 2 | 46 | Met | Lys |
| | 2 | 108 | Glu | Arg |
| | 2 | 212 | Ser | Tyr |
| (aq) | 1 | 6 | Leu | Thr |
| | 1 | 19 | Ala | Val |
| | 1 | 126 | Phe | Tyr |
| | 2 | 48 | Leu | Val |
| | 2 | 108 | Glu | Arg |
| | 2 | 212 | Ser | Tyr |
| (ar) | 1 | 6 | Leu | Ala |
| | 1 | 19 | Ala | Val |
| | 1 | 126 | Phe | Tyr |
| | 2 | 127 | Leu | Ser |
| | 2 | 160 | Arg | Trp |
| | 2 | 186 | Leu | Arg |
| (as) | 1 | 6 | Leu | Thr |
| | 1 | 36 | Thr | Met |
| | 1 | 126 | Phe | Tyr |
| | 2 | 10 | Thr | Asp |
| | 2 | 118 | Phe | Val |
| | 2 | 200 | Ala | Glu |

TABLE 5

(Table III-2)

| | | | | |
|---|---|---|---|---|
| (at) | 1 | 19 | Ala | Val |
| | 1 | 71 | Arg | His |
| | 1 | 126 | Phe | Tyr |
| | 2 | 37 | Phe | Leu |
| | 2 | 108 | Glu | Asp |
| | 2 | 200 | Ala | Glu |
| (au) | 1 | 19 | Ala | Val |
| | 1 | 71 | Arg | His |
| | 1 | 126 | Phe | Tyr |
| | 2 | 37 | Phe | Val |
| | 2 | 108 | Glu | Asp |
| | 2 | 200 | Ala | Glu |
| (av) | 1 | 36 | Thr | Met |
| | 1 | 148 | Gly | Asp |
| | 1 | 204 | Val | Arg |

TABLE 5-continued

(Table III-2)

| | | | | |
|---|---|---|---|---|
| | 2 | 41 | Phe | Ile |
| | 2 | 51 | Phe | Val |
| | 2 | 108 | Glu | Asp |
| (aw) | 1 | 148 | Gly | Asp |
| | 1 | 204 | Val | Arg |
| | 2 | 108 | Glu | Asp |
| | 2 | 200 | Ala | Glu |
| (ax) | 1 | 36 | Thr | Gly |
| | 1 | 188 | Thr | Gly |
| (ay) | 1 | 36 | Thr | Ala |
| | 1 | 48 | Asn | Gln |
| (az) | 1 | 48 | Asn | Glu |
| | 2 | 146 | Arg | Gly |
| (ba) | 1 | 36 | Thr | Trp |
| | 2 | 176 | Tyr | Cys |
| (bb) | 2 | 176 | Tyr | Met |
| | 2 | 217 | Asp | Gly |
| (bc) | 1 | 36 | Thr | Ser |
| | 2 | 33 | Ala | Val |

TABLE 6

(Table III-3)

| | | | | |
|---|---|---|---|---|
| (bd) | 2 | 176 | Tyr | Ala |
| | 2 | 217 | Asp | Val |
| (be) | 2 | 40 | Thr | Val |
| | 2 | 218 | Cys | Met |
| (bf) | 2 | 33 | Ala | Met |
| | 2 | 176 | Tyr | Thr |
| (bg) | 2 | 40 | Thr | Leu |
| | 2 | 217 | Asp | Leu |
| (bh) | 2 | 40 | Thr | Ile |
| | 2 | 61 | Ala | Val |
| (bi) | 2 | 61 | Ala | Thr |
| | 2 | 218 | Cys | Ser |
| (bj) | 2 | 112 | Lys | Val |
| | 2 | 217 | Asp | Met |
| (bk) | 2 | 61 | Ala | Trp |
| | 2 | 217 | Asp | His |
| (bl) | 2 | 61 | Ala | Leu |
| | 2 | 112 | Lys | Ile |
| (bm) | 2 | 146 | Arg | Gly |
| | 2 | 217 | Asp | Ser |
| (bn) | 2 | 171 | Lys | Ala |
| | 2 | 217 | Asp | Thr |
| (bo) | 2 | 150 | Ala | Ser |
| | 2 | 217 | Asp | Cys |
| (bp) | 2 | 61 | Ala | Gly |
| | 2 | 150 | Ala | Asn |
| (bq) | 2 | 61 | Ala | Ser |
| | 2 | 160 | Arg | Met |

TABLE 6-continued (Table III-3)

| | | | | |
|---|---|---|---|---|
| (br) | 2 | 160 | Arg | Cys |
| | 2 | 168 | Thr | Glu |

In the present invention, the term "nitrile hydratase activity" refers to the nitrile-hydrating activity to convert a nitrile group of various compounds to an amide group by hydration, and more preferably refers to the activity to convert acrylonitrile to acrylamide.

In the present invention, the term "improved nitrile hydratase activity" refers to improvement of the initial reaction rate. The "initial reaction rate" in the present invention may be confirmed in the following manner. First, a nitrile hydratase preparation is added to a 50 mM Tris-HCl aqueous solution (pH 8.0) containing 2.5% (v/v) of acrylonitrile as a substrate. In place of the nitrile hydratase preparation, a microorganism cell, a culture or a crude purification product of the nitrile hydratase may be used. After the addition of the nitrile hydratase, the reaction is carried out at 20 degrees centigrade for 15 minutes. 1M phosphoric acid is added to the reaction solution to stop the reaction, and the produced acrylamide is quantitatively analyzed. The amount of acrylamide may be measured through HPLC analysis.

The term "improvement of the initial reaction rate" in the present invention refers to significant improvement of the initial reaction rate as compared to the wild nitrile hydratase and conventionally known nitrile hydratase variant, and specifically refers to improvement of not less than 1.2 times.

The term "improvement of enzyme stability" in the present invention refers to improvement of thermal stability of the nitrile hydratase. The nitrile hydratase with improved thermal stability is expected to increase stability against stress other than heating, i.e., stability against an organic solvent, a high-concentration substrate or a product as well, because structural stability of a protein is considered to be strengthened.

The term "thermal stability of the enzyme" in the present invention may be confirmed in the following manner. First, a nitrile hydratase preparation is heated at 60 degrees centigrade for 2 hours, and then the temperature is returned to 20 degrees centigrade, and a 50 mM Tris-HCl aqueous solution (pH 8.0) containing 2.5% (v/v) of acrylonitrile as a substrate is added thereto. In place of the nitrile hydratase preparation, a microorganism cell, a culture or a crude purification product of the nitrile hydratase may be used. The heated nitrile hydratase and substrate are mixed together, and then reacted at 20 degrees centigrade for 15 minutes to measure the initial reaction rate.

The term "improvement of thermal stability of the enzyme" in the present invention refers to significant improvement of the initial reaction rate after heating as compared to the wild nitrile hydratase and conventionally known nitrile hydratase variant heated in the same manner, and specifically refers to improvement of not less than 1.2 times.

As the wild nitrile hydratase in the present invention, preferably used is Pseudonocardia thermophila-derived nitrile hydratase as disclosed in Patent Document 1. As the plasmid expressing a large number of the wild nitrile hydratase in the transformant and a transformant strain transformed with the plasmid, there may be cited MT-10822 (deposited with the International Patent Organism Depositary at the National Institute of Advanced Industrial Science and Technology, 1-1-1 Higashi, Tsukuba-shi, Ibaraki-ken, Japan, under the deposit number FERM BP-5785, as of Feb. 7, 1996). As the conventionally known nitrile hydratase variant in the present invention, there may be cited the nitrile hydratase variant described in Patent Documents 1 to 4.

The nitrile hydratase variant of the present invention has the following properties in addition to improvement of the nitrile hydratase activity. The enzyme comprises a dimer having the α-subunit and the β-subunit which are in association as the fundamental structural unit, and the dimers are further associated to form tetramers. 111th cysteine residue of the α-subunit undergoes a post-translational modification in a cysteine sulfinic acid (Cys-SOOH), while 113th cysteine residue undergoes a post-translational modification in a cysteine sulfenic acid (Cys-SOH). A polypeptide chain of the α-subunit is bonded to a cobalt atom via the modified amino acid residue to form an active center. The reaction may be preferably carried out in the temperature range of 0 to 60 degrees centigrade, while pH during the reaction is usually selected in the range of 4 to 10 and preferably in the range of 6 to 9.

The nitrile hydratase variant of the present invention may be produced in the following manner.

First, a plasmid containing DNA encoding the nitrile hydratase variant is prepared, and a transformant or a transformant strain is obtained by transforming an arbitrary host cell using the plasmid. Subsequently, the nitrile hydratase variant is produced by cultivating the above-mentioned transformant or transformant strain.

The gene encoding a wild nitrile hydratase comprises a base sequence defined in SEQ ID No: 3 in the Sequence Listing and a base sequence defined in SEQ ID No: 4 in the Sequence Listing. The base sequence defined in SEQ ID No: 3 in the Sequence Listing corresponds to the amino acid sequence consisting of SEQ ID No: 1 in the Sequence Listing, while the base sequence defined in SEQ ID No: 4 in the Sequence Listing corresponds to the amino acid sequence consisting of SEQ ID No: 2 in the Sequence Listing. DNA encoding the nitrile hydratase variant can be obtained by performing base substitution of the base sequence defined in SEQ ID No: 3 and/or SEQ ID No: 4. Specifically, substitutions of the amino acid of (a) to (l) shown in Table I may be realized by base substitution, as shown in Table IV-1.

TABLE 7

(Table IV-1)

| | Sequence ID No. | No. | Before Substitution | After Substitution |
|---|---|---|---|---|
| (a) | 3 | 274~276 | GAC | GAA, GAG |
| (b) | 3 | 280~282 | ATG | ATT, ATC, ATA |
| (c) | 3 | 589~591 | GGC | TGT, TGC |
| (d) | 4 | 10~12 | GTG | ATG |
| (e) | 4 | 69~71 | GTC | ATT, ATC, ATA |
| (f) | 4 | 235~237 | CAC | AAT, AAC |
| (g) | 4 | 286~288 | CAG | CGT, CGC, CGA, CGG, AGA, AGG |
| (h) | 4 | 319~321 | CCC | ATG |
| (i) | 4 | 676~678 | GTC | ATT, ATC, ATA |
| (j) | 4 | 328~330 | GAG | AAT, AAC |
| | 4 | 691~693 | GCC | GTT, GTC, GTA, GTG |

TABLE 7-continued (Table IV-1)

| | Sequence ID No. | No. | Before Substitution | After Substitution |
|---|---|---|---|---|
| (k) | 4 | 616~618 | CCG | TTA, TTG, CTT, CTC, CTA, CTG |
| | 4 | 688~690 | GCG | GAA, GAG |
| (l) | 3 | 37~39 | ATC | TTA, TTG, CTT, CTC, CTA, CTG |
| | 3 | 79~81 | ATG | ATT, ATC, ATA |
| | 4 | 328~330 | GAG | AAT, AAC |

Furthermore, substitutions of the amino acid illustrated in Table II may be realized by base substitution, as shown in Table IV-2.

TABLE 8

(Table IV-2)

| | Sequence ID No. | No. | Before Substitution | After Substitution |
|---|---|---|---|---|
| (m-1) | 3 | 37~39 | ATC | TTA, TTG, CTT, CTC, CTA, CTG |
| | 3 | 280~282 | ATG | ATT, ATC, ATA |
| (m-2) | 3 | 37~39 | ATC | TTA, TTG, CTT, CTC, CTA, CTG |
| | 4 | 286~288 | CAG | CGT, CGC, CGA, CGG, AGA, AGG |
| (n-1) | 3 | 79~81 | ATG | ATT, ATC, ATA |
| | 4 | 280~282 | ATG | ATT, ATC, ATA |
| (n-2) | 3 | 79~81 | ATG | ATT, ATC, ATA |
| | 4 | 319~321 | CCC | ATG |
| (o) | 4 | 10~12 | GTG | ATG |
| | 4 | 235~237 | CAC | AAT, AAC |
| (p) | 4 | 235~237 | CAC | AAT, AAC |
| | 4 | 688~690 | GCG | GAA, GAG |
| (q) | 3 | 274~276 | GAC | GAA, GAG |
| | 4 | 676~678 | GTC | ATT, ATC, ATA |
| (r) | 3 | 37~39 | ATC | TTA, TTG, CTT, CTC, CTA, CTG |
| | 4 | 616~618 | CCG | TTA, TTG, CTT, CTC, CTA, CTG |
| | 4 | 676~678 | GTC | ATT, ATC, ATA |
| (s) | 3 | 274~276 | GAC | GAA, GAG |
| | 4 | 10~12 | GTG | ATG |
| | 4 | 616~618 | CCG | TTA, TTG, CTT, CTC, CTA, CTG |
| (t) | 3 | 589~591 | GGC | TGT, TGC |
| | 4 | 319~321 | CCC | ATG |
| | 4 | 688~690 | GCG | GAA, GAG |
| (u) | 4 | 235~237 | CAC | AAT, AAC |
| | 4 | 688~690 | GCG | GAA, GAG |
| | 4 | 691~693 | GCC | GTT, GTC, GTA, GTG |
| (v) | 3 | 274~276 | GAC | GAA, GAG |
| | 4 | 69~71 | GTC | ATT, ATC, ATA |
| | 4 | 676~678 | GTC | ATT, ATC, ATA |
| (w) | 3 | 589~591 | GGC | TGT, TGC |
| | 4 | 69~71 | GTC | ATT, ATC, ATA |
| | 4 | 319~321 | CCC | ATG |
| | 4 | 688~690 | GCG | GAA, GAG |

TABLE 8-continued (Table IV-2)

| | Sequence ID No. | No. | Before Substitution | After Substitution |
|---|---|---|---|---|
| (x) | 4 | 69~71 | GTC | ATT, ATC, ATA |
| | 4 | 235~237 | CAC | AAT, AAC |
| | 4 | 688~690 | GCG | GAA, GAG |
| | 4 | 691~693 | GCC | GTT, GTC, GTA, GTG |

Furthermore, substitutions of the amino acid illustrated in Table III may be realized by base substitution, as shown in Table V.

TABLE 9

(Table V)

| | Sequence ID No. | No. | Before Substitution | After Substitution |
|---|---|---|---|---|
| (aa) | 3 | 106~108 | ACG | ATG |
| | 3 | 376~378 | TTC | TAT, TAC |
| (ab) | 3 | 442~444 | GGC | GAU, GAC |
| | 3 | 610~612 | GTC | CGT, CGC, CGA, CGG, AGA, AGG |
| (ac) | 4 | 151~153 | TTC | GTT, GTC, GTA, GTG |
| | 4 | 322~324 | GAG | GAT, GAC |
| (ad) | 4 | 352~354 | TTC | GTT, GTC, GTA, GTG |
| | 4 | 598~600 | GCC | GAA, GAG |
| (ae) | 4 | 478~480 | CGG | TGG |
| | 4 | 556~558 | CTG | CGT, CGC, CGA, CGG, AGA, AGG |
| (af) | 3 | 16~18 | CTG | ACT, ACC, ACA, ACG |
| | 3 | 106~108 | ACG | ATG |
| | 3 | 376~378 | TTC | TAT, TAC |
| (ag) | 3 | 55~57 | GCG | GTT, GTC, GTA, GTG |
| | 3 | 211~213 | CGT | CAT, CAC |
| | 3 | 376~378 | TTC | TAT, TAC |
| (ah) | 3 | 106~108 | ACG | ATG |
| | 3 | 442~444 | GGC | GAT, GAC |
| | 3 | 610~612 | GTC | CGT, CGC, CGA, CGG, AGA, AGG |
| (ai) | 4 | 28~30 | ACC | GAT, GAC |
| | 4 | 352~354 | TTC | GTT, GTC, GTA, GTG |
| | 4 | 598~600 | GCC | GAA, GAG |
| (aj) | 4 | 109~111 | TTC | TTA, TTG, CTT, CTC, CTA, CTG |
| | 4 | 322~324 | GAG | GAT, GAC |
| | 4 | 598~600 | GCC | GAA, GAG |
| (ak) | 4 | 109~111 | TTC | GTT, GTC, GTA, GTG |
| | 4 | 322~324 | GAG | GAT, GAC |
| | 4 | 598~600 | GCC | GAA, GAG |

TABLE 10

(Table V-1)

| | | | | |
|---|---|---|---|---|
| (al) | 4 | 121~123 | TTC | ATT, ATC, ATA |
| | 4 | 151~153 | TTC | GTT, GTC, GTA, GTG |
| | 4 | 322~324 | GAG | GAT, GAC |
| (am) | 4 | 136~138 | ATG | AAA, AAG |
| | 4 | 322~324 | GAG | CGT, CGC, CGA, CGG, AGA, AGG |
| | 4 | 634~636 | TCC | TAT, TAC |
| (an) | 4 | 142~144 | CTG | GTT, GTC, GTA, GTG |
| | 4 | 322~324 | GAG | CGT, CGC, CGA, CGG, AGA, AGG |
| | 4 | 634~636 | TCC | TAT, TAC |
| (ao) | 4 | 379~381 | CTG | TCT, TCC, TCA, TCG, AGT, AGC |
| | 4 | 478~480 | CGG | TGG |
| | 4 | 556~558 | CTG | CGT, CGC, CGA, CGG, AGA, AGG |
| (ap) | 3 | 16~18 | CTG | ACT, ACC, ACA, ACG |
| | 3 | 55~57 | GCG | GTT, GTC, GTA, GTG |
| | 3 | 376~378 | TTC | TAT, TAC |
| | 4 | 136~138 | ATG | AAA, AAG |
| | 4 | 322~324 | GAG | CGT, CGC, CGA, CGG, AGA, AGG |
| | 4 | 634~636 | TCC | TAT, TAC |
| (aq) | 3 | 16~18 | CTG | ACT, ACC, ACA, ACG |
| | 3 | 55~57 | GCG | GTT, GTC, GTA, GTG |
| | 3 | 376~378 | TTC | TAT, TAC |
| | 4 | 142~144 | CTG | GTT, GTC, GTA, GTG |
| | 4 | 322~324 | GAG | CGT, CGC, CGA, CGG, AGA, AGG |
| | 4 | 634~636 | TCC | TAT, TAC |
| (ar) | 3 | 16~18 | CTG | GCT, GCC, GCA, GCG |
| | 3 | 55~57 | GCG | GTT, GTC, GTA, GTG |
| | 3 | 376~378 | TTC | TAT, TAC |
| | 4 | 379~381 | CTG | TCT, TCC, TCA, TCG, AGU, AGC |
| | 4 | 478~480 | CGG | TGG |
| | 4 | 556~558 | CTG | CGT, CGC, CGA, CGG, AGA, AGG |

TABLE 11

(Table V-2)

| | | | | |
|---|---|---|---|---|
| (as) | 3 | 16~18 | CTG | ACT, ACC, ACA, ACG |
| | 3 | 106~108 | ACG | ATG |
| | 3 | 376~378 | TTC | TAT, TAC |
| | 4 | 28~30 | ACC | GAT, GAC |
| | 4 | 352~354 | TTC | GTT, GTC, GTA, GTG |
| | 4 | 598~600 | GCC | GAA, GAG |
| (at) | 3 | 55~57 | GCG | GTT, GTC, GTA, GTG |
| | 3 | 211~213 | CGT | CAT, CAC |
| | 3 | 376~378 | TTC | TAT, TAC |
| | 4 | 109~111 | TTC | TTA, TTG, CTT, CTC, CTA, CTG |
| | 4 | 322~324 | GAG | GAT, GAC |
| | 4 | 598~600 | GCC | GAA, GAG |
| (au) | 3 | 55~57 | GCG | GTT, GTC, GTA, GTG |
| | 3 | 211~213 | CGT | CAT, CAC |
| | 3 | 376~378 | TTC | TAT, TAC |
| | 4 | 109~111 | TTC | GTT, GTC, GTA, GTG |
| | 4 | 322~324 | GAG | GAT, GAC |
| | 4 | 598~600 | GCC | GAA, GAG |
| (av) | 3 | 106~108 | ACG | ATG |
| | 3 | 442~444 | GGC | GAT, GAC |
| | 3 | 610~612 | GTC | CGT, CGC, CGA, CGG, AGA, AGG |

TABLE 11-continued (Table V-2)

| | | | | |
|---|---|---|---|---|
| | 4 | 121~123 | TTC | ATT, ATC, ATA |
| | 4 | 151~153 | TTC | GTT, GTC, GTA, GTG |
| | 4 | 322~324 | GAG | GAT, GAC |
| (aw) | 3 | 442~444 | GGC | GAT, GAC |
| | 3 | 610~612 | GTC | CGT, CGC, CGA, CGG, AGA, AGG |
| | 4 | 322~324 | GAG | GAT, GAC |
| | 4 | 598~600 | GCC | GAA, GAG |
| (ax) | 3 | 106~108 | ACG | GGT, GGC, GGA, GGG |
| | 3 | 562~564 | ACC | GGT, GGC, GGA, GGG |

TABLE 12

(Table V-3)

| | | | | |
|---|---|---|---|---|
| (ay) | 3 | 106~108 | ACG | GCT, GCC, GCA, GCG |
| | 3 | 142~144 | AAC | CAA, CAG |
| (az) | 3 | 142~144 | AAC | GAA, GAG |
| | 4 | 436~438 | CGG | GGT, GGC, GGA, GGG |
| (ba) | 3 | 106~108 | ACG | TGG |
| | 4 | 526~528 | TAC | TGT, TGC |
| (bb) | 4 | 526~528 | TAC | ATG |
| | 4 | 649~651 | GAC | GGT, GGC, GGA, GGG |
| (bc) | 3 | 106~108 | ACG | TCT, TCC, TCA, TCG, AGT, AGC |
| | 4 | 97~99 | GCG | GTT, GTC, GTA, GTG |
| (bd) | 4 | 526~528 | TAC | GCT, GCC, GCA, GCG |
| | 4 | 649~651 | GAC | GTT, GTC, GTA, GTG |
| (be) | 4 | 118~120 | ACG | GTT, GTC, GTA, GTG |
| | 4 | 652~654 | TGC | ATG |
| (bf) | 4 | 97~99 | GCG | ATG |
| | 4 | 526~528 | TAC | ACT, ACC, ACA, ACG |
| (bg) | 4 | 118~120 | ACG | TTA, TTG, CTT, CTC, CTA, CTG |
| | 4 | 649~651 | GAC | TTA, TTG, CTT, CTC, CTA, CTG |
| (bh) | 4 | 118~120 | ACG | ATT, ATC, ATA |
| | 4 | 181~183 | GCC | GTT, GTC, GTA, GTG |
| (bi) | 4 | 181~183 | GCC | ACT, ACC, ACA, ACG |
| | 4 | 652~654 | TGC | TCT, TCC, TCA, TCG, AGT, AGC |
| (bj) | 4 | 334~336 | AAG | GTT, GTC, GTA, GTG |
| | 4 | 649~651 | GAC | ATG |
| (bk) | 4 | 181~183 | GCC | TGG |
| | 4 | 649~651 | GAC | CAT, CAC |
| (bl) | 4 | 181~183 | GCC | TTA, TTG, CTT, CTC, CTA, CTG |
| | 4 | 334~336 | AAG | ATT, ATC, ATA |

TABLE 13

(Table V-4)

| | | | | |
|---|---|---|---|---|
| (bm) | 4 | 436~438 | CGG | GGT, GGC, GGA, GGG |
| | 4 | 649~651 | GAC | TCT, TCC, TCA, TCG, AGT, AGC |
| (bn) | 4 | 511~513 | AAG | GCT, GCC, GCA, GCG |
| | 4 | 649~651 | GAC | ACT, ACC, ACA, ACG |

TABLE 13-continued (Table V-4)

| | | | | | | | | | |
|---|---|---|---|---|---|---|---|---|---|
| (bo) | 4 | 448~450 | GCG | TCT, | TCC, | TCA, | TCG, | AGT, | AGC |
| | 4 | 649~651 | GAC | | | TGT, | TGC | | |
| (bp) | 4 | 181~183 | GCC | | GGT, | GGC, | GGA, | GGG | |
| | 4 | 448~450 | GCG | | | AAT, | AAC | | |
| (bq) | 4 | 181~183 | GCC | TCT, | TCC, | TCA, | TCG, | AGT, | AGC |
| | 4 | 478~480 | CGG | | | ATG | | | |
| (br) | 4 | 478~480 | CGG | | | TGT, | TGC | | |
| | 4 | 502~504 | ACG | | | GAA, | GAG | | |

The plasmid can have, in addition to a gene encoding the α-subunit of the nitrile hydratase variant, a gene encoding the β-subunit or a nitrile hydratase variant gene or nitryl hydratase variant gene, a constitution which enables the production of a nitrile hydratase by a transformant or a transformant strain obtained by transforming an arbitrary host cell, such as the regulatory region necessary for the expression of each gene, the region necessary for autonomous replication or the like. The arbitrary host cell as used herein may be exemplified by *Escherichia coli*.

The regulatory region necessary for expression may include a promoter sequence (including the transcription-regulating operator sequence), a ribosome binding sequence (SD sequence), a transcription-terminating sequence and the like. Specific examples of the promoter sequence may include a trp promoter of tryptophan operon and a lac promoter of lactose operon that are derived from *Escherichia coli*, and a PL promoter and a PR promoter that are derived from lambda phage. Further, artificially designed or improved sequences such as a tac promoter or a trc promoter may also be used.

The ribosome binding sequence is preferably a sequence having TAAGGAGGT contained in SEQ ID No: 7. The sequence order of these regulatory regions on a plasmid is preferably such that the promoter sequence and the ribosome binding sequence are located upstream to the 5'-terminal than the gene encoding the nitrile hydratase variant, and the transcription-terminating sequence is preferably located downstream to the 3'-terminal than the gene encoding the nitrile hydratase variant. Also, the α-subunit gene and the β-subunit gene of the nitrile hydratase variant may be expressed as individual independent cistrons by means of such regulatory regions, or may be expressed as a polycistron by means of a common regulatory region.

Examples of the plasmid vector satisfying the above requirements may include pBR322, pUC18, pBluescript, pKK223-3 and pSC101, which have a region capable of autonomous replication in *Escherichia coli*.

For a method of constructing the plasmid of the present invention by inserting the gene encoding the nitrile hydratase variant of the present invention into such a plasmid vector, together with those regions necessary for expression of the activity of the nitrile hydratase variant, a method of transforming the plasmid to a desired host cell and a method of producing nitrile hydratase in the transformant, there may be used those general methods and host cells known in the art of molecular biology, biological engineering and genetic engineering as described in, for example, "Molecular Cloning, 3rd Edition" (J. Sambrook et al., Cold Spring Harbor Laboratory Press, 2001) or the like.

The transformant obtained by transforming the above plasmid to a desired host cell is cultivated in a culture medium, whereby the nitrile hydratase variant can be produced based on the nitrile hydratase gene carried by the plasmid. When the host cell is *Escherichia coli*, LB medium, M9 medium or the like is generally used as the culture medium for cultivating the transformant. More preferably, these medium components may comprise Fe ions and Co ions in an amount of 0.1 μg/mL or more, or the transformant may be inoculated and then cultivated at a suitable cultivating temperature (in general, from 20 to 50 degrees centigrade).

When the nitrile hydratase variant having the desired enzyme activity to express the gene encoding the nitrile hydratase variant of the present invention is produced, a gene encoding a protein involved in the activation of nitrile hydratase may be required in some cases.

A protein involved in the activation of nitrile hydratase is a protein having the property such that the presence or absence of the expression of the protein directly controls the activation of nitrile hydratase, and it can be exemplified by the protein involved in the activation of Pseudonocardia thermophila-derived nitrile hydratase (nitrile hydratase-activating protein) as described in Japanese Patent Laid-open No. H11 (1999)-253168. The sequence of the nitrile hydratase-activating protein is presented in the Sequence Listing: 5 and 6.

The amide compound can be produced in the following manner using the nitrile hydratase variant of the present invention. First, the transformant or transformant strain to produce the nitrile hydratase variant of the present invention is caltivated, and a given cell or a given product obtained by processing the cells is brought into contact with a nitrile compound in a solvent. In this manner, a corresponding amide compound is produced.

The term "product obtained by processing the cells" mentioned herein refers to an extract or a disruption product of the transformant, a post-separation product such as a crude enzyme preparation obtained by isolating the nitrile hydratase activated fraction from such extract or disruption product, an enzyme purification product obtained by further purification or the like, and an immobilization product in which the transformant, or an extract, a disruption product or a post-separation product of the transformant is immobilized by using suitable means. The contact temperature is not particularly limited, but it is preferably in the range of not deactivating the nitrile hydratase variant, and more preferably from 0 to 60 degrees centigrade. As the nitrile compound, there is no particular limitation as long as it is a compound which can act as the substrate for the nitrile hydratase variant of the present invention, and it can be preferably exemplified by nitrile compounds having 2 to 4 carbon atoms, such as acetonitrile, propionitrile, acrylonitrile, methacrylonitrile, n-butyronitrile, isobutyronitrile, crotononitrile, α-hydroxy-isobutyronitrile and the like. The concentration of the nitrile compound in the aqueous medium is not particularly limited. The reaction temperature is not particularly limited, but it is preferably in the range of not deactivating the nitrile hydratase, and more preferably from 0 to 60 degrees centigrade. Furthermore, in order to produce an amide compound with a smaller amount of the enzyme, it is preferable to use a nitrile hydratase variant having a certain level of stability under conditions of producing an amide compound.

Subsequently, the operational effect of the present invention will be described in detail. The present inventors have repeatedly conducted an extensive study and as a result, have found a nitrile hydratase variant in which both physical properties relating to the reaction itself and the enzyme stability are improved as compared to the conventional nitrile hydratase, comprising substitution of at least one amino acid with another amino acid to improve two or more properties of nitrile hydratase by substitution of one or more and three or less amino acids. In particular, they have found that with respect to the nitrile hydratase comprising the α-subunit defined in SEQ ID No: 1 in the Sequence Listing and the β-subunit defined in SEQ ID No: 2 in the Sequence Listing, at least one amino acid is substituted with another amino acid, selected from substitution sites of the amino acid consisting of the above (a) to (l), whereby enzyme stability as well as the initial reaction rate of the nitrile hydratase can be improved at the same time. In this way, both of efficiency of the enzymatic reaction and handling of the enzyme can be achieved. Also, by use of the nitrile hydratase in which both of the initial reaction rate and enzyme stability are enhanced, the activity value in a unit weight of the enzyme preparation can be increased, and at the same time the risk of enzyme deactivation due to temperature variation or the like for the industrial use can be reduced. Accordingly, the amide compound can be stably produced with a smaller amount of the enzyme so that the production costs for producing the amide compound can be reduced.

As described above, embodiments of the present invention has been described, but the embodiments described in the present invention are illustrative only, and various other constructions may also be adopted.

EXAMPLES

The present invention is now illustrated in detail below with reference to the following Examples. However, the present invention is not restricted to these Examples.

Example 1

Construction of Plasmid (1) Expressing Nitrile Hydratase with Modified Ribosome Binding Sequence A gene fragment of about 0.7 kbp was obtained by the PCR reaction using a plasmid pPT-DB1 described in Example 3 of Patent Document 1 as the template and the primers defined in SEQ ID Nos: 7 and 8 in the Sequence Listing. The above-mentioned PCR fragment was cleaved by means of restriction endonucleases EcoRI and NotI, and then this mixture treated with restriction endonucleases was subjected to phenol/chloroform extraction and ethanol precipitation to purify the DNA fragment. In the same manner, pPT-DB1 was cleaved by means of EcoRI and NotI, and then subjected to agarose gel electrophoresis, through which only the DNA fragment of about 3.9 kbp was cut out of the agarose gel. The thus obtained DNA fragments of about 0.7 kbp and of about 3.9 kbp were subjected to DNA ligation using a DNA ligation kit (manufactured by Takara Shuzo Co., Ltd.) to prepare a plasmid (1) expressing the above-mentioned nitrile hydratase with the modified ribosome binding sequence.

A competent cell of *Escherichia coli* HB101 (manufactured by Toyobo Co., Ltd.) was transformed with the plasmid to obtain a transformant (1). Moreover, the plasmid was prepared from the above microbial cells by the alkaline SDS extraction method, and the base sequence of the nitrile hydratase gene was determined using a DNA sequencer. Then, it was confirmed that the transformant (1) had the modified ribosome binding sequence in pPT-DB1 as shown in Table 1.

In the production of an amide compound using the thus obtained transformant (1) and a transformant MT-10822 containing pPT-DB1 (deposited with the International Patent Organism Depositary at the National Institute of Advanced Industrial Science and Technology, 1-1-1 Higashi, Tsukuba-shi, Ibaraki-ken, Japan, under the deposit number FERM BP-5785 from Feb. 7, 1996) to be its base, the initial reaction rates were compared in the following method.

Comparison of Initial Reaction Rate 5 mL of a liquid LB medium containing 40 μg/mL of ferric sulfate heptahydrate and 10 μg/mL of cobalt chloride dihydrate was prepared in a test tube, and sterilized by autoclaving at 121 degrees centigrade for 20 minutes. Ampicillin was added to this medium to have a final concentration of 100 μg/mL. Then, on the medium, one platinum loop of respective transformants was inoculated and cultivated therein at 37 degrees centigrade for about 20 hours with stirring at 200 rpm. 40 μL of the resulting culture was taken and suspended in 740 μL of a 54 mM Tris-HCl aqueous solution (pH 8.0). To this, 20 μL of acrylonitrile was added, and this mixture was gently stirred at 20 degrees centigrade for 15 minutes to react, whereby acrylamide was produced. After completion of the reaction, the content of acrylamide in the reaction solution was analyzed through HPLC.

Comparison of Thermal Stability of Enzyme

Respective transformants were separated from the resulting culture of the above-mentioned transformants by centrifugation (5,000 G×15 minutes).

0.1 g of the thus isolated transformants were respectively suspended in 20 ml of a 50 mM Tris-HCl aqueous solution (pH 8.0), and heated at 60 degrees centigrade for 2 hours. The temperature was returned to 20 degrees centigrade after heating, and 0.5 ml of acrylonitrile was added thereto as the substrate. The reaction was carried out at 20 degrees centigrade for 15 minutes to measure the initial reaction rate.

Analytical Conditions

Analytical Equipment: HPLC manufactured by JASCO Corporation

Column: YMC Pack ODS-A (150×6.00 mm)

Analytical Temperature: 40 degrees centigrade

Mobile Phase: 3% acetonitrile, 10 mM phosphoric acid

Respective transformants were subjected to the reaction and analysis three times or more to correct variations in the data by means of a dispensing operation or the like.

As a result of comparison of the initial reaction rate and thermal stability of the transformant (1) and MT-10822, that is, the amount of produced acrylamide under the above reaction conditions, improvement of the initial reaction rate by 1.15 times was observed and thermal stability was maintained with the new addition of the modified ribosome binding sequence shown in Table 1.

TABLE 14

(Table 1)

| Transformant No. | Mutated Site | Change in Base Sequence | | Effect on Improvement of Reaction Rate by Ribosome Binding Sequence Substitution | Effect on Improvement of Thermal Stability by Ribosome Binding Sequence Substitution |
|---|---|---|---|---|---|
| | | Before Substitution | After Substitution | | |
| 1 | Ribosome Binding Sequence | TGAGAGGAG | TAAGGAGGT | 1.15 times | 1.00 time |

Reference Example 1

Construction of a Transformant (2) Substituted Amino Acid Having Nitrile Hydratase Activity In order to obtain a transformant (2) expressing the nitrile hydratase variant obtained by mutating nitrile hydratase at (av) amino acid substitution sites as shown in Table 2, the plasmid described in Example 79 of Patent Document 2 was used as the template, and the ribosome binding sequence was modified in the method described in Example 1 to prepare a plasmid (2) encoding the above-mentioned nitrile hydratase variant. A competent cell of *Escherichia coli* HB101 (manufactured by Toyobo Co., Ltd.) was transformed with the plasmid to obtain a transformant (2).

Reference Example 2

Construction of a Transformant (3) Substituted Amino Acid Having Nitrile Hydratase Activity In order to obtain a transformant (3) expressing the nitrile hydratase variant obtained by mutating nitrile hydratase at (bc) amino acid substitution sites as shown in Table 2, introduction of site-specific mutation was performed using a "LA PCR in vitro mutagenesis Kit" manufactured by Takara Shuzo Co., Ltd. (hereinafter referred to as the mutagenesis kit). The plasmid (1) expressing nitrile hydratase with the modified ribosome binding sequence described in Example 1 was used as the template to carry out the PCR reaction.

For the PCR reaction No. 1, a reaction system of 50 µL in total containing 50 pmols of the primer having the sequence defined in SEQ ID No: 9 in the Sequence Listing and 50 pmols of an M13 primer M4 (having the sequence defined in SEQ ID No: 10 in the Sequence Listing) (for the composition of the system, the instructions described in the mutagenesis kit were followed) was used, and the reaction consisted of 25 PCR cycles, in which one PCR cycle comprised thermal denaturation (98 degrees centigrade) for 15 seconds, annealing (55 degrees centigrade) for 30 seconds and chain extension (72 degrees centigrade) for 120 seconds.

For the PCR reaction No. 2, a reaction system of 50 µL in total containing 50 pmols of an MUT4 primer (having the sequence defined in SEQ ID No: 11 in the Sequence Listing) and an M13 primer RV (having the sequence defined in SEQ ID No: 12 in the Sequence Listing) (for the composition of the system, the instructions described in the mutagenesis kit were followed) was used, and the reaction was carried out following the same procedure as the PCR reaction No. 1.

After completion of the PCR reaction Nos. 1 and 2, 5 µL of the reaction mixture was subjected to agarose gel electrophoresis (where the agarose concentration was 1.0 weight %), and an analysis of the DNA amplification product was carried out. As a result, the presence of the amplified DNA product was confirmed. From each of these PCR reaction mixtures, the excess primers and dNTP were removed using Microcon 100 (manufactured by Takara Shuzo Co., Ltd.), and then TE was added to each of the mixtures to prepare 50 µL each of TE solutions. An annealing solution of 47.5 µL in total containing 0.5 µL of both of the above TE solutions (for the composition of the system, the instructions described in the mutagenesis kit were followed) was prepared, and this solution was subjected to annealing by performing thermal denaturation of the solution at 98 degrees centigrade for 10 minutes, subsequently cooling the solution to 37 degrees centigrade at a constant cooling rate over a period of 60 minutes, and then maintaining it at 37 degrees centigrade for 15 minutes. To the thus annealed solution, 0.5 µL of TaKaRa LA Taq (manufactured by Takara Bio Inc.) was added, and the solution was heated at 72 degrees centigrade for 3 minutes, thus completing the formation of heterologous double-stranded DNA.

To this was added 50 pmols of an M13 primer M4 (having the sequence defined in SEQ ID No: 10 in the Sequence Listing) and 50 pmols of an M13 primer RV (having the sequence defined in SEQ ID No: 12 in the Sequence Listing) to give a reaction system of 50 µL in total, and the reaction consisted of 25 PCR cycles, in which one PCR cycle comprised thermal denaturation (98 degrees centigrade) for 15 seconds, annealing (55 degrees centigrade) for 30 seconds and chain extension (72 degrees centigrade) for 120 seconds to carry out the PCR reaction No. 3. After completion of the PCR reaction No. 3, 5 µL of the reaction mixture was subjected to agarose gel electrophoresis (using Type VII low-melting-point agarose, a product by Sigma Corporation; agarose concentration of 0.8 weight %), and an analysis of the DNA amplification product was carried out. As a result, the presence of the amplified DNA product of about 2 kb was confirmed.

Subsequently, an agarose fragment comprising only the DNA fragment of about 2 kb was cut out of the agarose gel. The thus cut agarose fragment (about 0.1 g) was finely pulverized, suspended in 1 ml of a TE solution, and then kept at 55 degrees centigrade for 1 hour, whereby the agarose fragment was completely melted. The resulting agarose melt was then subjected to phenol/chloroform extraction and ethanol precipitation to purify the DNA fragment. The thus purified DNA fragment was finally dissolved in 10 µL of TE. The amplified DNA fragment of about 2 kb thus purified was cleaved by means of restriction endonucleases EcoRI and HindIII, and this mixture treated with restriction endonucleases was then subjected to phenol/chloroform extraction and ethanol precipitation to purify the DNA fragment. The thus purified DNA fragment was finally dissolved in 10 µL of TE.

Likewise, the plasmid (1) expressing nitrile hydratase with the modified ribosome binding sequence described in Example 1 was cleaved by means of EcoRI and HindIII, and then subjected to agarose gel electrophoresis (using Type VII low-melting-point agarose, a product by Sigma Corporation; agarose concentration of 0.7%). An agarose fragment comprising only the DNA fragment of about 2.7 kb was cut out of the agarose gel. The thus cut agarose fragment (about 0.1 g) was finely pulverized, suspended in 1 ml of the TE solution, and then kept at 55 degrees centigrade for 1 hour, whereby the agarose fragment was completely melted. The resulting agarose melt was then subjected to phenol/chloroform extraction and ethanol precipitation to purify the DNA fragment. The thus purified DNA fragment was finally dissolved in 10 μL of TE.

The thus obtained DNA fragments of about 2 kbp and of about 2.7 kbp were subjected to DNA ligation, using a DNA ligation kit (manufactured by Takara Shuzo Co., Ltd.). Then, a competent cell of *Escherichia coli* HB101 (manufactured by Toyobo Co., Ltd.) was transformed. The above operation was carried out using the plasmid extracted from the transformant as the template, and using the primer having the sequence defined in SEQ ID No: 13 instead of the primer defined in SEQ ID No: 9, whereby a plasmid (3) encoding the above nitrile hydratase variant was prepared. A competent cell of *Escherichia coli* HB101 (manufactured by Toyobo Co., Ltd.) was transformed with the plasmid to obtain a transformant (3).

Reference Example 3

Construction of a Transformant (4) Substituted Amino Acid Having Nitrile Hydratase Activity In order to obtain a transformant (4) expressing the nitrile hydratase variant obtained by mutating nitrile hydratase at (bh) amino acid substitution sites as shown in Table 2, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 14 and 15 in the Sequence Listing were used for repeatedly carrying out the method described in Reference Example 2 per mutation point, whereby a plasmid (4) encoding the above nitrile hydratase variant was prepared. A competent cell of *Escherichia coli* HB101 (manufactured by Toyobo Co., Ltd.) was transformed with the plasmid to obtain a transformant (4).

TABLE 15

(Table 2)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 2 | α-36th | Thr | Met | ACG | ATG |
| | α-148th | Gly | Asp | GGC | GAC |
| | α-204th | Val | Arg | GTC | CGC |
| | β-41st | Phe | Ile | TTC | ATC |
| | β-51st | Phe | Val | TTC | GTC |
| | β-108th | Glu | Asp | GAG | GAT |
| 3 | α-36th | Thr | Ser | ACG | TCG |
| | β-33rd | Ala | Val | GCG | GTG |
| 4 | β-40th | Thr | Ile | ACG | ATT |
| | β-61st | Ala | Val | GCC | GTC |

Example 2

Construction of a Transformant (5) Substituted Amino Acid Having Improved Nitrile Hydratase Activity and Improved Thermal Stability In order to obtain a transformant (5) expressing the nitrile hydratase variant obtained by mutating nitrile hydratase at (a) and (av) amino acid substitution sites as shown in Table 3, the plasmid (2) recovered from the transformant (2) described in the above Reference Example 1 was used as the template, and the primer having the sequence defined in SEQ ID No: 16 in the Sequence Listing was used for carrying out the method using the mutagenesis kit described in Reference Example 2, whereby a plasmid (5) encoding the above nitrile hydratase variant was prepared. A competent cell of *Escherichia coli* HB101 (manufactured by Toyobo Co., Ltd.) was transformed with the plasmid to obtain a transformant (5). Moreover, the plasmid was prepared from the above-mentioned microbial cells by the alkaline SDS extraction method, and the base sequence of the nitrile hydratase gene was determined using a DNA sequencer. Then, it was confirmed that the transformant (5) had sequences according to the purpose in which mutation of 92nd Asp in the α-subunit with Glu was newly added to the plasmid (2) of Reference Example 1.

In the production of an amide compound using the thus obtained transformant (5) and the transformant (2) to be its base, the initial reaction rate and thermal stability were compared in the same manner as in Example 1.

As a result, it was found that mutation of 92nd Asp in the α-subunit with Glu was newly added to the transformant (5), so that the initial reaction rate was improved by 1.65 times and thermal stability was improved by 1.25 times, as compared to those of the transformant (2).

Example 3

Construction of a Transformant (6) Substituted Amino Acid Having Improved Nitrile Hydratase Activity and Improved Thermal Stability In order to obtain a transformant (6) expressing the nitrile hydratase variant obtained by mutating nitrile hydratase at (a) and (bc) amino acid substitution sites as shown in Table 3, the plasmid (3) recovered from the transformant (3) described in the above Reference Example 2 was used as the template, and the primer having the sequence defined in SEQ ID No: 16 in the Sequence Listing was used for carrying out the method using the mutagenesis kit described in Reference Example 2, whereby a plasmid (6) encoding the above nitrile hydratase variant was prepared. A competent cell of *Escherichia coli* HB101 (manufactured by Toyobo Co., Ltd.) was transformed with the plasmid to obtain a transformant (6). Moreover, the plasmid was prepared from the above-mentioned microbial cells by the alkaline SDS extraction method, and the base sequence of the nitrile hydratase gene was determined using a DNA sequencer. Then, it was confirmed that the transformant (6) had sequences according to the purpose in which mutation of 92nd Asp in the α-subunit with Glu was newly added to the plasmid (3) of Reference Example 2. In the production of an amide compound using the thus obtained transformant (6) and the transformant (3) to be its base, the initial reaction rate and thermal stability were compared in the same manner as in Example 1.

As a result, it was found that mutation of 92nd Asp in the α-subunit with Glu was newly added to the transformant (6), so that the initial reaction rate was improved by 1.63 times and thermal stability was improved by 1.23 times, as compared to those of the transformant (3).

Example 4

Construction of a Transformant (7) Substituted Amino Acid Having Improved Nitrile Hydratase Activity and Improved Thermal Stability In order to obtain a transformant (7) expressing the nitrile hydratase variant obtained by mutating nitrile hydratase at (a) and (bh) amino acid substitution sites as shown in Table 3, the plasmid (4) recovered from the transformant (4) described in the above Reference Example 3 was used as the template, and the primer having the sequence defined in SEQ ID No: 16 in the Sequence Listing was used for carrying out the method using the mutagenesis kit described in Reference Example 2, whereby a plasmid (7) encoding the above nitrile hydratase variant was prepared. A competent cell of *Escherichia coli* HB101 (manufactured by Toyobo Co., Ltd.) was transformed with the plasmid to obtain a transformant (7). Moreover, the plasmid was prepared from the above-mentioned microbial cells by the alkaline SDS extraction method, and the base sequence of the nitrile hydratase gene was determined using a DNA sequencer. Then, it was confirmed that the transformant (7) had sequences according to the purpose in which mutation of 92nd Asp in the α-subunit with Glu was newly added to the plasmid (4) of Reference Example 3. In the production of an amide compound using the thus obtained transformant (7) and the transformant (4) to be its base, the initial reaction rate and thermal stability were compared in the same manner as in Example 1.

As a result, it was found that mutation of 92nd Asp in the α-subunit with Glu was newly added to the transformant (7), so that the initial reaction rate was improved by 1.58 times and thermal stability was improved by 1.30 times, as compared to those of the transformant (4).

TABLE 16

(Table 3)

| Transformant No. | Mutated Site | Change in Amino Acid Sequence | | Change in Base Sequence | | Improvement of Reaction Rate by α-92nd Substitution | Improvement of Thermal Stability by α-92nd Substitution |
|---|---|---|---|---|---|---|---|
| | | Before Substitution | After Substitution | Before Substitution | After Substitution | | |
| 5 | α-36th | Thr | Met | ACG | ATG | 1.65 times | 1.25 times |
| | α-92nd | Asp | Glu | GAC | GAG | | |
| | α-148th | Gly | Asp | GGC | GAC | | |
| | α-204th | Val | Arg | GTC | CGC | | |
| | β-41st | Phe | Ile | TTC | ATC | | |
| | β-51st | Phe | Val | TTC | GTC | | |
| | β-108th | Glu | Asp | GAG | GAT | | |

TABLE 16-continued (Table 3)

| Trans- formant No. | Mutated Site | Change in Amino Acid Sequence | | Change in Base Sequence | | Improvement of Recation Rate by α-92nd Substitution | Improvement of Thermal Stability by α-92nd Substitution |
|---|---|---|---|---|---|---|---|
| | | Before Substi- tution | After Substi- tution | Before Substi- tution | After Substi- tution | | |
| 6 | α-36th | Thr | Ser | ACG | TCG | 1.63 times | 1.23 times |
| | α-92nd | Asp | Glu | GAC | GAG | | |
| | β-33rd | Ala | Val | GCG | GTG | | |
| 7 | α-92nd | Asp | Glu | GAC | GAG | 1.58 times | 1.30 times |
| | β-40th | Thr | Ile | ACG | ATT | | |
| | β-61st | Ala | Val | GCC | GTC | | |

Reference Example 4

Construction of a Transformant (8) Substituted Amino Acid Having Nitrile Hydratase Activity In order to obtain a transformant (8) expressing the nitrile hydratase variant obtained by mutating nitrile hydratase at (ak) amino acid substitution sites as shown in Table 4, the plasma described in Example 68 of Patent Document 2 was used as the template, and the ribosome binding sequence was modified according to the method described in Example 1 to prepare a plasmid (8) encoding the above nitrile hydratase variant. A competent cell of *Escherichia coli* HB101 (manufactured by Toyobo Co., Ltd.) was transformed with the plasmid to obtain a transformant (8).

Reference Example 5

Construction of a Transformant (9) Substituted Amino Acid Having Nitrile Hydratase Activity In order to obtain a transformant (9) expressing the nitrile hydratase variant obtained by mutating nitrile hydratase at (ap) amino acid substitution sites as shown in Table 4, the plasma described in Example 73 of Patent Document 2 was used as the template, and the ribosome binding sequence was modified according to the method described in Example 1 to prepare a plasmid (9) encoding the above nitrile hydratase variant. A competent cell of *Escherichia coli* HB101 (manufactured by Toyobo Co., Ltd.) was transformed with the plasmid to obtain a transformant (9).

Reference Example 6

Construction of a Transformant (10) Substituted Amino Acid Having Nitrile Hydratase Activity In order to obtain a transformant (10) expressing the nitrile hydratase variant obtained by mutating nitrile hydratase at (bp) amino acid substitution sites as shown in Table 4, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 17 and 18 in the Sequence Listing were used for repeatedly carrying out the method described in Reference Example 2 per mutation point, whereby a plasmid (10) encoding the above nitrile hydratase variant was prepared. A competent cell of *Escherichia coli* HB101 (manufactured by Toyobo Co., Ltd.) was transformed with the plasmid to obtain a transformant (10).

TABLE 17

(Table 4)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 8 | β-37th | Phe | Val | TTC | GTC |
| | β-108th | Glu | Asp | GAG | GAT |
| | β-200th | Ala | Glu | GCC | GAG |
| 9 | α-6th | Leu | Thr | CTG | ACG |
| | α-19th | Ala | Val | GCG | GTG |
| | α-126th | Phe | Tyr | TTC | TAC |
| | β-46th | Met | Lys | ATG | AAG |
| | β-108th | Glu | Arg | GAG | CGG |
| | β-212th | Ser | Tyr | TCC | TAC |
| 10 | β-61st | Ala | Gly | GCC | GGC |
| | β-150th | Ala | Asn | GCG | AAT |

33
Example 5

Construction of a Transformant (11) Substituted Amino Acid Having Improved Nitrile Hydratase Activity and Improved Thermal Stability In order to obtain a transformant (11) expressing the nitrile hydratase variant obtained by mutating nitrile hydratase at (b) and (ak) amino acid substitution sites as shown in Table 5, the plasmid (8) recovered from the transformant (8) described in the above Reference Example 4 was used as the template, and the primer having the sequence defined in SEQ ID No: 19 in the Sequence Listing was used for carrying out the method using the mutagenesis kit described in Reference Example 2, whereby a plasmid (11) encoding the above nitrile hydratase variant was prepared. A competent cell of *Escherichia coli* HB101 (manufactured by Toyobo Co., Ltd.) was transformed with the plasmid to obtain a transformant (11). Moreover, the plasmid was prepared from the above-mentioned microbial cells by the alkaline SDS extraction method, and the base sequence of the nitrile hydratase gene was determined using a DNA sequencer. Then, it was confirmed that the transformant (11) had sequences according to the purpose in which mutation of 94th Met in the α-subunit with Ile was newly added to the plasmid (8) of Reference Example 4. In the production of an amide compound using the thus obtained transformant (11) and the transformant (8) to be its base, the initial reaction rate and thermal stability were compared in the same manner as in Example 1.

As a result, it was found that mutation of 94th Met in the α-subunit with Ile was newly added to the transformant (11), so that the initial reaction rate was improved by 1.45 times and thermal stability was improved by 1.38 times, as compared to those of the transformant (8).

Example 6

Construction of a Transformant (12) Substituted Amino Acid Having Improved Nitrile Hydratase Activity and Improved Thermal Stability In order to obtain a transformant (12) expressing the nitrile hydratase variant obtained by mutating nitrile hydratase at (b) and (ap) amino acid substitution sites as shown in Table 5, the plasmid (9) recovered from the transformant (9) described in the above Reference Example 5 was used as the template, and the primer having the sequence defined in SEQ ID No: 19 in the Sequence Listing was used for carrying out the method using the mutagenesis kit described in Reference Example 2, whereby a plasmid (12) encoding the above nitrile hydratase variant was prepared. A competent cell of *Escherichia coli* HB101 (manufactured by Toyobo Co., Ltd.) was transformed with the plasmid to obtain a transformant (12). Moreover, the plasmid was prepared from the above-mentioned microbial cells by the alkaline SDS extraction method, and the base sequence of the nitrile hydratase gene was determined using a DNA sequencer. Then, it was confirmed that the transformant (12) had sequences according to the purpose in which mutation of 94th Met in the α-subunit with Ile was newly added to the plasmid (9) of Reference Example 5. In the production of an amide compound using the thus obtained transformant (12) and the transformant (9) to be its base, the initial reaction rate and thermal stability were compared in the same manner as in Example 1.

As a result, it was found that mutation of 94th Met in the α-subunit with Ile was newly added to the transformant (12), so that the initial reaction rate was improved by 1.40 times and thermal stability was improved by 1.25 times, as compared to those of the transformant (9).

Example 7

Construction of a Transformant (13) Substituted Amino Acid Having Improved Nitrile Hydratase Activity and Improved Thermal Stability In order to obtain a transformant (13) expressing the nitrile hydratase variant obtained by mutating nitrile hydratase at (b) and (bp) amino acid substitution sites as shown in Table 5, the plasmid (10) recovered from the transformant (10) described in the above Reference Example 6 was used as the template, and the primer having the sequence defined in SEQ ID No: 19 in the Sequence Listing was used for carrying out the method using the mutagenesis kit described in Reference Example 2, whereby a plasmid (13) encoding the above nitrile hydratase variant was prepared. A competent cell of *Escherichia coli* HB101 (manufactured by Toyobo Co., Ltd.) was transformed with the plasmid to obtain a transformant (13). Moreover, the plasmid was prepared from the above-mentioned microbial cells by the alkaline SDS extraction method, and the base sequence of the nitrile hydratase gene was determined using a DNA sequencer. Then, it was confirmed that the transformant (13) had sequences according to the purpose in which mutation of 94th Met in the α-subunit with Ile was newly added to the plasmid (10) of Reference Example 6. In the production of an amide compound using the thus obtained transformant (13) and the transformant (10) to be its base, the initial reaction rate and thermal stability were compared in the same manner as in Example 1.

As a result, it was found that mutation of 94th Met in the α-subunit with Ile was newly added to the transformant (13), so that the initial reaction rate was improved by 1.32 times and thermal stability was improved by 1.35 times, as compared to those of the transformant (10).

TABLE 18

(Table 5)

| Trans-formant No. | Mutated Site | Change in Amino Acid Sequence | | Change in Base Sequence | | Improvement of Reaction Rate by α-94th Substitution | Improvement of Thermal Stability by α-94th Substitution |
|---|---|---|---|---|---|---|---|
| | | Before Substitution | After Substitution | Before Substitution | After Substitution | | |
| 11 | α-94th | Met | Ile | ATG | ATC | 1.45 times | 1.38 times |
| | β-37th | Phe | Val | TTC | GTC | | |
| | β-108th | Glu | Asp | GAG | GAT | | |
| | β-200th | Ala | Glu | GCC | GAG | | |
| 12 | α-6th | Leu | Thr | CTG | ACG | 1.40 times | 1.25 times |
| | α-19th | Ala | Val | GCG | GTG | | |

TABLE 18-continued (Table 5)

| Trans- formant No. | Mutated Site | Change in Amino Acid Sequence | | Change in Base Sequence | | Improvement of Reaction Rate by α-94th Substitution | Improvement of Thermal Stability by α-94th Substitution |
|---|---|---|---|---|---|---|---|
| | | Before Substi- tution | After Substi- tution | Before Substi- tution | After Substi- tution | | |
| | α-94th | Met | Ile | ATG | ATC | | |
| | α-126th | Phe | Tyr | TTC | TAC | | |
| | β-46th | Met | Lys | ATG | AAG | | |
| | β-108th | Glu | Arg | GAG | CGG | | |
| | β-212th | Ser | Tyr | TCC | TAC | | |
| 13 | α-94th | Met | Ile | ATG | ATC | 1.32 times | 1.35 times |
| | β-61st | Ala | Gly | GCC | GGC | | |
| | β-150th | Ala | Asn | GCG | AAT | | |

Reference Example 7

Construction of a Transformant (14) Substituted Amino Acid Having Nitrile Hydratase Activity In order to obtain a transformant (14) expressing the nitrile hydratase variant obtained by mutating nitrile hydratase at (an) amino acid substitution sites as shown in Table 6, the plasma described in Example 71 of Patent Document 2 was used as the template, and the ribosome binding sequence was modified according to the method described in Example 1 to prepare a plasmid (14) encoding the above nitrile hydratase variant. A competent cell of *Escherichia coli* HB101 (manufactured by Toyobo Co., Ltd.) was transformed with the plasmid to obtain a transformant (14).

Reference Example 8

Construction of a Transformant (15) Substituted Amino Acid Having Nitrile Hydratase Activity In order to obtain a transformant (15) expressing the nitrile hydratase variant obtained by mutating nitrile hydratase at (be) amino acid substitution sites as shown in Table 6, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 20 and 21 in the Sequence Listing were used for repeatedly carrying out the method described in Reference Example 2 per mutation point, whereby a plasmid (15) encoding the above nitrile hydratase variant was prepared. A competent cell of *Escherichia coli* HB101 (manufactured by Toyobo Co., Ltd.) was transformed with the plasmid to obtain a transformant (15).

Reference Example 9

Construction of a Transformant (16) Substituted Amino Acid Having Nitrile Hydratase Activity In order to obtain a transformant (16) expressing the nitrile hydratase variant obtained by mutating nitrile hydratase at (br) amino acid substitution sites as shown in Table 6, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 22 and 23 in the Sequence Listing were used for repeatedly carrying out the method described in Reference Example 2 per mutation point, whereby a plasmid (16) encoding the above nitrile hydratase variant was prepared. A competent cell of *Escherichia coli* HB101 (manufactured by Toyobo Co., Ltd.) was transformed with the plasmid to obtain a transformant (16).

TABLE 19

(Table 6)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 14 | β-48th | Leu | Val | CTG | GTG |
| | β-108th | Glu | Arg | GAG | CGG |
| | β-212th | Ser | Tyr | TCC | TAC |
| 15 | β-40th | Thr | Val | ACG | GTG |
| | β-218th | Cys | Met | TGC | ATG |
| 16 | β-160th | Arg | Cys | CGG | TGT |
| | β-168th | Thr | Glu | ACG | GAG |

Example 8

Construction of a Transformant (17) Substituted Amino Acid Having Improved Nitrile Hydratase Activity and Improved Thermal Stability In order to obtain a transformant (17) expressing the nitrile hydratase variant obtained by mutating nitrile hydratase at (c) and (an) amino acid substitution sites as shown in Table 7, the plasmid (14) recovered from the transformant (14) described in the above Reference Example 7 was used as the template, and the primer having the sequence defined in SEQ ID No: 24 in the Sequence Listing was used for carrying out the method using the mutagenesis kit described in Reference Example 2, whereby a plasmid (17) encoding the above nitrile hydratase variant was prepared. A competent cell of *Escherichia coli* HB101 (manufactured by Toyobo Co., Ltd.) was transformed with the plasmid to obtain a transformant (17). Moreover, the plasmid was prepared from the above-mentioned microbial cells by the alkaline SDS extraction method, and the base sequence of the nitrile hydratase gene was determined using a DNA sequencer. Then, it was confirmed that the transformant (17) had sequences according to the purpose in which mutation of 197th Gly in the α-subunit with Cys was newly added to the plasmid (14) of Reference Example 7. In the production of an amide compound using the thus obtained transformant (17) and the transformant (14) to be its base, the initial reaction rate and thermal stability were compared in the same manner as in Example 1.

As a result, it was found that mutation of 197th Gly in the α-subunit with Cys was newly added to the transformant (17), so that the initial reaction rate was improved by 1.80 times and thermal stability was improved by 1.25 times, as compared to those of the transformant (14).

Example 9

Construction of a Transformant (18) Substituted Amino Acid Having Improved Nitrile Hydratase Activity and Improved Thermal Stability In order to obtain a transformant (18) expressing the nitrile hydratase variant obtained by mutating nitrile hydratase at (c) and (be) amino acid substitution sites as shown in Table 7, the plasmid (15) recovered from the transformant (15) described in the above Reference Example 8 was used as the template, and the primer having the sequence defined in SEQ ID No: 24 in the Sequence Listing was used for carrying out the method using the mutagenesis kit described in Reference Example 2, whereby a plasmid (18) encoding the above nitrile hydratase variant was prepared. A competent cell of *Escherichia coli* HB101 (manufactured by Toyobo Co., Ltd.) was transformed with the plasmid to obtain a transformant (18). Moreover, the plasmid was prepared from the above-mentioned microbial cells by the alkaline SDS extraction method, and the base sequence of the nitrile hydratase gene was determined using a DNA sequencer. Then, it was confirmed that the transformant (18) had sequences according to the purpose in which mutation of 197th Gly in the α-subunit with Cys was newly added to the plasmid (15) of Reference Example 8. In the production of an amide compound using the thus obtained transformant (18) and the transformant (15) to be its base, the initial reaction rate and thermal stability were compared in the same manner as in Example 1.

As a result, it was found that mutation of 197th Gly in the α-subunit with Cys was newly added to the transformant (18), so that the initial reaction rate was improved by 1.86 times and thermal stability was improved by 1.40 times, as compared to those of the transformant (15).

Example 10

Construction of a Transformant (19) Substituted Amino Acid Having Improved Nitrile Hydratase Activity and Improved Thermal Stability In order to obtain a transformant (19) expressing the nitrile hydratase variant obtained by mutating nitrile hydratase at (c) and (br) amino acid substitution sites as shown in Table 7, the plasmid (16) recovered from the transformant (16) described in the above Reference Example 9 was used as the template, and the primer having the sequence defined in SEQ ID No: 24 in the Sequence Listing was used for carrying out the method using the mutagenesis kit described in Reference Example 2, whereby a plasmid (19) encoding the above nitrile hydratase variant was prepared. A competent cell of *Escherichia coli* HB101 (manufactured by Toyobo Co., Ltd.) was transformed with the plasmid to obtain a transformant (19). Moreover, the plasmid was prepared from the above-mentioned microbial cells by the alkaline SDS extraction method, and the base sequence of the nitrile hydratase gene was determined using a DNA sequencer. Then, it was confirmed that the transformant (19) had sequences according to the purpose in which mutation of 197th Gly in the α-subunit with Cys was newly added to the plasmid (16) of Reference Example 9. In the production of an amide compound using the thus obtained transformant (19) and the transformant (16) to be its base, the initial reaction rate and thermal stability were compared in the same manner as in Example 1.

As a result, it was found that mutation of 197th Gly in the α-subunit with Cys was newly added to the transformant (19), so that the initial reaction rate was improved by 1.68 times and thermal stability was improved by 1.20 times, as compared to those of the transformant (16).

TABLE 20

(Table 7)

| Transformant No. | Mutated Site | Change in Amino Acid Sequence | | Change in Base Sequence | | Improvement of Reaction Rate by α-197th Substitution | Improvement of Thermal Stability by α-197th Substitution |
| --- | --- | --- | --- | --- | --- | --- | --- |
| | | Before Substitution | After Substitution | Before Substitution | After Substitution | | |
| 17 | α-197th | Gly | Cys | GGC | TGC | 1.80 times | 1.25 times |
| | β-48th | Leu | Val | CTG | GTG | | |
| | β-108th | Glu | Arg | GAG | CGG | | |
| | β-212th | Ser | Tyr | TCC | TAC | | |

TABLE 20-continued (Table 7)

| Transformant No. | Mutated Site | Change in Amino Acid Sequence Before Substitution | Change in Amino Acid Sequence After Substitution | Change in Base Sequence Before Substitution | Change in Base Sequence After Substitution | Improvement of Reaction Rate by α-197th Substitution | Improvement of Thermal Stability by α-197th Substitution |
|---|---|---|---|---|---|---|---|
| 18 | α-197th | Gly | Cys | GGC | TGC | 1.86 times | 1.40 times |
|  | β-40th | Thr | Val | ACG | GTG |  |  |
|  | β-218th | Cys | Met | TGC | ATG |  |  |
| 19 | α-197th | Gly | Cys | GGC | TGC | 1.68 times | 1.20 times |
|  | β-160th | Arg | Cys | CGG | TGT |  |  |
|  | β-168th | Thr | Glu | ACG | GAG |  |  |

Reference Example 10

Construction of a Transformant (20) Substituted Amino Acid Having Nitrile Hydratase Activity In order to obtain a transformant (20) expressing the nitrile hydratase variant obtained by mutating nitrile hydratase at (ar) amino acid substitution sites as shown in Table 8, the plasma described in Example 75 of Patent Document 2 was used as the template, and the ribosome binding sequence was modified according to the method described in Example 1 to prepare a plasmid (20) encoding the above nitrile hydratase variant. A competent cell of *Escherichia coli* HB101 (manufactured by Toyobo Co., Ltd.) was transformed with the plasmid to obtain a transformant (20).

Reference Example 11

Construction of a Transformant (21) Substituted Amino Acid Having Nitrile Hydratase Activity In order to obtain a transformant (21) expressing the nitrile hydratase variant obtained by mutating nitrile hydratase at (ax) amino acid substitution sites as shown in Table 8, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 25 and 26 in the Sequence Listing were used for repeatedly carrying out the method described in Reference Example 2 per mutation point, whereby a plasmid (21) encoding the above nitrile hydratase variant was prepared. A competent cell of *Escherichia coli* HB101 (manufactured by Toyobo Co., Ltd.) was transformed with the plasmid to obtain a transformant (21).

Reference Example 12

Construction of a Transformant (22) Substituted Amino Acid Having Nitrile Hydratase Activity In order to obtain a transformant (22) expressing the nitrile hydratase variant obtained by mutating nitrile hydratase at (bd) amino acid substitution sites as shown in Table 8, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 27 and 28 in the Sequence Listing were used for repeatedly carrying out the method described in Reference Example 2 per mutation point, whereby a plasmid (22) encoding the above nitrile hydratase variant was prepared. A competent cell of *Escherichia coli* HB101 (manufactured by Toyobo Co., Ltd.) was transformed with the plasmid to obtain a transformant (22).

TABLE 21

(Table 8)

| Transformant No. | Mutated Site | Change in Amino Acid Sequence After Substitution | Change in Amino Acid Sequence Before Substitution | Change in Base Sequence Before Substitution | Change in Base Sequence After Substitution |
|---|---|---|---|---|---|
| 20 | α-6th | Leu | Ala | CTG | GCG |
|  | α-19th | Ala | Val | GCG | GTG |
|  | α-126th | Phe | Tyr | TTC | TAC |
|  | β-127th | Leu | Ser | CTG | TCG |
|  | β-160th | Arg | Trp | CGG | TGG |
|  | β-186th | Leu | Arg | CTG | CGG |
| 21 | α-36th | Thr | Gly | ACG | GGG |
|  | α-188th | Thr | Gly | ACC | GGC |
| 22 | β-176th | Tyr | Ala | TAC | GCC |
|  | β-217th | Asp | Val | GAC | GTC |

Example 11

Construction of a Transformant (23) Substituted Amino Acid Having Improved Nitrile Hydratase Activity and Improved Thermal Stability In order to obtain a transformant (23) expressing the nitrile hydratase variant obtained by mutating nitrile hydratase at (d) and (ar) amino acid substitution sites as shown in Table 9, the plasmid (20) recovered from the transformant (20) described in the above Reference Example 10 was used as the template, and the primer having the sequence defined in SEQ ID No: 29 in the Sequence Listing was used for carrying out the method using the mutagenesis kit described in Reference Example 2, whereby a plasmid (23) encoding the above nitrile hydratase variant was prepared. A competent cell of *Escherichia coli* HB101 (manufactured by Toyobo Co., Ltd.) was transformed with the plasmid to obtain a transformant (23). Moreover, the plasmid was prepared from the above-mentioned microbial cells by the alkaline SDS extraction method, and the base sequence of the nitrile hydratase gene was determined using a DNA sequencer. Then, it was confirmed that the transformant (23) had sequences according to the purpose in which mutation of 4th Val in the β-subunit with Met was newly added to the plasmid (20) of Reference Example 10. In the production of an amide compound using the thus obtained transformant (23) and the transformant (20) to be its base, the initial reaction rate and thermal stability were compared in the same manner as in Example 1.

As a result, it was found that mutation of 4th Val in the β-subunit with Met was newly added to the transformant (23), so that the initial reaction rate was improved by 1.25 times and thermal stability was improved by 1.35 times, as compared to those of the transformant (20).

Example 12

Construction of a Transformant (24) Substituted Amino Acid Having Improved Nitrile Hydratase Activity and Improved Thermal Stability In order to obtain a transformant (24) expressing the nitrile hydratase variant obtained by mutating nitrile hydratase at (d) and (ax) amino acid substitution sites as shown in Table 9, the plasmid (21) recovered from the transformant (21) described in the above Reference Example 11 was used as the template, and the primer having the sequence defined in SEQ ID No: 29 in the Sequence Listing was used for carrying out the method using the mutagenesis kit described in Reference Example 2, whereby a plasmid (24) encoding the above nitrile hydratase variant was prepared. A competent cell of *Escherichia coli* HB101 (manufactured by Toyobo Co., Ltd.) was transformed with the plasmid to obtain a transformant (24). Moreover, the plasmid was prepared from the above-mentioned microbial cells by the alkaline SDS extraction method, and the base sequence of the nitrile hydratase gene was determined using a DNA sequencer. Then, it was confirmed that the transformant (24) had sequences according to the purpose in which mutation of 4th Val in the β-subunit with Met was newly added to the plasmid (21) of Reference Example 11. In the production of an amide compound using the thus obtained transformant (24) and the transformant (21) to be its base, the initial reaction rate and thermal stability were compared in the same manner as in Example 1.

As a result, it was found that mutation of 4th Val in the β-subunit with Met was newly added to the transformant (24), so that the initial reaction rate was improved by 1.32 times and thermal stability was improved by 1.39 times, as compared to those of the transformant (21).

Example 13

Construction of a Transformant (25) Substituted Amino Acid Having Improved Nitrile Hydratase Activity and Improved Thermal Stability In order to obtain a transformant (25) expressing the nitrile hydratase variant obtained by mutating nitrile hydratase at (d) and (bd) amino acid substitution sites as shown in Table 9, the plasmid (22) recovered from the transformant (22) described in the above Reference Example 12 was used as the template, and the primer having the sequence defined in SEQ ID No: 29 in the Sequence Listing was used for carrying out the method using the mutagenesis kit described in Reference Example 2, whereby a plasmid (25) encoding the above nitrile hydratase variant was prepared. A competent cell of *Escherichia coli* HB101 (manufactured by Toyobo Co., Ltd.) was transformed with the plasmid to obtain a transformant (19). Moreover, the plasmid was prepared from the above-mentioned microbial cells by the alkaline SDS extraction method, and the base sequence of the nitrile hydratase gene was determined using a DNA sequencer. Then, it was confirmed that the transformant (25) had sequences according to the purpose in which mutation of 4th Val in the β-subunit with Met was newly added to the plasmid (22) of Reference Example 12. In the production of an amide compound using the thus obtained transformant (25) and the transformant (22) to be its base, the initial reaction rate and thermal stability were compared in the same manner as in Example 1.

As a result of comparison of the initial reaction rate and thermal stability between the transformant (25) and the transformant (22), it was found that mutation of 4th Val in the β-subunit with Met was newly added to the transformant (25), so that the initial reaction rate was improved by 1.25 times and thermal stability was improved by 1.25 times, as compared to those of the transformant (22).

TABLE 22

(Table 9)

| Trans-formant No. | Mutated Site | Change in Amino Acid Sequence | | Change in Base Sequence | | Improvement of Reaction Rate by a-94th Substitution | Improvement of Thermal Stability by 1-94th Substitution |
|---|---|---|---|---|---|---|---|
| | | Before Substitution | After Substitution | Before Substitution | After Substitution | | |
| 23 | α-6th | Leu | Ala | CTG | GCG | 1.25 times | 1.35 times |
| | α-19th | Ala | Val | GCG | GTG | | |
| | α-126th | Phe | Tyr | TTC | TAC | | |
| | β-4th | Val | Met | GTG | ATG | | |
| | β-127th | Leu | Ser | CTG | TCG | | |

TABLE 22-continued (Table 9)

| Trans-formant No. | Mutated Site | Change in Amino Acid Sequence | | Change in Base Sequence | | Improvement of Reaction Rate by a-94th Substitution | Improvement of Thermal Stability by 1-94th Substitution |
|---|---|---|---|---|---|---|---|
| | | Before Substi-tution | After Substi-tution | Before Substi-tution | After Substi-tution | | |
| | β-160th | Arg | Trp | CGG | TGG | | |
| | β-186th | Leu | Arg | CTG | CGG | | |
| 24 | α-36th | Thr | Gly | ACG | GGG | 1.32 times | 1.39 times |
| | α-188th | Thr | Gly | ACC | GGC | | |
| | β-4th | Val | Met | GTG | ATG | | |
| 25 | α-4th | Val | Met | GTG | ATG | 1.25 times | 1.25 times |
| | β-176th | Tyr | Ala | TAC | GCC | | |
| | β-217th | Asp | Val | GAC | GTC | | |

Reference Example 13

Construction of a Transformant (26) Substituted Amino Acid Having Nitrile Hydratase Activity In order to obtain a transformant (26) expressing the nitrile hydratase variant obtained by mutating nitrile hydratase at (ao) amino acid substitution sites as shown in Table 10, the plasma described in Example 72 of Patent Document 2 was used as the template, and the ribosome binding sequence was modified according to the method described in Example 1 to prepare a plasmid (26) encoding the above nitrile hydratase variant. A competent cell of *Escherichia coli* HB101 (manufactured by Toyobo Co., Ltd.) was transformed with the plasmid to obtain a transformant (26).

Reference Example 14

Construction of a Transformant (27) Substituted Amino Acid Having Nitrile Hydratase Activity In order to obtain a transformant (27) expressing the nitrile hydratase variant obtained by mutating nitrile hydratase at (at) amino acid substitution sites as shown in Table 10, the plasma described in Example 77 of Patent Document 2 was used as the template, and the ribosome binding sequence was modified according to the method described in Example 1 to prepare a plasmid (27) encoding the above nitrile hydratase variant. A competent cell of *Escherichia coli* HB101 (manufactured by Toyobo Co., Ltd.) was transformed with the plasmid to obtain a transformant (27).

Comparative Example 1

Construction of a Transformant (28) Substituted Amino Acid Having Improved Nitrile Hydratase Activity In order to obtain a transformant (28) expressing the nitrile hydratase variant obtained by mutating nitrile hydratase at 8th of the β-subunit and (ao) amino acid substitution sites as shown in Table 11, the plasmid (26) recovered from the transformant (26) described in the above Reference Example 13 was used as the template, and the primer having the sequence defined in SEQ ID No: 30 in the Sequence Listing was used for carrying out the method using the mutagenesis kit described in Reference Example 2, whereby a plasmid (28) encoding the above nitrile hydratase variant was prepared. A competent cell of *Escherichia coli* HB101 (manufactured by Toyobo Co., Ltd.) was transformed with the plasmid to obtain a transformant (28). Moreover, the plasmid was prepared from the above-mentioned microbial cells by the alkaline SDS extraction method, and the base sequence of the nitrile hydratase gene was determined using a DNA sequencer. Then, it was confirmed that the transformant (28) had sequences according to the purpose in which mutation of 8th Gly in the β-subunit with Ala was newly added to the plasmid (26) of Reference Example 13. In the production of an amide compound using the thus obtained transformant (28) and the transformant (26) to be its base, the initial reaction rate and thermal stability were compared in the same manner as in Example 1.

TABLE 23

(Table 10)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 26 | β-127th | Leu | Ser | CTG | TCG |
| | β-160th | Arg | Trp | CGG | TGG |
| | β-186th | Leu | Arg | CTG | CGG |
| 27 | α-19th | Ala | Val | GCG | GTG |
| | α-71st | Arg | His | CGT | CAT |
| | α-126th | Phe | Tyr | TTC | TAC |
| | β-37th | Phe | Leu | TTC | CTC |
| | β-108th | Glu | Asp | GAG | GAT |
| | β-200th | Ala | Glu | GCC | GAG |

As a result of comparison, it was found that mutation of 8th Gly in the β-subunit with Ala was newly added to the transformant (28), so that the initial reaction rate was improved by 1.35 times and thermal stability was lowered by 0.65 times, as compared to those of the transformant (26).

Comparative Example 2

Construction of a Transformant (29) Substituted Amino Acid Having Improved Nitrile Hydratase Activity In order to obtain a transformant (29) expressing the nitrile hydratase variant obtained by mutating nitrile hydratase at 8th of the β-subunit and (at) amino acid substitution sites as shown in Table 11, the plasmid (27) recovered from the transformant (27) described in the above Reference Example 14 was used as the template, and the primer having the sequence defined in SEQ ID No: 30 in the Sequence Listing was used for carrying out the method using the mutagenesis kit described in Reference Example 2, whereby a plasmid (29) encoding the above nitrile hydratase variant was prepared. A competent cell of *Escherichia coli* HB101 (manufactured by Toyobo Co., Ltd.) was transformed with the plasmid to obtain a transformant (29). Moreover, the plasmid was prepared from the above-mentioned microbial cells by the alkaline SDS extraction method, and the base sequence of the nitrile hydratase gene was determined using a DNA sequencer. Then, it was confirmed that the transformant (29) had sequences according to the purpose in which mutation of 8th Gly in the β-subunit with Ala was newly added to the plasmid (27) of Reference Example 14. In the production of an amide compound using the thus obtained transformant (29) and the transformant (27) to be its base, the initial reaction rate and thermal stability were compared in the same manner as in Example 1.

As a result, it was found that mutation of 8th Gly in the β-subunit with Ala was newly added to the transformant (29), so that the initial reaction rate was improved by 1.40 times and thermal stability was lowered by 0.31 times, as compared to those of the transformant (27).

Comparative Example 3

Construction of a Transformant (30) Substituted Amino Acid Having Improved Nitrile Hydratase Activity In order to obtain a transformant (30) expressing the nitrile hydratase variant obtained by mutating nitrile hydratase at 8th of the β-subunit and (br) amino acid substitution sites as shown in Table 11, the plasmid (16) recovered from the transformant (16) described in the above Reference Example 9 was used as the template, and the primer having the sequence defined in SEQ ID No: 30 in the Sequence Listing was used for carrying out the method using the mutagenesis kit described in Reference Example 2, whereby a plasmid (30) encoding the above nitrile hydratase variant was prepared. A competent cell of *Escherichia coli* HB101 (manufactured by Toyobo Co., Ltd.) was transformed with the plasmid to obtain a transformant (30). Moreover, the plasmid was prepared from the above-mentioned microbial cells by the alkaline SDS extraction method, and the base sequence of the nitrile hydratase gene was determined using a DNA sequencer. Then, it was confirmed that the transformant (30) had sequences according to the purpose in which mutation of 8th Gly in the β-subunit with Ala was newly added to the plasmid (16) of Reference Example 9. In the production of an amide compound using the thus obtained transformant (30) and the transformant (16) to be its base, the initial reaction rate and thermal stability were compared in the same manner as in Example 1.

As a result, it was found that mutation of 8th Gly in the β-subunit with Ala was newly added to the transformant (30), so that the initial reaction rate was improved by 1.32 times and thermal stability was lowered by 0.52 times, as compared to those of the transformant (16).

TABLE 24

(Table 11)

| Transformant No. | Mutated Site | Change in Amino Acid Sequence | | Change in Base Sequence | | Improvement of Reaction Rate by β-8th Substitution | Improvement of Thermal Stability by β-8th Substitution |
|---|---|---|---|---|---|---|---|
| | | Before Substitution | After Substitution | Before Substitution | After Substitution | | |
| 28 | α-8th | Gly | Ala | GGC | GCC | 1.35 times | 0.65 times |
| | β-127th | Leu | Ser | CTG | TCG | | |
| | β-160h | Arg | Trp | CGG | TGG | | |
| | β-186th | Leu | Arg | CTG | CGG | | |
| 29 | α-19th | Ala | Val | GCG | GTG | 1.40 times | 0.31 times |
| | α-71st | Arg | His | CGT | CAT | | |
| | β-126th | Phe | Tyr | TTC | TAC | | |
| | β-8th | Gly | Ala | GGC | GCC | | |
| | β-37th | Phe | Leu | TTC | CTC | | |
| | β-108th | Glu | Asp | GAG | GAT | | |
| | β-200th | Ala | Glu | GCC | GAG | | |
| 30 | β-8th | Gly | Ala | GGC | GCC | 1.32 times | 0.52 times |
| | β-160th | Arg | Cys | CGG | TGT | | |
| | β-168th | Thr | Glu | ACG | GAG | | |

Reference Example 15

Construction of a Transformant (31) Substituted Amino Acid Having Nitrile Hydratase Activity In order to obtain a transformant (31) expressing the nitrile hydratase variant obtained by mutating nitrile hydratase at (au) amino acid substitution sites as shown in Table 12, the plasma described in Example 78 of Patent Document 2 was used as the template, and the ribosome binding sequence was modified according to the method described in Example 1 to prepare a plasmid (31) encoding the above nitrile hydratase variant. A competent cell of *Escherichia coli* HB101 (manufactured by Toyobo Co., Ltd.) was transformed with the plasmid to obtain a transformant (31).

Reference Example 16

Construction of a Transformant (32) Substituted Amino Acid Having Nitrile Hydratase Activity In order to obtain a transformant (32) expressing the nitrile hydratase variant obtained by mutating nitrile hydratase at (bf) amino acid substitution sites as shown in Table 12, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 31 and 32 in the Sequence Listing were used for repeatedly carrying out the method described in Reference Example 2 per mutation point, whereby a plasmid (32) encoding the above nitrile hydratase variant was prepared. A competent cell of *Escherichia coli* HB101 (manufactured by Toyobo Co., Ltd.) was transformed with the plasmid to obtain a transformant (32).

TABLE 25

(Table 12)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 31 | α-19th | Ala | Val | GCG | GTG |
| | α-71st | Arg | His | CGT | CAT |
| | α-126th | Phe | Tyr | TTC | TAC |
| | β-37th | Phe | Val | TTC | GTC |
| | β-108th | Glu | Asp | GAG | GAT |
| | β-200th | Ala | Glu | GCC | GAG |
| 32 | β-33rd | Ala | Met | GCG | ATG |
| | β-176th | Tyr | Thr | TAC | ACC |

Example 14

Construction of a Transformant (33) Substituted Amino Acid Having Improved Nitrile Hydratase Activity and Improved Thermal Stability In order to obtain a transformant (33) expressing the nitrile hydratase variant obtained by mutating nitrile hydratase at (f) and (au) amino acid substitution sites as shown in Table 13, the plasmid (31) recovered from the transformant (31) described in the above Reference Example 15 was used as the template, and the primer having the sequence defined in SEQ ID No: 33 in the Sequence Listing was used for carrying out the method using the mutagenesis kit described in Reference Example 2, whereby a plasmid (33) encoding the above nitrile hydratase variant was prepared. A competent cell of *Escherichia coli* HB101 (manufactured by Toyobo Co., Ltd.) was transformed with the plasmid to obtain a transformant (33). Moreover, the plasmid was prepared from the above-mentioned microbial cells by the alkaline SDS extraction method, and the base sequence of the nitrile hydratase gene was determined using a DNA sequencer. Then, it was confirmed that the transformant (33) had sequences according to the purpose in which mutation of 79th His in the β-subunit with Asn was newly added to the plasmid (31) of Reference Example 15. In the production of an amide compound using the thus obtained transformant (33) and the transformant (31) to be its base, the initial reaction rate and thermal stability were compared in the same manner as in Example 1.

As a result, it was found that mutation of 79th His in the β-subunit with Asn was newly added to the transformant (33), so that the initial reaction rate was improved by 1.29 times and thermal stability was improved by 1.82 times, as compared to those of the transformant (31).

Example 15

Construction of a Transformant (34) Substituted Amino Acid Having Improved Nitrile Hydratase Activity and Improved Thermal Stability In order to obtain a transformant (34) expressing the nitrile hydratase variant obtained by mutating nitrile hydratase at (f) and (bf) amino acid substitution sites as shown in Table 13, the plasmid (32) recovered from the transformant (32) described in the above Reference Example 16 was used as the template, and the primer having the sequence defined in SEQ ID No: 33 in the Sequence Listing was used for carrying out the method using the mutagenesis kit described in Reference Example 2, whereby a plasmid (34) encoding the above nitrile hydratase variant was prepared. A competent cell of *Escherichia coli* HB101 (manufactured by Toyobo Co., Ltd.) was transformed with the plasmid to obtain a transformant (34). Moreover, the plasmid was prepared from the above-mentioned microbial cells by the alkaline SDS extraction method, and the base sequence of the nitrile hydratase gene was determined using a DNA sequencer. Then, it was confirmed that the transformant (34) had sequences according to the purpose in which mutation of 79th His in the β-subunit with Asn was newly added to the plasmid (32) of Reference Example 16. In the production of an amide compound using the thus obtained transformant (34) and the transformant (32) to be its base, the initial reaction rate and thermal stability were compared in the same manner as in Example 1.

As a result, it was found that mutation of 79th His in the β-subunit with Asn was newly added to the transformant (34), so that the initial reaction rate was improved by 1.25 times and thermal stability was improved by 1.76 times, as compared to those of the transformant (32).

Example 16

Construction of a Transformant (35) Substituted Amino Acid Having Improved Nitrile Hydratase Activity and Improved Thermal Stability In order to obtain a transformant (35) expressing the nitrile hydratase variant obtained by mutating nitrile hydratase at (f) and (bp) amino acid substitution sites as shown in Table 13, the plasmid (10) recovered from the transformant (10) described in the above Reference Example 6 was used as the template, and the primer having the sequence defined in SEQ ID No: 33 in the Sequence Listing was used for carrying out the method using the mutagenesis kit described in Reference Example 2, whereby a plasmid (35) encoding the above nitrile hydratase variant was prepared. A competent cell of *Escherichia coli* HB101 (manufactured by Toyobo Co., Ltd.) was transformed with the plasmid to obtain a transformant (35). Moreover, the plasmid was prepared from the above-mentioned microbial cells by the alkaline SDS extraction method, and the base sequence of the nitrile hydratase gene was determined using a DNA sequencer. Then, it was confirmed that the transformant (35) had sequences according to the purpose in which mutation of 79th His in the β-subunit with Asn was newly added to the plasmid (10) of Reference Example 6. In the production of an amide compound using the thus obtained transformant (35) and the transformant (10) to be its base, the initial reaction rate and thermal stability were compared in the same manner as in Example 1.

As a result, it was found that mutation of 79th His in the β-subunit with Asn was newly added to the transformant (35), so that the initial reaction rate was improved by 1.30 times and thermal stability was improved by 1.72 times, as compared to those of the transformant (10).

TABLE 26

(Table 13)

| Transformant No. | Mutated Site | Change in Amino Acid Sequence | | Change in Base Sequence | | Improvement of Reaction Rate by β-79th Substitution | Improvement of Thermal Stability by β-79th Substitution |
|---|---|---|---|---|---|---|---|
| | | Before Substitution | After Substitution | Before Substitution | After Substitution | | |
| 33 | α-19th | Ala | Val | GCG | GTG | 1.29 times | 1.82 times |
| | α-71st | Arg | His | CGT | CAT | | |
| | α-126th | Phe | Tyr | TTC | TAC | | |
| | β-37th | Phe | Val | TTC | GTC | | |
| | β-79th | His | Asn | CAC | AAC | | |
| | β-108h | Glu | Asp | GAG | GAT | | |
| | β-200th | Ala | Glu | GCC | GAG | | |
| 34 | β-33rd | Ala | Met | GCG | ATG | 1.25 times | 1.76 times |
| | β-79th | His | Asn | CAC | AAC | | |
| | β-176th | Tyr | Thr | TAC | ACC | | |
| 35 | β-61st | Ala | Gly | GCC | GGC | 1.30 times | 1.72 times |
| | β-79th | His | Asn | CAC | AAC | | |
| | β-150th | Ala | Asn | GCG | AAT | | |

Reference Example 17

Construction of a Transformant (36) Substituted Amino Acid Having Nitrile Hydratase Activity In order to obtain a transformant (36) expressing the nitrile hydratase variant obtained by mutating nitrile hydratase at (aa) amino acid substitution sites as shown in Table 14, the plasma described in Example 58 of Patent Document 2 was used as the template, and the ribosome binding sequence was modified according to the method described in Example 1 to prepare a plasmid (36) encoding the above nitrile hydratase variant. A competent cell of *Escherichia coli* HB101 (manufactured by Toyobo Co., Ltd.) was transformed with the plasmid to obtain a transformant (36).

Reference Example 18

Construction of a Transformant (37) Substituted Amino Acid Having Nitrile Hydratase Activity In order to obtain a transformant (37) expressing the nitrile hydratase variant obtained by mutating nitrile hydratase at (ah) amino acid substitution sites as shown in Table 14, the plasma described in Example 65 of Patent Document 2 was used as the template, and the ribosome binding sequence was modified according to the method described in Example 1 to prepare a plasmid (37) encoding the above nitrile hydratase variant. A competent cell of *Escherichia coli* HB101 (manufactured by Toyobo Co., Ltd.) was transformed with the plasmid to obtain a transformant (37).

Reference Example 19

Construction of a Transformant (38) Substituted Amino Acid Having Nitrile Hydratase Activity In order to obtain a transformant (38) expressing the nitrile hydratase variant obtained by mutating nitrile hydratase at (aq) amino acid substitution sites as shown in Table 14, the plasma described in Example 74 of Patent Document 2 was used as the template, and the ribosome binding sequence was modified according to the method described in Example 1 to prepare a plasmid (38) encoding the above nitrile hydratase variant. A competent cell of *Escherichia coli* HB101 (manufactured by Toyobo Co., Ltd.) was transformed with the plasmid to obtain a transformant (38).

Example 17

Construction of a Transformant (39) Substituted Amino Acid Having Improved Nitrile Hydratase Activity and Improved Thermal Stability In order to obtain a transformant (39) expressing the nitrile hydratase variant obtained by mutating nitrile hydratase at (g) and (aa) amino acid substitution sites as shown in Table 15, the plasmid (36) recovered from the transformant (36) described in the above Reference Example 17 was used as the template, and the primer having the sequence defined in SEQ ID No: 34 in the Sequence Listing was used for carrying out the method using the mutagenesis kit described in Reference Example 2, whereby a plasmid (39) encoding the above nitrile hydratase variant was prepared. A competent cell of *Escherichia coli* HB101 (manufactured by Toyobo Co., Ltd.) was transformed with the plasmid to obtain a transformant (39). Moreover, the plasmid was prepared from the above-mentioned microbial cells by the alkaline SDS extraction method, and the base sequence of the nitrile hydratase gene was determined using a DNA sequencer. Then, it was confirmed that the transformant (39) had sequences according to the purpose in which mutation of 96th Gln in the β-subunit with Arg was newly added to the plasmid (36) of Reference Example 17. In the production of an amide compound using the thus obtained transformant (39) and the transformant (36) to be its base, the initial reaction rate and thermal stability were compared in the same manner as in Example 1.

As a result, it was found that mutation of 96th Gln in the β-subunit with Arg was newly added to the transformant (39), so that the initial reaction rate was improved by 1.33 times and thermal stability was improved by 1.25 times, as compared to those of the transformant (36).

Example 18

Construction of a Transformant (40) Substituted Amino Acid Having Improved Nitrile Hydratase Activity and Improved Thermal Stability In order to obtain a transformant (40) expressing the nitrile hydratase variant obtained by mutating nitrile hydratase at (g) and (ah) amino acid substitution sites as shown in Table 15, the plasmid (37) recovered from the transformant (37)

TABLE 27

(Table 14)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 36 | α-36th | Thr | Met | ACG | ATG |
| | α-126th | Phe | Tyr | TTC | TAC |
| 37 | α-36th | Thr | Met | ACG | ATG |
| | α-148th | Gly | Asp | GGC | GAC |
| | α-204th | Val | Arg | GTC | CGC |
| 38 | α-6th | Leu | Thr | CTG | ACG |
| | α-19th | Ala | Val | GCG | GTG |
| | α-126th | Phe | Tyr | TTC | TAC |
| | β-48th | Leu | Val | CTG | GTG |
| | β-108th | Glu | Arg | GAG | CGG |
| | β-212th | Ser | Tyr | TCC | TAC | described in the above Reference Example 18 was used as the template, and the primer having the sequence defined in SEQ ID No: 34 in the Sequence Listing was used for carrying out the method using the mutagenesis kit described in Reference Example 2, whereby a plasmid (40) encoding the above nitrile hydratase variant was prepared. A competent cell of *Escherichia coli* HB101 (manufactured by Toyobo Co., Ltd.) was transformed with the plasmid to obtain a transformant (40). Moreover, the plasmid was prepared from the above-mentioned microbial cells by the alkaline SDS extraction method, and the base sequence of the nitrile hydratase gene was determined using a DNA sequencer. Then, it was confirmed that the transformant (40) had sequences according to the purpose in which mutation of 96th Gln in the β-subunit with Arg was newly added to the plasmid (37) of Reference Example 18. In the production of an amide compound using the thus obtained transformant (40) and the transformant (37) to be its base, the initial reaction rate and thermal stability were compared in the same manner as in Example 1.

As a result, it was found that mutation of 96th Gln in the β-subunit with Arg was newly added to the transformant (40), so that the initial reaction rate was improved by 1.25 times and thermal stability was improved by 1.36 times, as compared to those of the transformant (37).

Example 19

Construction of a Transformant (41) Substituted Amino Acid Having Improved Nitrile Hydratase Activity and Improved Thermal Stability In order to obtain a transformant (41) expressing the nitrile hydratase variant obtained by mutating nitrile hydratase at (g) and (aq) amino acid substitution sites as shown in Table 15, the plasmid (38) recovered from the transformant (38) described in the above Reference Example 19 was used as the template, and the primer having the sequence defined in SEQ ID No: 34 in the Sequence Listing was used for carrying out the method using the mutagenesis kit described in Reference Example 2, whereby a plasmid (41) encoding the above nitrile hydratase variant was prepared. A competent cell of *Escherichia coli* HB101 (manufactured by Toyobo Co., Ltd.) was transformed with the plasmid to obtain a transformant (41). Moreover, the plasmid was prepared from the above-mentioned microbial cells by the alkaline SDS extraction method, and the base sequence of the nitrile hydratase gene was determined using a DNA sequencer. Then, it was confirmed that the transformant (41) had sequences according to the purpose in which mutation of 96th Gln in the β-subunit with Arg was newly added to the plasmid (38) of Reference Example 19. In the production of an amide compound using the thus obtained transformant (41) and the transformant (38) to be its base, the initial reaction rate and thermal stability were compared in the same manner as in Example 1.

As a result, it was found that mutation of 96th Gln in the β-subunit with Arg was newly added to the transformant (41), so that the initial reaction rate was improved by 1.35 times and thermal stability was improved by 1.42 times, as compared to those of the transformant (38).

TABLE 28

(Table 15)

| Trans-formant No. | Mutated Site | Change in Amino Acid Sequence | | Change in Base Sequence | | Improvement of Reaction Rate by β-96th Substitution | Improvement of Thermal Stability by β-96th Substitution |
|---|---|---|---|---|---|---|---|
| | | Before Substitution | After Substitution | Before Substitution | After Substitution | | |
| 39 | α-36th | Thr | Met | ACG | ATG | 1.33 times | 1.25 times |
| | α-126th | Phe | Tyr | TTC | TAC | | |
| | β-96th | Gln | Arg | CAG | CGT | | |
| 40 | α-36th | Thr | Met | ACG | ATG | 1.25 times | 1.36 times |
| | α-148th | Gly | Asp | GGC | GAC | | |
| | α-204th | Val | Arg | GTC | CGC | | |
| | β-96th | Gln | Arg | CAG | CGT | | |
| 41 | α-6th | Leu | Thr | CTG | ACG | 1.35 times | 1.42 times |
| | α-19th | Ala | Val | GCG | GTG | | |
| | α-126th | Phe | Tyr | TTC | TAC | | |
| | β-48th | Leu | Val | CTG | GTG | | |
| | β-96th | Gln | Arg | CAG | CGT | | |
| | β-108th | Glu | Arg | GAG | CGG | | |
| | β-212th | Ser | Tyr | TCC | TAC | | |

Reference Example 20

Construction of a Transformant (42) Substituted Amino Acid Having Nitrile Hydratase Activity In order to obtain a transformant (42) expressing the nitrile hydratase variant obtained by mutating nitrile hydratase at (ae) amino acid substitution sites as shown in Table 16, the plasma described in Example 62 of Patent Document 2 was used as the template, and the ribosome binding sequence was modified according to the method described in Example 1 to prepare a plasmid (42) encoding the above nitrile hydratase variant. A competent cell of *Escherichia coli* HB101 (manufactured by Toyobo Co., Ltd.) was transformed with the plasmid to obtain a transformant (42).

Reference Example 21

Construction of a Transformant (43) Substituted Amino Acid Having Nitrile Hydratase Activity In order to obtain a transformant (43) expressing the nitrile hydratase variant obtained by mutating nitrile hydratase at (bk) amino acid substitution sites as shown in Table 16, introduction of site-specific mutation was performed using the mutagenesis kit described in the above Reference Example 2.

The plasmid (1) expressing nitrile hydratase with the modified ribosome binding sequence described in Example 1 was used as the template, and the primers having the sequence defined in SEQ ID Nos: 35 and 36 in the Sequence Listing were used for repeatedly carrying out the method described in Reference Example 2 per mutation point, whereby a plasmid (43) encoding the above nitrile hydratase variant was prepared. A competent cell of *Escherichia coli* HB101 (manufactured by Toyobo Co., Ltd.) was transformed with the plasmid to obtain a transformant (43).

TABLE 29

(Table 16)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 42 | β-160th | Arg | Trp | CGG | TGG |
| | β-186th | Leu | Arg | CTG | CGG |
| 43 | β-61st | Ala | Trp | GCC | TGG |
| | β-217th | Asp | His | GAC | CAC |

Example 20

Construction of a Transformant (44) Substituted Amino Acid Having Improved Nitrile Hydratase Activity and Improved Thermal Stability In order to obtain a transformant (44) expressing the nitrile hydratase variant obtained by mutating nitrile hydratase at (h) and (ae) amino acid substitution sites as shown in Table 17, the plasmid (42) recovered from the transformant (42) described in the above Reference Example 20 was used as the template, and the primer having the sequence defined in SEQ ID No: 37 in the Sequence Listing was used for carrying out the method using the mutagenesis kit described in Reference Example 2, whereby a plasmid (44) encoding the above nitrile hydratase variant was prepared. A competent cell of *Escherichia coli* HB101 (manufactured by Toyobo Co., Ltd.) was transformed with the plasmid to obtain a transformant (44). Moreover, the plasmid was prepared from the above-mentioned microbial cells by the alkaline SDS extraction method, and the base sequence of the nitrile hydratase gene was determined using a DNA sequencer. Then, it was confirmed that the transformant (44) had sequences according to the purpose in which mutation of 107th Pro in the β-subunit with Met was newly added to the plasmid (42) of Reference Example 20. In the production of an amide compound using the thus obtained transformant (44) and the transformant (42) to be its base, the initial reaction rate and thermal stability were compared in the same manner as in Example 1.

As a result, it was found that mutation of 107th Pro in the β-subunit with Met was newly added to the transformant (44), so that the initial reaction rate was improved by 1.34 times and thermal stability was improved by 2.25 times, as compared to those of the transformant (42).

Example 21

Construction (45) of a Transformant (45) Substituted Amino Acid Having Improved Nitrile Hydratase Activity and Improved Thermal Stability In order to obtain a transformant (45) expressing the nitrile hydratase variant obtained by mutating nitrile hydratase at (h) and (au) amino acid substitution sites as shown in Table 17, the plasmid (31) recovered from the transformant (31) described in the above Reference Example 15 was used as the template, and the primer having the sequence defined in SEQ ID No: 68 in the Sequence Listing was used for carrying out the method using the mutagenesis kit described in Reference Example 2, whereby a plasmid (45) encoding the above nitrile hydratase variant was prepared. A competent cell of *Escherichia coli* HB101 (manufactured by Toyobo Co., Ltd.) was transformed with the plasmid to obtain a transformant (45). Moreover, the plasmid was prepared from the above-mentioned microbial cells by the alkaline SDS extraction method, and the base sequence of the nitrile hydratase gene was determined using a DNA sequencer. Then, it was confirmed that the transformant (45) had sequences according to the purpose in which mutation of 107th Pro in the β-subunit with Met was newly added to the plasmid (31) of Reference Example 15. In the production of an amide compound using the thus obtained transformant (45) and the transformant (31) to be its base, the initial reaction rate and thermal stability were compared in the same manner as in Example 1.

As a result, it was found that mutation of 107th Pro in the β-subunit with Met was newly added to the transformant (45), so that the initial reaction rate was improved by 1.40 times and thermal stability was improved by 2.12 times, as compared to those of the transformant (31).

Example 22

Construction of a Transformant (46) Substituted Amino Acid Having Improved Nitrile Hydratase Activity and Improved Thermal Stability In order to obtain a transformant (46) expressing the nitrile hydratase variant obtained by mutating nitrile hydratase at (h) and (bk) amino acid substitution sites as shown in Table 17, the plasmid (43) recovered from the transformant (43) described in the above Reference Example 21 was used as the template, and the primer having the sequence defined in SEQ ID No: 37 in the Sequence Listing was used for carrying out the method using the mutagenesis kit described in Reference Example 2, whereby a plasmid (46) encoding the above nitrile hydratase variant was prepared. A competent cell of *Escherichia coli* HB101 (manufactured by Toyobo Co., Ltd.) was transformed with the plasmid to obtain a transformant (46). Moreover, the plasmid was prepared from the above-mentioned microbial cells by the alkaline SDS extraction method, and the base sequence of the nitrile hydratase gene was determined using a DNA sequencer. Then, it was confirmed that the transformant (46) had sequences according to the purpose in which mutation of 107th Pro in the β-subunit with Met was newly added to the plasmid (43) of Reference Example 21. In the production of an amide compound using the thus obtained transformant (46) and the transformant (43)

to be its base, the initial reaction rate and thermal stability were compared in the same manner as in Example 1.

As a result, it was found that mutation of 107th Pro in the β-subunit with Met was newly added to the transformant (46), so that the initial reaction rate was improved by 1.32 times and thermal stability was improved by 2.40 times, as compared to those of the transformant (43).

TABLE 30

(Table 17)

| Trans-formant No. | Mutated Site | Change in Amino Acid Sequence | | Change in Base Sequence | | Improvement of Reaction Rate by β-107th Substitution | Improvement of Thermal Stability by β-107th Substitution |
|---|---|---|---|---|---|---|---|
| | | Before Substi-tution | After Substi-tution | Before Substi-tution | After Substi-tution | | |
| 44 | β-107th | Pro | Met | CCC | ATG | 1.34 times | 2.25 times |
| | β-160th | Arg | Trp | CGG | TGG | | |
| | β-186th | Leu | Arg | CTG | CGG | | |
| 45 | α-19th | Ala | Val | GCG | GTG | 1.40 times | 2.12 times |
| | α-71st | Arg | His | CGT | CAT | | |
| | α-126th | Phe | Tyr | TTC | TAC | | |
| | β-37th | Phe | Val | TTC | GTC | | |
| | β-107th | Pro | Met | CCC | ATG | | |
| | β-108th | Glu | Asp | GAG | GAT | | |
| | β-200th | Ala | Glu | GCC | GAG | | |
| 46 | β-61st | Ala | Trp | GCC | TGG | 1.32 times | 2.40 times |
| | β-107th | Pro | Met | CCC | ATG | | |
| | β-217th | Asp | His | GAC | CAC | | |

Example 23

Construction of a Transformant (47) Substituted Amino Acid Having Improved Nitrile Hydratase Activity and Improved Thermal Stability In order to obtain a transformant (47) expressing the nitrile hydratase variant obtained by mutating nitrile hydratase at (i) and (aa) amino acid substitution sites as shown in Table 18, the plasmid (36) recovered from the transformant (36) described in the above Reference Example 17 was used as the template, and the primer having the sequence defined in SEQ ID No: 38 in the Sequence Listing was used for carrying out the method using the mutagenesis kit described in Reference Example 2, whereby a plasmid (47) encoding the above nitrile hydratase variant was prepared. A competent cell of *Escherichia coli* HB101 (manufactured by Toyobo Co., Ltd.) was transformed with the plasmid to obtain a transformant (47). Moreover, the plasmid was prepared from the above-mentioned microbial cells by the alkaline SDS extraction method, and the base sequence of the nitrile hydratase gene was determined using a DNA sequencer. Then, it was confirmed that the transformant (47) had sequences according to the purpose in which mutation of 226th Val in the β-subunit with Ile was newly added to the plasmid (36) of Reference Example 17. In the production of an amide compound using the thus obtained transformant (47) and the transformant (36) to be its base, the initial reaction rate and thermal stability were compared in the same manner as in Example 1.

As a result, it was found that mutation of 226th Val in the β-subunit with Ile was newly added to the transformant (47), so that the initial reaction rate was improved by 1.26 times and thermal stability was improved by 1.29 times, as compared to those of the transformant (36).

Example 24

Construction (48) of a Transformant (48) Substituted Amino Acid Having Improved Nitrile Hydratase Activity and Improved Thermal Stability In order to obtain a transformant (48) expressing the nitrile hydratase variant obtained by mutating nitrile hydratase at (i) and (ak) amino acid substitution sites as shown in Table 18, the plasmid (8) recovered from the transformant (8) described in the above Reference Example 4 was used as the template, and the primer having the sequence defined in SEQ ID No: 38 in the Sequence Listing was used for carrying out the method using the mutagenesis kit described in Reference Example 2, whereby a plasmid (48) encoding the above nitrile hydratase variant was prepared. A competent cell of *Escherichia coli* HB101 (manufactured by Toyobo Co., Ltd.) was transformed with the plasmid to obtain a transformant (48). Moreover, the plasmid was prepared from the above-mentioned microbial cells by the alkaline SDS extraction method, and the base sequence of the nitrile hydratase gene was determined using a DNA sequencer. Then, it was confirmed that the transformant (48) had sequences according to the purpose in which mutation of 226th Val in the β-subunit with Ile was newly added to the plasmid (8) of Reference Example 4. In the production of an amide compound using the thus obtained transformant (48) and the transformant (8) to be its base, the initial reaction rate and thermal stability were compared in the same manner as in Example 1.

As a result, it was found that mutation of 226th Val in the β-subunit with Ile was newly added to the transformant (48), so that the initial reaction rate was improved by 1.35 times and thermal stability was improved by 1.27 times, as compared to those of the transformant (8).

Example 25

Construction of a Transformant (49) Substituted Amino Acid Having Improved Nitrile Hydratase Activity and Improved Thermal Stability In order to obtain a transformant (49) expressing the nitrile hydratase variant obtained by mutating nitrile hydratase at (i) and (be) amino acid substitution sites as shown in Table 18, the plasmid (15) recovered from the transformant (15)

described in the above Reference Example 8 was used as the template, and the primer having the sequence defined in SEQ ID No: 38 in the Sequence Listing was used for carrying out the method using the mutagenesis kit described in Reference Example 2, whereby a plasmid (49) encoding the above nitrile hydratase variant was prepared. A competent cell of *Escherichia coli* HB101 (manufactured by Toyobo Co., Ltd.) was transformed with the plasmid to obtain a transformant (49). Moreover, the plasmid was prepared from the above-mentioned microbial cells by the alkaline SDS extraction method, and the base sequence of the nitrile hydratase gene was determined using a DNA sequencer. Then, it was confirmed that the transformant (49) had sequences according to the purpose in which mutation of 226th Val in the β-subunit with Ile was newly added to the plasmid (15) of Reference Example 8. In the production of an amide compound using the thus obtained transformant (49) and the transformant (15) to be its base, the initial reaction rate and thermal stability were compared in the same manner as in Example 1.

As a result, it was found that mutation of 226th Val in the β-subunit with Ile was newly added to the transformant (49), so that the initial reaction rate was improved by 1.25 times and thermal stability was improved by 1.30 times, as compared to those of the transformant (15).

Reference Example 22

Construction of a Transformant (50) Substituted Amino Acid Having Nitrile Hydratase Activity In order to obtain a transformant (50) expressing the nitrile hydratase variant obtained by mutating nitrile hydratase at (af) amino acid substitution sites as shown in Table 19, the plasma described in Example 63 of Patent Document 2 was used as the template, and the ribosome binding sequence was modified according to the method described in Example 1 to prepare a plasmid (50) encoding the above nitrile hydratase variant. A competent cell of *Escherichia coli* HB101 (manufactured by Toyobo Co., Ltd.) was transformed with the plasmid to obtain a transformant (50).

Reference Example 23

Construction of a Transformant (51) Substituted Amino Acid Having Nitrile Hydratase Activity In order to obtain a plasmid encoding the nitrile hydratase variant obtained by mutating nitrile hydratase at (bq) amino acid substitution sites as shown in Table 19, introduction of site-specific mutation was performed using the mutagenesis kit described in the above Reference Example 2. The plasmid (1) expressing nitrile hydratase with the modified ribosome binding sequence described in Example 1 was used as the template, the primers having the sequence defined in SEQ ID Nos: 39 and 40 in the Sequence Listing were used for repeatedly carrying out the method described in Reference Example 2 per mutation point, whereby a plasmid (51) encoding the above nitrile hydratase variant was prepared. A competent cell of *Escherichia coli* HB101 (manufactured by Toyobo Co., Ltd.) was transformed with the plasmid to obtain a transformant (51).

Reference Example 24

Construction of a Transformant (52) Substituted Amino Acid Having Nitrile Hydratase Activity

TABLE 31

(Table 18)

| Transformant No. | Mutated Site | Change in Amino Acid Sequence Before Substitution | Change in Amino Acid Sequence After Substitution | Change in Base Sequence Before Substitution | Change in Base Sequence After Substitution | Improvement of Reaction Rate by β-226th Substitution | Improvement of Thermal Stability by β-226th Substitution |
|---|---|---|---|---|---|---|---|
| 47 | α-36th | Thr | Met | ACG | ATG | 1.26 times | 1.29 times |
|  | α-126th | Phe | Tyr | TTC | TAC |  |  |
|  | β-226th | Val | Ile | GTC | ATC |  |  |
| 48 | β-37th | Phe | Val | TTC | GTC | 1.35 times | 1.27 times |
|  | β-108th | Glu | Asp | GAG | GAT |  |  |
|  | β-200th | Ala | Glu | GCC | GAG |  |  |
|  | β-226th | Val | Ile | GTC | ATC |  |  |
| 49 | β-40th | Thr | Val | ACG | GTG | 1.25 times | 1.30 times |
|  | β-218th | Cys | Met | TGC | ATG |  |  |
|  | β-226th | Val | Ile | GTC | ATC |  |  |

In order to obtain a transformant (52) expressing the nitrile hydratase variant obtained by mutating nitrile hydratase at (bj) amino acid substitution sites as shown in Table 19, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 41 and 42 in the Sequence Listing were used for repeatedly carrying out the method described in Reference Example 2 per mutation point, whereby a plasmid (52) encoding the above nitrile hydratase variant was prepared. A competent cell of *Escherichia coli* HB101 (manufactured by Toyobo Co., Ltd.) was transformed with the plasmid to obtain a transformant (52).

TABLE 32

(Table 19)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 50 | α-6th | Leu | Thr | CTG | ACG |
| | α-36th | Thr | Met | ACG | ATG |
| | α-126th | Phe | Tyr | TTC | TAC |
| 51 | β-61st | Ala | Ser | GCC | TCG |
| | β-160th | Arg | Met | CGG | ATG |
| 52 | β-112th | Lys | Val | AAG | GTG |
| | β-217th | Asp | Met | GAC | ATG |

Example 26

Construction of a Transformant (53) Substituted Amino Acid Having Improved Nitrile Hydratase Activity and Improved Thermal Stability In order to obtain a transformant (53) expressing the nitrile hydratase variant obtained by mutating nitrile hydratase at (m-1) and (af) amino acid substitution sites as shown in Table 20, the plasmid (50) recovered from the transformant (50) described in the above Reference Example 22 was used as the template, and the primers having the sequence defined in SEQ ID Nos: 43 and 19 in the Sequence Listing were used for repeatedly carrying out the method described in Reference Example 2 per mutation point, whereby a plasmid (53) encoding the above nitrile hydratase variant was prepared. A competent cell of *Escherichia coli* HB101 (manufactured by Toyobo Co., Ltd.) was transformed with the plasmid to obtain a transformant (53). Moreover, the plasmid was prepared from the above-mentioned microbial cells by the alkaline SDS extraction method, and the base sequence of the nitrile hydratase gene was determined using a DNA sequencer. Then, it was confirmed that the transformant (53) had sequences according to the purpose in which mutation of 13th Ile in the α-subunit with Leu and mutation of 94th Met in the α-subunit with Ile were newly added to the plasmid (50) of Reference Example 22. In the production of an amide compound using the thus obtained transformant (53) and the transformant (50) to be its base, the initial reaction rate and thermal stability were compared in the same manner as in Example 1.

As a result, it was found that mutation of 13th Ile in the α-subunit with Leu and mutation of 94th Met in the α-subunit with Ile were newly added to the transformant (53), so that the initial reaction rate was improved by 1.67 times and thermal stability was improved by 1.45 times, as compared to those of the transformant (50).

Example 27

Construction of a Transformant (54) Substituted Amino Acid Having Improved Nitrile Hydratase Activity and Improved Thermal Stability In order to obtain a transformant (54) expressing the nitrile hydratase variant obtained by mutating nitrile hydratase at (m-1) and (bq) amino acid substitution sites as shown in Table 20, the plasmid (51) recovered from the transformant (51) described in the above Reference Example 23 was used as the template, and the primers having the sequence defined in SEQ ID Nos: 43 and 19 in the Sequence Listing were used for repeatedly carrying out the method described in Reference Example 2 per mutation point, whereby a plasmid (54) encoding the above nitrile hydratase variant was prepared. A competent cell of *Escherichia coli* HB101 (manufactured by Toyobo Co., Ltd.) was transformed with the plasmid to obtain a transformant (54). Moreover, the plasmid was prepared from the above-mentioned microbial cells by the alkaline SDS extraction method, and the base sequence of the nitrile hydratase gene was determined using a DNA sequencer. Then, it was confirmed that the transformant (54) had sequences according to the purpose in which mutation of 13th Ile in the α-subunit with Leu and mutation of 94th Met in the α-subunit with Ile were newly added to the plasmid (51) of Reference Example 23. In the production of an amide compound using the thus obtained transformant (54) and the transformant (51) to be its base, the initial reaction rate and thermal stability were compared in the same manner as in Example 1.

As a result, it was found that mutation of 13th Ile in the α-subunit with Leu and mutation of 94th Met in the α-subunit with Ile were newly added to the transformant (54), so that the initial reaction rate was improved by 1.59 times and thermal stability was improved by 1.32 times, as compared to those of the transformant (51).

Example 28

Construction of a Transformant (55) Substituted Amino Acid Having Improved Nitrile Hydratase Activity and Improved Thermal Stability In order to obtain a transformant (55) expressing the nitrile hydratase variant obtained by mutating nitrile hydratase at (m-1) and (bj) amino acid substitution sites as shown in Table 20, the plasmid (52) recovered from the transformant (52) described in the above Reference Example 24 was used as the template, and the primers having the sequence defined in SEQ ID Nos: 43 and 19 in the Sequence Listing were used for repeatedly carrying out the method described in Reference Example 2 per mutation point, whereby a plasmid (55) encoding the above nitrile hydratase variant was prepared. A competent cell of *Escherichia coli* HB101 (manufactured by Toyobo Co., Ltd.) was transformed with the plasmid to obtain a transformant (55). Moreover, the plasmid was prepared from the above-mentioned microbial cells by the alkaline SDS extraction method, and the base sequence of the nitrile hydratase gene was determined using a DNA sequencer. Then, it was confirmed that the transformant (55) had sequences according to the purpose in which mutation of 13th Ile in the α-subunit with Leu and mutation of 94th Met in the α-subunit with Ile were newly added to the plasmid (52) of Reference Example 24. In the production of an amide compound using the thus obtained transformant (55) and the transformant (52) to be its base, the initial reaction rate and thermal stability were compared in the same manner as in Example 1.

As a result, it was found that mutation of 13th Ile in the α-subunit with Leu and mutation of 94th Met in the α-subunit with Ile were newly added to the transformant (55), so that the initial reaction rate was improved by 1.62 times and thermal stability was improved by 1.26 times, as compared to those of the transformant (52).

TABLE 33

(Table 20)

| Trans-formant No. | Mutated Site | Change in Amino Acid Sequence | | Change in Base Sequence | | Improvement of Reaction Rate by and α-226th Substitution | Improvement of Thermal Stability by 13th and α-94th Substitution |
|---|---|---|---|---|---|---|---|
| | | Before Substitution | After Substitution | Before Substitution | After Substitution | | |
| 53 | α-6th | Leu | Thr | CTG | ACG | 1.67 times | 1.45 times |
| | α-13th | Ile | Leu | ATC | CTC | | |
| | α-36th | Thr | Met | ACG | ATG | | |
| | α-94th | Met | Ile | ATG | ATC | | |
| | α-126th | Phe | Tyr | TTC | TAC | | |
| 54 | α-13th | Ile | Leu | ATC | CTC | 1.59 times | 1.32 times |
| | α-94th | Met | Ile | ATG | ATC | | |
| | β-61st | Ala | Ser | GCC | TCG | | |
| | β-160th | Arg | Met | CGG | ATG | | |
| 55 | α-13th | Ile | Leu | ATC | CTC | 1.62 times | 1.26 times |
| | α-94th | Met | Ile | ATG | ATC | | |
| | β-112th | Lys | Val | AAG | GTG | | |
| | β-217th | Asp | Met | GAC | ATG | | |

Reference Example 25

Construction of a Transformant (56) Substituted Amino Acid Having Nitrile Hydratase Activity In order to obtain a transformant (56) expressing the nitrile hydratase variant obtained by mutating nitrile hydratase at (am) amino acid substitution sites as shown in Table 21, the plasma described in Example 70 of Patent Document 2 was used as the template, and the ribosome binding sequence was modified according to the method described in Example 1 to prepare a plasmid (56) encoding the above nitrile hydratase variant. A competent cell of *Escherichia coli* HB101 (manufactured by Toyobo Co., Ltd.) was transformed with the plasmid to obtain a transformant (56).

Reference Example 26

Construction of a Transformant (57) Substituted Amino Acid Having Nitrile Hydratase Activity In order to obtain a transformant (57) expressing the nitrile hydratase variant obtained by mutating nitrile hydratase at (ay) amino acid substitution sites as shown in Table 21, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 44 and 45 in the Sequence Listing were used for repeatedly carrying out the method described in Reference Example 2 per mutation point, whereby a plasmid (57) encoding the above nitrile hydratase variant was prepared. A competent cell of *Escherichia coli* HB101 (manufactured by Toyobo Co., Ltd.) was transformed with the plasmid to obtain a transformant (57).

TABLE 34

(Table 21)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 56 | β-46th | Met | Lys | ATG | AAG |
| | β-108th | Glu | Arg | GAG | CGG |
| | β-212th | Ser | Tyr | TCC | TAC |
| 57 | α-36th | Thr | Ala | ACG | GCG |
| | α-48th | Asn | Gln | AAC | CAA |

Example 29

Construction of a Transformant (58) Substituted Amino Acid Having Improved Nitrile Hydratase Activity and Improved Thermal Stability In order to obtain a transformant (58) expressing the nitrile hydratase variant obtained by mutating nitrile hydratase at (m-2) and (am) amino acid substitution sites as shown in Table 22, the plasmid (56) recovered from the transformant (56) described in the above Reference Example 25 was used as the template, and the primers having the sequence defined in SEQ ID Nos: 43 and 34 in the Sequence Listing were used for repeatedly carrying out the method described in Reference Example 2 per mutation point, whereby a plasmid (58) encoding the above nitrile hydratase variant was prepared. A competent cell of *Escherichia coli* HB101 (manufactured by Toyobo Co., Ltd.) was transformed with the plasmid to obtain a transformant (58). Moreover, the plasmid was prepared from the above-mentioned microbial cells by the alkaline SDS extraction method, and the base sequence of the nitrile hydratase gene was determined using a DNA sequencer. Then, it was confirmed that the transformant (56) had sequences according to the purpose in which mutation of 13th Ile in the α-subunit with Leu and mutation of 96th Gln in the β-subunit with Arg were newly added to the plasmid (56) of Reference Example 25. In the production of an amide compound using the thus obtained transformant (58) and the transformant (56) to be its base, the initial reaction rate and thermal stability were compared in the same manner as in Example 1.

As a result, it was found that mutation of 13th Ile in the α-subunit with Leu and mutation of 96th Gln in the β-subunit with Arg were newly added to the transformant (58), so that the initial reaction rate was improved by 1.53 times and thermal stability was improved by 1.32 times, as compared to those of the transformant (56).

Example 30

Construction of a Transformant (59) Substituted Amino Acid Having Improved Nitrile Hydratase Activity and Improved Thermal Stability In order to obtain a transformant (59) expressing the nitrile hydratase variant obtained by mutating nitrile hydratase at (m-2) and (at) amino acid substitution sites as shown in Table 22, the plasmid (27) recovered from the transformant (27) described in the above Reference Example 14 was used as the template, and the primers having the sequence defined in SEQ ID Nos: 43 and 34 in the Sequence Listing were used for repeatedly carrying out the method described in Reference Example 2 per mutation point, whereby a plasmid (59) encoding the above nitrile hydratase variant was prepared. A competent cell of *Escherichia coli* HB101 (manufactured by Toyobo Co., Ltd.) was transformed with the plasmid to obtain a transformant (59). Moreover, the plasmid was prepared from the above-mentioned microbial cells by the alkaline SDS extraction method, and the base sequence of the nitrile hydratase gene was determined using a DNA sequencer. Then, it was confirmed that the transformant (59) had sequences according to the purpose in which mutation of 13th Ile in the α-subunit with Leu and mutation of 96th Gln in the β-subunit with Arg were newly added to the plasmid (27) of Reference Example 14. In the production of an amide compound using the thus obtained transformant (59) and the transformant (27) to be its base, the initial reaction rate and thermal stability were compared in the same manner as in Example 1.

As a result, it was found that mutation of 13th Ile in the α-subunit with Leu and mutation of 96th Gln in the β-subunit with Arg were newly added to the transformant (59), so that the initial reaction rate was improved by 1.49 times and thermal stability was improved by 1.28 times, as compared to those of the transformant (27).

Example 31

Construction of a Transformant (60) Substituted Amino Acid Having Improved Nitrile Hydratase Activity and Improved Thermal Stability In order to obtain a transformant (60) expressing the nitrile hydratase variant obtained by mutating nitrile hydratase at (m-2) and (ay) amino acid substitution sites as shown in Table 22, the plasmid (57) recovered from the transformant (57) described in the above Reference Example 26 was used as the template, and the primers having the sequence defined in SEQ ID Nos: 43 and 34 in the Sequence Listing were used for repeatedly carrying out the method described in Reference Example 2 per mutation point, whereby a plasmid (60) encoding the above nitrile hydratase variant was prepared. A competent cell of *Escherichia coli* HB101 (manufactured by Toyobo Co., Ltd.) was transformed with the plasmid to obtain a transformant (60). Moreover, the plasmid was prepared from the above-mentioned microbial cells by the alkaline SDS extraction method, and the base sequence of the nitrile hydratase gene was determined using a DNA sequencer. Then, it was confirmed that the transformant (60) had sequences according to the purpose in which mutation of 13th Ile in the α-subunit with Leu and mutation of 96th Gln in the β-subunit with Arg were newly added to the plasmid (57) of Reference Example 26. In the production of an amide compound using the thus obtained transformant (60) and the transformant (57) to be its base, the initial reaction rate and thermal stability were compared in the same manner as in Example 1.

As a result, it was found that mutation of 13th Ile in the α-subunit with Leu and mutation of 96th Gln in the β-subunit with Arg were newly added to the transformant (60), so that the initial reaction rate was improved by 1.39 times and thermal stability was improved by 1.45 times, as compared to those of the transformant (57).

transformant (50) to be its base, the initial reaction rate and thermal stability were compared in the same manner as in Example 1.

As a result, it was found that mutation of 27th Met in the α-subunit with Ile and mutation of 94th Met in the α-subunit with Ile were newly added to the transformant (61), so that the initial reaction rate was improved by 1.65 times and thermal stability was improved by 1.36 times, as compared to those of the transformant (50).

TABLE 35

(Table 22)

| Trans-formant No. | Mutated Site | Change in Amino Acid Sequence | | Change in Base Sequence | | Improvement of Reaction Rate by α-13th and β-226th Substitution | Improvement of Thermal Stability by α-13th and β-226th Substitution |
|---|---|---|---|---|---|---|---|
| | | Before Substi-tution | After Substi-tution | Before Substi-tution | After Substi-tution | | |
| 58 | α-13th | Ile | Leu | ATC | CTC | 1.53 times | 1.32 times |
| | β-46th | Met | Lys | ATG | AAG | | |
| | β-96th | Gln | Arg | CAG | CGT | | |
| | β-108th | Glu | Arg | GAG | CGG | | |
| | β-212th | Ser | Tyr | TCC | TAC | | |
| 59 | α-13th | Ile | Leu | ATC | CTC | 1.49 times | 1.28 times |
| | α-19th | Ala | Val | GCG | GTG | | |
| | α-71st | Arg | His | CGT | CAT | | |
| | α-126th | Phe | Tyr | TTC | TAC | | |
| | β-37th | Phe | Leu | TTC | CTC | | |
| | β-96th | Gln | Arg | CAG | CGT | | |
| | β-108th | Glu | Asp | GAG | GAT | | |
| | β-200th | Ala | Glu | GCC | GAG | | |
| 60 | α-13th | Ile | Leu | ATC | CTC | 1.39 times | 1.45 times |
| | α-36th | Thr | Ala | ACG | GCG | | |
| | α-48th | Asn | Gln | AAC | CAA | | |
| | β-96th | Gln | Arg | CAG | CGT | | |

Example 32

Construction of a Transformant (61) Substituted Amino Acid Having Improved Nitrile Hydratase Activity and Improved Thermal Stability In order to obtain a transformant (61) expressing the nitrile hydratase variant obtained by mutating nitrile hydratase at (n−1) and (af) amino acid substitution sites as shown in Table 23, the plasmid (50) recovered from the transformant (50) described in the above Reference Example 22 was used as the template, and the primers having the sequence defined in SEQ ID Nos: 46 and 19 in the Sequence Listing were used for repeatedly carrying out the method described in Reference Example 2 per mutation point, whereby a plasmid (61) encoding the above nitrile hydratase variant was prepared. A competent cell of Escherichia coli HB101 (manufactured by Toyobo Co., Ltd.) was transformed with the plasmid to obtain a transformant (61). Moreover, the plasmid was prepared from the above-mentioned microbial cells by the alkaline SDS extraction method, and the base sequence of the nitrile hydratase gene was determined using a DNA sequencer. Then, it was confirmed that the transformant (61) had sequences according to the purpose in which mutation of 27th Met in the α-subunit with Ile and mutation of 94th Met in the α-subunit with Ile were newly added to the plasmid (50) of Reference Example 22. In the production of an amide compound using the thus obtained transformant (61) and the Example 33

Construction of a Transformant (62) Substituted Amino Acid Having Improved Nitrile Hydratase Activity and Improved Thermal Stability In order to obtain a transformant (62) expressing the nitrile hydratase variant obtained by mutating nitrile hydratase at (n−1) and (ao) amino acid substitution sites as shown in Table 23, the plasmid (26) recovered from the transformant (26) described in the above Reference Example 13 was used as the template, and the primers having the sequence defined in SEQ ID Nos: 46 and 19 in the Sequence Listing were used for repeatedly carrying out the method described in Reference Example 2 per mutation point, whereby a plasmid (62) encoding the above nitrile hydratase variant was prepared. A competent cell of Escherichia coli HB101 (manufactured by Toyobo Co., Ltd.) was transformed with the plasmid to obtain a transformant (62). Moreover, the plasmid was prepared from the above-mentioned microbial cells by the alkaline SDS extraction method, and the base sequence of the nitrile hydratase gene was determined using a DNA sequencer. Then, it was confirmed that the transformant (62) had sequences according to the purpose in which mutation of 27th Met in the α-subunit with Ile and mutation of 94th Met in the α-subunit with Ile were newly added to the plasmid (26) of Reference Example 13. In the production of an amide compound using the thus obtained transformant (62) and the transformant (26) to be its base, the initial reaction rate and thermal stability were compared in the same manner as in Example 1.

As a result, it was found that mutation of 27th Met in the α-subunit with Ile and mutation of 94th Met in the α-subunit with Ile were newly added to the transformant (62), so that the initial reaction rate was improved by 1.72 times and thermal stability was improved by 1.47 times, as compared to those of the transformant (26).

Example 34

Construction of a Transformant (63) Substituted Amino Acid Having Improved Nitrile Hydratase Activity and Improved Thermal Stability In order to obtain a transformant (63) expressing the nitrile hydratase variant obtained by mutating nitrile hydratase at (n–1) and (ax) amino acid substitution sites as shown in Table 23, the plasmid (21) recovered from the transformant (21) described in the above Reference Example 11 was used as the template, and the primers having the sequence defined in SEQ ID Nos: 46 and 19 in the Sequence Listing were used for repeatedly carrying out the method described in Reference Example 2 per mutation point, whereby a plasmid (63) encoding the above nitrile hydratase variant was prepared. A competent cell of *Escherichia coli* HB101 (manufactured by Toyobo Co., Ltd.) was transformed with the plasmid to obtain a transformant (63). Moreover, the plasmid was prepared from the above-mentioned microbial cells by the alkaline SDS extraction method, and the base sequence of the nitrile hydratase gene was determined using a DNA sequencer. Then, it was confirmed that the transformant (63) had sequences according to the purpose in which mutation of 27th Met in the α-subunit with Ile and mutation of 94th Met in the α-subunit with Ile were newly added to the plasmid (21) of Reference Example 11. In the production of an amide compound using the thus obtained transformant (63) and the transformant (21) to be its base, the initial reaction rate and thermal stability were compared in the same manner as in Example 1.

As a result, it was found that mutation of 27th Met in the α-subunit with Ile and mutation of 94th Met in the α-subunit with Ile were newly added to the transformant (63), so that the initial reaction rate was improved by 1.55 times and thermal stability was improved by 1.27 times, as compared to those of the transformant (21).

TABLE 36

(Table 23)

| Transformant No. | Mutated Site | Change in Amino Acid Sequence | | Change in Base Sequence | | Improvement of Reaction Rate by α-27th and α-94th Substitution | Improvement of Thermal Stability by α-27th and α-94th Substitution |
|---|---|---|---|---|---|---|---|
| | | Before Substitution | After Substitution | Before Substitution | After Substitution | | |
| 61 | α-6th | Leu | Thr | CTG | ACG | 1.65 times | 1.36 times |
| | α-27th | Met | Ile | ATG | ATC | | |
| | α-36th | Thr | Met | ACG | ATG | | |
| | α-94th | Met | Ile | ATG | ATC | | |
| | α-126th | Phe | Tyr | TTC | TAC | | |
| 62 | α-27th | Met | Ile | ATG | ATC | 1.72 times | 1.47 times |
| | α-94th | Met | Ile | ATG | ATC | | |
| | β-127th | Leu | Ser | CTG | TCG | | |
| | β-160th | Arg | Trp | CGG | TGG | | |
| | β-186th | Leu | Arg | CTG | CGG | | |
| 63 | α-27th | Met | Ile | ATG | ATC | 1.55 times | 1.27 times |
| | α-36th | Thr | Gly | ACG | GGG | | |
| | α-94th | Met | Ile | ATG | ATC | | |
| | α-188th | Thr | Gly | ACC | GGC | | |

Reference Example 27

Construction of a Transformant (64) Substituted Amino Acid Having Nitrile Hydratase Activity

(66) encoding the above nitrile hydratase variant was prepared. A competent cell of *Escherichia coli* HB101 (manufactured by Toyobo Co., Ltd.) was transformed with the plasmid to obtain a transformant (66).

TABLE 37

(Table 24)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 64 | β-37th | Phe | Leu | TTC | CTC |
| | β-108th | Glu | Asp | GAG | GAT |
| | β-200th | Ala | Glu | GCC | GAG |
| 65 | α-6th | Leu | Thr | CTG | ACG |
| | α-36th | Thr | Met | ACG | ATG |
| | α-126th | Phe | Tyr | TTC | TAC |
| | β-10th | Thr | Asp | ACC | GAC |
| | β-118th | Phe | Val | TTC | GTC |
| | β-200th | Ala | Glu | GCC | GAG |
| 66 | β-176th | Tyr | Met | TAC | ATG |
| | β-217th | Asp | Gly | GAC | GGC |

In order to obtain a transformant (64) expressing the nitrile hydratase variant obtained by mutating nitrile hydratase at (aj) amino acid substitution sites as shown in Table 24, the plasma described in Example 67 of Patent Document 2 was used as the template, and the ribosome binding sequence was modified according to the method described in Example 1 to prepare a plasmid (64) encoding the above nitrile hydratase variant. A competent cell of *Escherichia coli* HB101 (manufactured by Toyobo Co., Ltd.) was transformed with the plasmid to obtain a transformant (64).

Reference Example 28

Construction of a Transformant (65) Substituted Amino Acid Having Nitrile Hydratase Activity In order to obtain a transformant (65) expressing the nitrile hydratase variant obtained by mutating nitrile hydratase at (as) amino acid substitution sites as shown in Table 24, the plasma described in Example 76 of Patent Document 2 was used as the template, and the ribosome binding sequence was modified according to the method described in Example 1 to prepare a plasmid (65) encoding the above nitrile hydratase variant. A competent cell of *Escherichia coli* HB101 (manufactured by Toyobo Co., Ltd.) was transformed with the plasmid to obtain a transformant (65).

Reference Example 29

Construction of a Transformant (66) Substituted Amino Acid Having Nitrile Hydratase Activity In order to obtain a transformant (66) expressing the nitrile hydratase variant obtained by mutating nitrile hydratase at (bb) amino acid substitution sites as shown in Table 24, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 47 and 48 in the Sequence Listing were used for repeatedly carrying out the method described in Reference Example 2 per mutation point, whereby a plasmid Example 35

Construction of a Transformant (67) Substituted Amino Acid Having Improved Nitrile Hydratase Activity and Improved Thermal Stability In order to obtain a transformant (67) expressing the nitrile hydratase variant obtained by mutating nitrile hydratase at (n-2) and (aj) amino acid substitution sites as shown in Table 25, the plasmid (64) recovered from the transformant (64) described in the above Reference Example 27 was used as the template, and the primers having the sequence defined in SEQ ID Nos: 46 and 68 in the Sequence Listing were used for repeatedly carrying out the method described in Reference Example 2 per mutation point, whereby a plasmid (67) encoding the above nitrile hydratase variant was prepared. A competent cell of *Escherichia coli* HB101 (manufactured by Toyobo Co., Ltd.) was transformed with the plasmid to obtain a transformant (67). Moreover, the plasmid was prepared from the above-mentioned microbial cells by the alkaline SDS extraction method, and the base sequence of the nitrile hydratase gene was determined using a DNA sequencer. Then, it was confirmed that the transformant (67) had sequences according to the purpose in which mutation of 27th Met in the α-subunit with Ile and mutation of 107th Pro in the β-subunit with Met were newly added to the plasmid (64) of Reference Example 27. In the production of an amide compound using the thus obtained transformant (67) and the transformant (64) to be its base, the initial reaction rate and thermal stability were compared in the same manner as in Example 1.

As a result, it was found that mutation of 27th Met in the α-subunit with Ile and mutation of 107th Pro in the β-subunit with Met were newly added to the transformant (67), so that the initial reaction rate was improved by 1.53 times and thermal stability was improved by 2.23 times, as compared to those of the transformant (64).

Example 36

Construction of a Transformant (68) Substituted Amino Acid Having Improved Nitrile Hydratase Activity and Improved Thermal Stability In order to obtain a transformant (68) expressing the nitrile hydratase variant obtained by mutating nitrile hydratase at (n−2) and (as) amino acid substitution sites as shown in Table 25, the plasmid (65) recovered from the transformant (65) described in the above Reference Example 28 was used as the template, and the primers having the sequence defined in SEQ ID Nos: 46 and 37 in the Sequence Listing were used for repeatedly carrying out the method described in Reference Example 2 per mutation point, whereby a plasmid (68) encoding the above nitrile hydratase variant was prepared. A competent cell of *Escherichia coli* HB101 (manufactured by Toyobo Co., Ltd.) was transformed with the plasmid to obtain a transformant (68). Moreover, the plasmid was prepared from the above-mentioned microbial cells by the alkaline SDS extraction method, and the base sequence of the nitrile hydratase gene was determined using a DNA sequencer. Then, it was confirmed that the transformant (68) had sequences according to the purpose in which mutation of 27th Met in the α-subunit with Ile and mutation of 107th Pro in the β-subunit with Met were newly added to the plasmid (65) of Reference Example 28. In the production of an amide compound using the thus obtained transformant (68) and the transformant (65) to be its base, the initial reaction rate and thermal stability were compared in the same manner as in Example 1.

As a result, it was found that mutation of 27th Met in the α-subunit with Ile and mutation of 107th Pro in the β-subunit with Met were newly added to the transformant (68), so that the initial reaction rate was improved by 1.55 times and thermal stability was improved by 2.15 times, as compared to those of the transformant (65).

Example 37

Construction of a Transformant (69) Substituted Amino Acid Having Improved Nitrile Hydratase Activity and Improved Thermal Stability In order to obtain a transformant (69) expressing the nitrile hydratase variant obtained by mutating nitrile hydratase at (n−2) and (bb) amino acid substitution sites as shown in Table 25, the plasmid (66) recovered from the transformant (66) described in the above Reference Example 29 was used as the template, and the primers having the sequence defined in SEQ ID Nos: 46 and 37 in the Sequence Listing were used for repeatedly carrying out the method described in Reference Example 2 per mutation point, whereby a plasmid (69) encoding the above nitrile hydratase variant was prepared. A competent cell of *Escherichia coli* HB101 (manufactured by Toyobo Co., Ltd.) was transformed with the plasmid to obtain a transformant (69). Moreover, the plasmid was prepared from the above-mentioned microbial cells by the alkaline SDS extraction method, and the base sequence of the nitrile hydratase gene was determined using a DNA sequencer. Then, it was confirmed that the transformant (69) had sequences according to the purpose in which mutation of 27th Met in the α-subunit with Ile and mutation of 107th Pro in the β-subunit with Met were newly added to the plasmid (66) of Reference Example 29. In the production of an amide compound using the thus obtained transformant (69) and the transformant (66) to be its base, the initial reaction rate and thermal stability were compared in the same manner as in Example 1.

As a result, it was found that mutation of 27th Met in the α-subunit with Ile and mutation of 107th Pro in the β-subunit with Met were newly added to the transformant (69), so that the initial reaction rate was improved by 1.46 times and thermal stability was improved by 1.92 times, as compared to those of the transformant (66).

TABLE 38

(Table 25)

| Transformant No. | Mutated Site | Change in Amino Acid Sequence | | Change in Base Sequence | | Improvement of Reaction Rate by α-27th and β-107th Substitution | Improvement of Thermal Stability by α-27th and β-107th Substitution |
|---|---|---|---|---|---|---|---|
| | | Before Substitution | After Substitution | Before Substitution | After Substitution | | |
| 67 | α-27th | Met | Ile | ATG | ATC | 1.53 times | 2.23 times |
| | β-37th | Phe | Leu | TTC | CTC | | |
| | β-107th | Pro | Met | CCC | ATG | | |
| | β-108th | Glu | Asp | GAG | GAT | | |
| | β-200th | Ala | Glu | GCC | GAG | | |
| 68 | α-6th | Leu | Thr | CTG | ACG | 1.55 times | 2.15 times |
| | α-27th | Met | Ile | ATG | ATC | | |
| | α-36th | Thr | Met | ACG | ATG | | |
| | α-126th | Phe | Tyr | TTC | TAC | | |
| | β-10th | Thr | Asp | ACC | GAC | | |
| | β-107th | Pro | Met | CCC | ATG | | |
| | β-118th | Phe | Val | TTC | GTC | | |
| | β-200th | Ala | Glu | GCC | GAG | | |
| 69 | α-27th | Met | Ile | ATG | ATC | 1.46 times | 1.92 times |
| | β-107th | Pro | Met | CCC | ATG | | |
| | β-176th | Tyr | Met | TAC | ATG | | |
| | β-217th | Asp | Gly | GAC | GGC | | |

Reference Example 30

Construction of a Transformant (70) Substituted Amino Acid Having Nitrile Hydratase Activity In order to obtain a transformant (70) expressing the nitrile hydratase variant obtained by mutating nitrile hydratase at (al) amino acid substitution sites as shown in Table 26, the plasma described in Example 69 of Patent Document 2 was used as the template, and the ribosome binding sequence was modified according to the method described in Example 1 to prepare a plasmid (70) encoding the above nitrile hydratase variant. A competent cell of *Escherichia coli* HB101 (manufactured by Toyobo Co., Ltd.) was transformed with the plasmid to obtain a transformant (70).

Reference Example 31

Construction of a Transformant (71) Substituted Amino Acid Having Nitrile Hydratase Activity In order to obtain a transformant (71) expressing the nitrile hydratase variant obtained by mutating nitrile hydratase at (aw) amino acid substitution sites as shown in Table 26, the plasma described in Example 80 of Patent Document 2 was used as the template, and the ribosome binding sequence was modified according to the method described in Example 1 to prepare a plasmid (71) encoding the above nitrile hydratase variant. A competent cell of *Escherichia coli* HB101 (manufactured by Toyobo Co., Ltd.) was transformed with the plasmid to obtain a transformant (71).

Reference Example 32

Construction of a Transformant (72) Substituted Amino Acid Having Nitrile Hydratase Activity In order to obtain a transformant (72) expressing the nitrile hydratase variant obtained by mutating nitrile hydratase at (bl) amino acid substitution sites as shown in Table 26, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 49 and 50 in the Sequence Listing were used for repeatedly carrying out the method described in Reference Example 2 per mutation point, whereby a plasmid (72) encoding the above nitrile hydratase variant was prepared. A competent cell of *Escherichia coli* HB101 (manufactured by Toyobo Co., Ltd.) was transformed with the plasmid to obtain a transformant (72).

TABLE 39

(Table 26)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 70 | β-41st | Phe | Ile | TTC | ATC |
| | β-51st | Phe | Val | TTC | GTC |
| | β-108th | Glu | Asp | GAG | GAT |
| 71 | α-148th | Gly | Asp | GGC | GAC |
| | α-204th | Val | Arg | GTC | CGC |
| | β-108th | Glu | Asp | GAG | GAT |
| | β-200th | Ala | Glu | GCC | GAG |
| 72 | β-61st | Ala | Leu | GCC | CTC |
| | β-112th | Lys | Ile | AAG | ATT |

Example 38

Construction of a Transformant (73) Substituted Amino Acid Having Improved Nitrile Hydratase Activity and Improved Thermal Stability In order to obtain a transformant (73) expressing the nitrile hydratase variant obtained by mutating nitrile hydratase at (q) and (al) amino acid substitution sites as shown in Table 27, the plasmid (70) recovered from the transformant (70) described in the above Reference Example 30 was used as the template, and the primers having the sequence defined in SEQ ID Nos: 16 and 38 in the Sequence Listing were used for repeatedly carrying out the method described in Reference Example 2 per mutation point, whereby a plasmid (73) encoding the above nitrile hydratase variant was prepared. A competent cell of *Escherichia coli* HB101 (manufactured by Toyobo Co., Ltd.) was transformed with the plasmid to obtain a transformant (73). Moreover, the plasmid was prepared from the above-mentioned microbial cells by the alkaline SDS extraction method, and the base sequence of the nitrile hydratase gene was determined using a DNA sequencer. Then, it was confirmed that the transformant (73) had sequences according to the purpose in which mutation of 92nd Asp in the α-subunit with Glu and mutation of 226th Val in the β-subunit with Ile were newly added to the plasmid (70) of Reference Example 30. In the production of an amide compound using the thus obtained transformant (73) and the transformant (70) to be its base, the initial reaction rate and thermal stability were compared in the same manner as in Example 1.

As a result, it was found that mutation of 92nd Asp in the α-subunit with Glu and mutation of 226th Val in the β-subunit with Ile were newly added to the transformant (73), so that the initial reaction rate was improved by 2.00 times and thermal stability was improved by 1.52 times, as compared to those of the transformant (70).

Example 39

Construction of a Transformant (74) Substituted Amino Acid Having Improved Nitrile Hydratase Activity and Improved Thermal Stability In order to obtain a transformant (74) expressing the nitrile hydratase variant obtained by mutating nitrile hydratase at (q) and (aw) amino acid substitution sites as shown in Table 27, the plasmid (71) recovered from the transformant (71) described in the above Reference Example 31 was used as the template, and the primers having the sequence defined in SEQ ID Nos: 16 and 38 in the Sequence Listing were used for repeatedly carrying out the method described in Reference Example 2 per mutation point, whereby a plasmid (74) encoding the above nitrile hydratase variant was prepared. A competent cell of *Escherichia coli* HB101 (manufactured by Toyobo Co., Ltd.) was transformed with the plasmid to obtain a transformant (74). Moreover, the plasmid was prepared from the above-mentioned microbial cells by the alkaline SDS extraction method, and the base sequence of the nitrile hydratase gene was determined using a DNA sequencer. Then, it was confirmed that the transformant (74) had sequences according to the purpose in which mutation of 92nd Asp in the α-subunit with Glu and mutation of 226th Val in the β-subunit with Ile were newly added to the plasmid (71) of Reference Example 31. In the production of an amide compound using the thus obtained transformant (74) and the transformant (71) to be its base, the initial reaction rate and thermal stability were compared in the same manner as in Example 1.

As a result, it was found that mutation of 92nd Asp in the α-subunit with Glu and mutation of 226th Val in the β-subunit with Ile were newly added to the transformant (74), so that the initial reaction rate was improved by 1.78 times and thermal stability was improved by 1.44 times, as compared to those of the transformant (71).

Example 40

Construction of a Transformant (75) Substituted Amino Acid Having Improved Nitrile Hydratase Activity and Improved Thermal Stability In order to obtain a transformant (75) expressing the nitrile hydratase variant obtained by mutating nitrile hydratase at (q) and (bl) amino acid substitution sites as shown in Table 27, the plasmid (72) recovered from the transformant (72) described in the above Reference Example 32 was used as the template, and the primers having the sequence defined in SEQ ID Nos: 16 and 38 in the Sequence Listing were used for repeatedly carrying out the method described in Reference Example 2 per mutation point, whereby a plasmid (75) encoding the above nitrile hydratase variant was prepared. A competent cell of *Escherichia coli* HB101 (manufactured by Toyobo Co., Ltd.) was transformed with the plasmid to obtain a transformant (75). Moreover, the plasmid was prepared from the above-mentioned microbial cells by the alkaline SDS extraction method, and the base sequence of the nitrile hydratase gene was determined using a DNA sequencer. Then, it was confirmed that the transformant (75) had sequences according to the purpose in which mutation of 92nd Asp in the α-subunit with Glu and mutation of 226th Val in the β-subunit with Ile were newly added to the plasmid (72) of Reference Example 32. In the production of an amide compound using the thus obtained transformant (75) and the transformant (72) to be its base, the initial reaction rate and thermal stability were compared in the same manner as in Example 1.

As a result, it was found that mutation of 92nd Asp in the α-subunit with Glu and mutation of 226th Val in the β-subunit with Ile were newly added to the transformant (75), so that the initial reaction rate was improved by 1.85 times and thermal stability was improved by 1.38 times, as compared to those of the transformant (72).

TABLE 40

(Table 27)

| Transformant No. | Mutated Site | Change in Amino Acid Sequence | | Change in Base Sequence | | Improvement of Reaction Rate by α-92nd β-226th Substitution | Improvement of Thermal Stability by α-92nd β-226th Substitution |
|---|---|---|---|---|---|---|---|
| | | Before Substitution | After Substitution | Before Substitution | After Substitution | | |
| 73 | α-92nd | Asp | Glu | GAC | GAG | 2.00 times | 1.52 times |
| | β-41st | Phe | Ile | TTC | ATC | | |
| | β-51st | Phe | Val | TTC | GTC | | |
| | β-108th | Glu | Asp | GAG | GAT | | |
| | β-226th | Val | Ile | GTC | ATC | | |
| 74 | α-92nd | Asp | Glu | GAC | GAG | 1.78 times | 1.44 times |
| | α-148th | Gly | Asp | GGC | GAC | | |
| | α-204th | Val | Arg | GTC | CGC | | |
| | β-108th | Glu | Asp | GAG | GAT | | |
| | β-200th | Ala | Glu | GCC | GAG | | |
| | β-226th | Val | Ile | GTC | ATC | | |
| 75 | α-92nd | Asp | Glu | GAC | GAG | 1.85 times | 1.38 times |
| | β-61st | Ala | Leu | GCC | CTC | | |
| | β-112th | Lys | Ile | AAG | ATT | | |
| | β-226th | Val | Ile | GTC | ATC | | |

Reference Example 33

Construction of a Transformant (76) Substituted Amino Acid Having Nitrile Hydratase Activity In order to obtain a transformant (76) expressing the nitrile hydratase variant obtained by mutating nitrile hydratase at (bi) amino acid substitution sites as shown in Table 28, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 51 and 52 in the Sequence Listing were used for repeatedly carrying out the method described in Reference Example 2 per mutation point, whereby a plasmid (76) encoding the above nitrile hydratase variant was prepared. A competent cell of *Escherichia coli* HB101 (manufactured by Toyobo Co., Ltd.) was transformed with the plasmid to obtain a transformant (76).

Reference Example 34

Construction of a Transformant (77) Substituted Amino Acid Having Nitrile Hydratase Activity In order to obtain a transformant (77) expressing the nitrile hydratase variant obtained by mutating nitrile hydratase at (bm) amino acid substitution sites as shown in Table 28, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 53 and 54 in the Sequence Listing were used for repeatedly carrying out the method described in Reference Example 2 per mutation point, whereby a plasmid (77) encoding the above nitrile hydratase variant was prepared. A competent cell of *Escherichia coli* HB101 (manufactured by Toyobo Co., Ltd.) was transformed with the plasmid to obtain a transformant (77).

Example 41

Construction of a Transformant (78) Substituted Amino Acid Having Improved Nitrile Hydratase Activity and Improved Thermal Stability In order to obtain a transformant (78) expressing the nitrile hydratase variant obtained by mutating nitrile hydratase at (o) and (an) amino acid substitution sites as shown in Table 29, the plasmid (14) recovered from the transformant (14) described in the above Reference Example 7 was used as the template, and the primers having the sequence defined in SEQ ID Nos: 29 and 33 in the Sequence Listing were used for repeatedly carrying out the method described in Reference Example 2 per mutation point, whereby a plasmid (78) encoding the above nitrile hydratase variant was prepared. A competent cell of *Escherichia coli* HB101 (manufactured by Toyobo Co., Ltd.) was transformed with the plasmid to obtain a transformant (78). Moreover, the plasmid was prepared from the above-mentioned microbial cells by the alkaline SDS extraction method, and the base sequence of the nitrile hydratase gene was determined using a DNA sequencer. Then, it was confirmed that the transformant (78) had sequences according to the purpose in which mutation of 4th Val in the β-subunit with Met and mutation of 79th His in the β-subunit with Asn were newly added to the plasmid (14) of Reference Example 7. In the production of an amide compound using the thus obtained transformant (78) and the transformant (14) to be its base, the initial reaction rate and thermal stability were compared in the same manner as in Example 1.

As a result, it was found that mutation of 4th Val in the β-subunit with Met and mutation of 79th His in the β-subunit with Asn were newly added to the transformant (78), so that the initial reaction rate was improved by 1.60 times and thermal stability was improved by 1.46 times, as compared to those of the transformant (14).

Example 42

Construction of a Transformant (79) Substituted Amino Acid Having Improved Nitrile Hydratase Activity and Improved Thermal Stability In order to obtain a transformant (79) expressing the nitrile hydratase variant obtained by mutating nitrile hydratase at (o) and (bi) amino acid substitution sites as shown in Table 29, the plasmid (76) recovered from the transformant (76) described in the above Reference Example 33 was used as the template, and the primers having the sequence defined in SEQ ID Nos: 29 and 33 in the Sequence Listing were used for repeatedly carrying out the method described in Reference Example 2 per mutation point, whereby a plasmid (79) encoding the above nitrile hydratase variant was prepared. A competent cell of *Escherichia coli* HB101 (manufactured by Toyobo Co., Ltd.) was transformed with the plasmid to obtain a transformant (79). Moreover, the plasmid was prepared from the above-mentioned microbial cells by the alkaline SDS extraction method, and the base sequence of the nitrile hydratase gene was determined using a DNA sequencer. Then, it was confirmed that the transformant (79) had sequences according to the purpose in which mutation of 4th Val in the β-subunit with Met and mutation of 79th His in the β-subunit with Asn were newly added to the plasmid (76) of Reference Example 33. In the production of an amide compound using the thus obtained transformant (79) and the transformant (76)

TABLE 41

(Table 28)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 76 | β-61st | Ala | Thr | GCC | ACG |
| | β-218th | Cys | Ser | TGC | TCC |
| 77 | β-146th | Arg | Gly | CGG | GGG |
| | β-217th | Asp | Ser | GAC | AGC | to be its base, the initial reaction rate and thermal stability were compared in the same manner as in Example 1.

As a result, it was found that mutation of 4th Val in the β-subunit with Met and mutation of 79th His in the β-subunit with Asn were newly added to the transformant (79), so that the initial reaction rate was improved by 1.38 times and thermal stability was improved by 1.35 times, as compared to those of the transformant (76).

Example 43

Construction of a Transformant (80) Substituted Amino Acid Having Improved Nitrile Hydratase Activity and Improved Thermal Stability Val in the β-subunit with Met and mutation of 79th His in the β-subunit with Asn were newly added to the plasmid (77) of Reference Example 34. In the production of an amide compound using the thus obtained transformant (80) and the transformant (77) to be its base, the initial reaction rate and thermal stability were compared in the same manner as in Example 1.

As a result, it was found that mutation of 4th Val in the β-subunit with Met and mutation of 79th His in the β-subunit with Asn were newly added to the transformant (80), so that the initial reaction rate was improved by 1.52 times and thermal stability was improved by 1.28 times, as compared to those of the transformant (77).

TABLE 42

(Table 29)

| Transformant No. | Mutated Site | Change in Amino Acid Sequence | | Change in Base Sequence | | Improvement of Reaction Rate by β-4th β-79th Substitution | Improvement of Thermal Stability by β-4th β-79th Substitution |
|---|---|---|---|---|---|---|---|
| | | Before Substitution | After Substitution | Before Substitution | After Substitution | | |
| 78 | β-4th | Val | Met | GTG | ATG | 1.60 times | 1.46 times |
|    | β-48th | Leu | Val | CTG | GTG | | |
|    | β-79th | His | Asn | CAC | AAC | | |
|    | β-108th | Glu | Arg | GAG | CGG | | |
|    | β-212th | Ser | Tyr | TCC | TAC | | |
| 79 | β-4th | Val | Met | GTG | ATG | 1.38 times | 1.35 times |
|    | β-61st | Ala | Thr | GCC | ACG | | |
|    | β-79th | His | Asn | CAC | AAC | | |
|    | β-218th | Cys | Ser | TGC | TCC | | |
| 80 | β-4th | Val | Met | GTG | ATG | 1.52 times | 1.28 times |
|    | β-79th | His | Asn | CAC | AAC | | |
|    | β-146th | Arg | Gly | CGG | GGG | | |
|    | β-217th | Asp | Ser | GAC | AGC | | |

In order to obtain a transformant (80) expressing the nitrile hydratase variant obtained by mutating nitrile hydratase at (o) and (bm) amino acid substitution sites as shown in Table 29, the plasmid (77) recovered from the transformant (77) described in the above Reference Example 34 was used as the template, and the primers having the sequence defined in SEQ ID Nos: 29 and 33 in the Sequence Listing were used for repeatedly carrying out the method described in Reference Example 2 per mutation point, whereby a plasmid (80) encoding the above nitrile hydratase variant was prepared. A competent cell of *Escherichia coli* HB101 (manufactured by Toyobo Co., Ltd.) was transformed with the plasmid to obtain a transformant (80). Moreover, the plasmid was prepared from the above-mentioned microbial cells by the alkaline SDS extraction method, and the base sequence of the nitrile hydratase gene was determined using a DNA sequencer. Then, it was confirmed that the transformant (80) had sequences according to the purpose in which mutation of 4th

Reference Example 35

Construction of a Transformant (81) Substituted Amino Acid Having Nitrile Hydratase Activity In order to obtain a transformant (81) expressing the nitrile hydratase variant obtained by mutating nitrile hydratase at (ag) amino acid substitution sites as shown in Table 30, the plasma described in Example 64 of Patent Document 2 was used as the template, and the ribosome binding sequence was modified according to the method described in Example 1 to prepare a plasmid (81) encoding the above nitrile hydratase variant. A competent cell of *Escherichia coli* HB101 (manufactured by Toyobo Co., Ltd.) was transformed with the plasmid to obtain a transformant (81).

Reference Example 36

Construction of a Transformant (82) Substituted Amino Acid Having Nitrile Hydratase Activity In order to obtain a transformant (82) expressing the nitrile hydratase variant obtained by mutating nitrile hydratase at (ai) amino acid substitution sites as shown in Table 30, the plasma described in Example 66 of Patent Document 2 was used as the template, and the ribosome binding sequence was modified according to the method described in Example 1 to prepare a plasmid (82) encoding the above nitrile hydratase variant. A competent cell of *Escherichia coli* HB101 (manufactured by Toyobo Co., Ltd.) was transformed with the plasmid to obtain a transformant (82).

TABLE 43

(Table 30)

| Transformant No. | Mutated Site | Change in Amino Acid Sequence | | Change in Base Sequence | |
| --- | --- | --- | --- | --- | --- |
| | | Before Substitution | After Substitution | Before Substitution | After Substitution |
| 81 | α-19th | Ala | Val | GCG | GTG |
| | α-71st | Arg | His | CGT | CAT |
| | α-126th | Phe | Tyr | TTC | TAC |
| 82 | β-10th | Thr | Asp | ACC | GAC |
| | β-118th | Phe | Val | TTC | GTC |
| | β-200th | Ala | Glu | GCC | GAG |

Example 44

Construction of a Transformant (83) Substituted Amino Acid Having Improved Nitrile Hydratase Activity and Improved Thermal Stability In order to obtain a transformant (83) expressing the nitrile hydratase variant obtained by mutating nitrile hydratase at (p) and (ag) amino acid substitution sites as shown in Table 31, the plasmid (81) recovered from the transformant (81) described in the above Reference Example 35 was used as the template, and the primers having the sequence defined in SEQ ID Nos: 33 and 60 in the Sequence Listing were used for repeatedly carrying out the method described in Reference Example 2 per mutation point, whereby a plasmid (83) encoding the above nitrile hydratase variant was prepared. A competent cell of *Escherichia coli* HB101 (manufactured by Toyobo Co., Ltd.) was transformed with the plasmid to obtain a transformant (83). Moreover, the plasmid was prepared from the above-mentioned microbial cells by the alkaline SDS extraction method, and the base sequence of the nitrile hydratase gene was determined using a DNA sequencer. Then, it was confirmed that the transformant (83) had sequences according to the purpose in which mutation of 79th His in the β-subunit with Asn and mutation of 230th Ala in the β-subunit with Glu were newly added to the plasmid (81) of Reference Example 35. In the production of an amide compound using the thus obtained transformant (83) and the transformant (81) to be its base, the initial reaction rate and thermal stability were compared in the same manner as in Example 1.

As a result, it was found that mutation of 79th His in the β-subunit with Asn and mutation of 230th Ala in the β-subunit with Glu were newly added to the transformant (83), so that the initial reaction rate was improved by 1.25 times and thermal stability was improved by 2.16 times, as compared to those of the transformant (81).

Example 45

Construction of a Transformant (84) Substituted Amino Acid Having Improved Nitrile Hydratase Activity and Improved Thermal Stability In order to obtain a transformant (84) expressing the nitrile hydratase variant obtained by mutating nitrile hydratase at (p) and (ai) amino acid substitution sites as shown in Table 31, the plasmid (82) recovered from the transformant (82) described in the above Reference Example 36 was used as the template, and the primers having the sequence defined in SEQ ID Nos: 33 and 60 in the Sequence Listing were used for repeatedly carrying out the method described in Reference Example 2 per mutation point, whereby a plasmid (84) encoding the above nitrile hydratase variant was prepared. A competent cell of *Escherichia coli* HB101 (manufactured by Toyobo Co., Ltd.) was transformed with the plasmid to obtain a transformant (84). Moreover, the plasmid was prepared from the above-mentioned microbial cells by the alkaline SDS extraction method, and the base sequence of the nitrile hydratase gene was determined using a DNA sequencer. Then, it was confirmed that the transformant (84) had sequences according to the purpose in which mutation of 79th His in the β-subunit with Asn and mutation of 230th Ala in the β-subunit with Glu were newly added to the plasmid (82) of Reference Example 36. In the production of an amide compound using the thus obtained transformant (84) and the transformant (82) to be its base, the initial reaction rate and thermal stability were compared in the same manner as in Example 1.

As a result, it was found that mutation of 79th His in the β-subunit with Asn and mutation of 230th Ala in the β-subunit with Glu were newly added to the transformant (84), so that the initial reaction rate was improved by 1.27 times and thermal stability was improved by 2.10 times, as compared to those of the transformant (82).

Example 46

Construction (85) of a Transformant (85) Substituted Amino Acid Having Improved Nitrile Hydratase Activity and Improved Thermal Stability In order to obtain a transformant (85) expressing the nitrile hydratase variant obtained by mutating nitrile hydratase at (p) and (aq) amino acid substitution sites as shown in Table 31, the plasmid (38) recovered from the transformant (38) described in the above Reference Example 19 was used as the template, and the primers having the sequence defined in SEQ ID Nos: 33 and 60 in the Sequence Listing were used for repeatedly carrying out the method described in Reference Example 2 per mutation point, whereby a plasmid (85) encoding the above nitrile hydratase variant was prepared. A competent cell of *Escherichia coli* HB101 (manufactured by Toyobo Co., Ltd.) was transformed with the plasmid to obtain a transformant (85). Moreover, the plasmid was prepared from the above-mentioned microbial cells by the alkaline SDS extraction method, and the base sequence of the nitrile hydratase gene was determined using a DNA sequencer.

Then, it was confirmed that the transformant (85) had sequences according to the purpose in which mutation of 79th His in the β-subunit with Asn and mutation of 230th Ala in the β-subunit with Glu were newly added to the plasmid (38) of Reference Example 31. In the production of an amide compound using the thus obtained transformant (85) and the transformant (38) to be its base, the initial reaction rate and thermal stability were compared in the same manner as in Example 1.

As a result, it was found that mutation of 79th His in the β-subunit with Asn and mutation of 230th Ala in the β-subunit with Glu were newly added to the transformant (85), so that the initial reaction rate was improved by 1.33 times and thermal stability was improved by 2.52 times, as compared to those of the transformant (38).

TABLE 44

(Table 31)

| Trans-formant No. | Mutated Site | Change in Amino Acid Sequence | | Change in Base Sequence | | Improvement of Reaction Rate by β-79th and β-230th Substitution | Improvement of Thermal Stability by β-79th and β-230th Substitution |
|---|---|---|---|---|---|---|---|
| | | Before Substi-tution | After Substi-tution | Before Substi-tution | After Substi-tution | | |
| 83 | α-19th | Ala | Val | GCG | GTG | 1.25 times | 2.16 times |
| | α-71st | Arg | His | CGT | CAT | | |
| | α-126th | Phe | Tyr | TTC | TAC | | |
| | β-79th | His | Asn | CAC | AAC | | |
| | β-230th | Ala | Glu | GCG | GAG | | |
| 84 | β-10th | Thr | Asp | ACC | GAC | 1.27 times | 2.10 times |
| | β-79th | His | Asn | CAC | AAC | | |
| | β-118th | Phe | Val | TTC | GTC | | |
| | β-200th | Ala | Glu | GCC | GAG | | |
| | β-230th | Ala | Glu | GCG | GAG | | |
| 85 | α-6th | Leu | Thr | CTG | ACG | 1.33 times | 2.52 times |
| | α-19th | Ala | Val | GCG | GTG | | |
| | α-126th | Phe | Tyr | TTC | TAC | | |
| | β-48th | Leu | Val | CTG | GTG | | |
| | β-79th | His | Asn | CAC | AAC | | |
| | β-108th | Glu | Arg | GAG | CGG | | |
| | β-212th | Ser | Tyr | TCC | TAC | | |
| | β-230th | Ala | Glu | GCG | GAG | | |

Reference Example 37

Construction of a Transformant (86) Substituted Amino Acid Having Nitrile Hydratase Activity In order to obtain a transformant (86) expressing the nitrile hydratase variant obtained by mutating nitrile hydratase at (ad) amino acid substitution sites as shown in Table 32, the plasma described in Example 61 of Patent Document 2 was used as the template, and the ribosome binding sequence was modified according to the method described in Example 1 to prepare a plasmid (86) encoding the above nitrile hydratase variant. A competent cell of *Escherichia coli* HB101 (manufactured by Toyobo Co., Ltd.) was transformed with the plasmid to obtain a transformant (86).

Reference Example 38

Construction of a Transformant (87) Substituted Amino Acid Having Nitrile Hydratase Activity In order to obtain a transformant (87) expressing the nitrile hydratase variant obtained by mutating nitrile hydratase at (bg) amino acid substitution sites as shown in Table 32, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 55 and 56 in the Sequence Listing were used for repeatedly carrying out the method described in Reference Example 2 per mutation point, whereby a plasmid (87) encoding the above nitrile hydratase variant was prepared. A competent cell of *Escherichia coli* HB101 (manufactured by Toyobo Co., Ltd.) was transformed with the plasmid to obtain a transformant (87).

TABLE 45

(Table 32)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 86 | β-118th | Phe | Val | TTC | GTC |
| | β-200th | Ala | Glu | GCC | GAG |
| 87 | β-40th | Thr | Leu | ACG | CTG |
| | β-217th | Asp | Leu | GAC | CTC |

Example 47

Construction of a Transformant (88) Substituted Amino Acid Having Improved Nitrile Hydratase Activity and Improved Thermal Stability In order to obtain a transformant (88) expressing the nitrile hydratase variant obtained by mutating nitrile hydratase at (j) and (ad) amino acid substitution sites as shown in Table 33, the plasmid (86) recovered from the transformant (86) described in the above Reference Example 37 was used as the template, and the primers having the sequence defined in SEQ ID Nos: 57 and 58 in the Sequence Listing were used for repeatedly carrying out the method described in Reference Example 2 per mutation point, whereby a plasmid (88) encoding the above nitrile hydratase variant was prepared. A competent cell of *Escherichia coli* HB101 (manufactured by Toyobo Co., Ltd.) was transformed with the plasmid to obtain a transformant (88). Moreover, the plasmid was prepared from the above-mentioned microbial cells by the alkaline SDS extraction method, and the base sequence of the nitrile hydratase gene was determined using a DNA sequencer. Then, it was confirmed that the transformant (88) had sequences according to the purpose in which mutation of 110th Glu in the β-subunit with Asn and mutation of 231st Ala in the β-subunit with Val were newly added to the plasmid (86) of Reference Example 37. In the production of an amide compound using the thus obtained transformant (88) and the transformant (86) to be its base, the initial reaction rate and thermal stability were compared in the same manner as in Example 1.

As a result, it was found that mutation of 110th Glu in the β-subunit with Asn and mutation of 231st Ala in the β-subunit with Val were newly added to the transformant (88), so that the initial reaction rate was improved by 1.29 times and thermal stability was improved by 1.62 times, as compared to those of the transformant (86).

Example 48

Construction of a Transformant (89) Substituted Amino Acid Having Improved Nitrile Hydratase Activity and Improved Thermal Stability In order to obtain a transformant (89) expressing the nitrile hydratase variant obtained by mutating nitrile hydratase at (j) and (aj) amino acid substitution sites as shown in Table 33, the plasmid (64) recovered from the transformant (64) described in the above Reference Example 27 was used as the template, and the primers having the sequence defined in SEQ ID Nos: 57 and 58 in the Sequence Listing were used for repeatedly carrying out the method described in Reference Example 2 per mutation point, whereby a plasmid (89) encoding the above nitrile hydratase variant was prepared. A competent cell of *Escherichia coli* HB101 (manufactured by Toyobo Co., Ltd.) was transformed with the plasmid to obtain a transformant (89). Moreover, the plasmid was prepared from the above-mentioned microbial cells by the alkaline SDS extraction method, and the base sequence of the nitrile hydratase gene was determined using a DNA sequencer. Then, it was confirmed that the transformant (89) had sequences according to the purpose in which mutation of 110th Glu in the β-subunit with Asn and mutation of 231st Ala in the β-subunit with Val were newly added to the plasmid (64) of Reference Example 27. In the production of an amide compound using the thus obtained transformant (89) and the transformant (64) to be its base, the initial reaction rate and thermal stability were compared in the same manner as in Example 1.

As a result, it was found that mutation of 110th Glu in the β-subunit with Asn and mutation of 231st Ala in the β-subunit with Val were newly added to the transformant (89), so that the initial reaction rate was improved by 1.34 times and thermal stability was improved by 1.83 times, as compared to those of the transformant (64).

Example 49

Construction of a Transformant (90) Substituted Amino Acid Having Improved Nitrile Hydratase Activity and Improved Thermal Stability In order to obtain a transformant (90) expressing the nitrile hydratase variant obtained by mutating nitrile hydratase at (j) and (bg) amino acid substitution sites as shown in Table 33, the plasmid (87) recovered from the transformant (87) described in the above Reference Example 38 was used as the template, and the primers having the sequence defined in SEQ ID Nos: 57 and 58 in the Sequence Listing were used for repeatedly carrying out the method described in Reference Example 2 per mutation point, whereby a plasmid (90) encoding the above nitrile hydratase variant was prepared. A competent cell of *Escherichia coli* HB101 (manufactured by Toyobo Co., Ltd.) was transformed with the plasmid to obtain a transformant (90). Moreover, the plasmid was prepared from the above-mentioned microbial cells by the alkaline SDS extraction method, and the base sequence of the nitrile hydratase gene was determined using a DNA sequencer. Then, it was confirmed that the transformant (90) had sequences according to the purpose in which mutation of 110th Glu in the β-subunit with Asn and mutation of 231st Ala in the β-subunit with Val were newly added to the plasmid (87) of Reference Example 38. In the production of an amide compound using the thus obtained transformant (90) and the transformant (87) to be its base, the initial reaction rate and thermal stability were compared in the same manner as in Example 1.

As a result, it was found that mutation of 110th Glu in the β-subunit with Asn and mutation of 231st Ala in the β-subunit with Val were newly added to the transformant (90), so that the initial reaction rate was improved by 1.25 times and thermal stability was improved by 1.46 times, as compared to those of the transformant (87).

TABLE 46

(Table 33)

| Transformant No. | Mutated Site | Change in Amino Acid Sequence Before Substitution | Change in Amino Acid Sequence After Substitution | Change in Base Sequence Before Substitution | Change in Base Sequence After Substitution | Improvement of Reaction Rate by β-110th and β-231st Substitution | Improvement of Thermal Stability by β-110th and β-231st Substitution |
|---|---|---|---|---|---|---|---|
| 88 | β-110th | Glu | Asn | GAG | AAC | 1.29 times | 1.62 times |
|  | β-118th | Phe | Val | TTC | GTC |  |  |
|  | β-200th | Ala | Glu | GCC | GAG |  |  |
|  | β-231st | Ala | Val | GCC | GTC |  |  |
| 89 | β-37th | Phe | Leu | TTC | CTC | 1.34 times | 1.83 times |
|  | β-108th | Glu | Asp | GAG | GAT |  |  |
|  | β-110th | Glu | Asn | GAG | AAC |  |  |
|  | β-200th | Ala | Glu | GCC | GAG |  |  |
|  | β-231st | Ala | Val | GCC | GTC |  |  |
| 90 | β-40th | Thr | Leu | ACG | CTG | 1.25 times | 1.46 times |
|  | β-110th | Glu | Asn | GAG | AAC |  |  |
|  | β-217th | Asp | Leu | GAC | CTC |  |  |
|  | β-231st | Ala | Val | GCC | GTC |  |  |

Example 50

Construction of a Transformant (91) Substituted Amino Acid Having Improved Nitrile Hydratase Activity and Improved Thermal Stability In order to obtain a transformant (91) expressing the nitrile hydratase variant obtained by mutating nitrile hydratase at (k) and (ad) amino acid substitution sites as shown in Table 34, the plasmid (86) recovered from the transformant (86) described in the above Reference Example 37 was used as the template, and the primers having the sequence defined in SEQ ID Nos: 59 and 60 in the Sequence Listing were used for repeatedly carrying out the method described in Reference Example 2 per mutation point, whereby a plasmid (91) encoding the above nitrile hydratase variant was prepared. A competent cell of *Escherichia coli* HB101 (manufactured by Toyobo Co., Ltd.) was transformed with the plasmid to obtain a transformant (91). Moreover, the plasmid was prepared from the above-mentioned microbial cells by the alkaline SDS extraction method, and the base sequence of the nitrile hydratase gene was determined using a DNA sequencer. Then, it was confirmed that the transformant (91) had sequences according to the purpose in which mutation of 206th Pro in the β-subunit with Leu and mutation of 230th Ala in the β-subunit with Glu were newly added to the plasmid (86) of Reference Example 37. In the production of an amide compound using the thus obtained transformant (91) and the transformant (86) to be its base, the initial reaction rate and thermal stability were compared in the same manner as in Example As a result, it was found that mutation of 206th Pro in the β-subunit with Leu and mutation of 230th Ala in the β-subunit with Glu were newly added to the transformant (91), so that the initial reaction rate was improved by 1.44 times and thermal stability was improved by 1.42 times, as compared to those of the transformant (86).

Example 51

Construction of a Transformant (92) Substituted Amino Acid Having Improved Nitrile Hydratase Activity and Improved Thermal Stability In order to obtain a transformant (92) expressing the nitrile hydratase variant obtained by mutating nitrile hydratase at (k) and (as) amino acid substitution sites as shown in Table 34, the plasmid (65) recovered from the transformant (65) described in the above Reference Example 28 was used as the template, and the primers having the sequence defined in SEQ ID Nos: 59 and 60 in the Sequence Listing were used for repeatedly carrying out the method described in Reference Example 2 per mutation point, whereby a plasmid (92) encoding the above nitrile hydratase variant was prepared. A competent cell of *Escherichia coli* HB101 (manufactured by Toyobo Co., Ltd.) was transformed with the plasmid to obtain a transformant (92). Moreover, the plasmid was prepared from the above-mentioned microbial cells by the alkaline SDS extraction method, and the base sequence of the nitrile hydratase gene was determined using a DNA sequencer. Then, it was confirmed that the transformant (92) had sequences according to the purpose in which mutation of 206th Pro in the β-subunit with Leu and mutation of 230th Ala in the β-subunit with Glu were newly added to the plasmid (65) of Reference Example 28. In the production of an amide compound using the thus obtained transformant (92) and the transformant (65) to be its base, the initial reaction rate and thermal stability were compared in the same manner as in Example 1.

As a result, it was found that mutation of 206th Pro in the β-subunit with Leu and mutation of 230th Ala in the β-subunit with Glu were newly added to the transformant (92), so that the initial reaction rate was improved by 1.48 times and thermal stability was improved by 1.39 times, as compared to those of the transformant (65).

Example 52

Construction of a Transformant (93) Substituted Amino Acid Having Improved Nitrile Hydratase Activity and Improved Thermal Stability In order to obtain a transformant (93) expressing the nitrile hydratase variant obtained by mutating nitrile hydratase at (k) and (av) amino acid substitution sites as shown in Table 34, the plasmid (2) recovered from the transformant (2) described in the above Reference Example 1 was used as the template, and the primers having the sequence defined in SEQ ID Nos: 59 and 60 in the Sequence Listing were used for repeatedly carrying out the method described in Reference Example 2 per mutation point, whereby a plasmid (93) encoding the above nitrile hydratase variant was prepared. A competent cell of *Escherichia coli* HB101 (manufactured by Toyobo Co., Ltd.) was transformed with the plasmid to obtain a transformant (93). Moreover, the plasmid was prepared from the above-mentioned microbial cells by the alkaline SDS extraction method, and the base sequence of the nitrile hydratase gene was determined using a DNA sequencer. Then, it was confirmed that the transformant (93) had sequences according to the purpose in which mutation of 206th Pro in the β-subunit with Leu and mutation of 230th Ala in the β-subunit with Glu were newly added to the plasmid (2) of Reference Example 1. In the production of an amide compound using the thus obtained transformant (93) and the transformant (2) to be its base, the initial reaction rate and thermal stability were compared in the same manner as in Example 1.

As a result, it was found that mutation of 206th Pro in the β-subunit with Leu and mutation of 230th Ala in the β-subunit with Glu were newly added to the transformant (93), so that the initial reaction rate was improved by 1.36 times and thermal stability was improved by 1.52 times, as compared to those of the transformant (2).

TABLE 47

(Table 34)

| Trans-formant No. | Mutated Site | Change in Amino Acid Sequence Before Substitution | Change in Amino Acid Sequence After Substitution | Change in Base Sequence Before Substitution | Change in Base Sequence After Substitution | Improvement of Reaction Rate by β-206th and β-230th Substitution | Improvement of Thermal Stability by β-206th and β-230th Substitution |
|---|---|---|---|---|---|---|---|
| 91 | β-118th | Phe | Val | TCC | GTC | 1.44 times | 1.42 times |
|  | β-200th | Ala | Glu | GCC | GAG |  |  |

TABLE 47-continued (Table 34)

| Trans-formant No. | Mutated Site | Change in Amino Acid Sequence | | Change in Base Sequence | | Improvement of Reaction Rate by β-206th and β-230th Substitution | Improvement of Thermal Stability by β-206th and β-230th Substitution |
|---|---|---|---|---|---|---|---|
| | | Before Substitution | After Substitution | Before Substitution | After Substitution | | |
| | β-206th | Pro | Leu | CCG | CTG | | |
| | β-230th | Ala | Glu | GCG | GAG | | |
| 92 | α-6th | Leu | Thr | CTG | ACG | 1.48 times | 1.39 times |
| | α-36th | Thr | Met | ACG | ATG | | |
| | α-126th | Phe | Tyr | TTC | TAC | | |
| | β-10th | Thr | Asp | ACC | GAC | | |
| | β-118th | Phe | Val | TTC | GTC | | |
| | β-200th | Ala | Glu | GCC | GAG | | |
| | β-206th | Pro | Leu | CCG | CTG | | |
| | β-230th | Ala | Glu | GCG | GAG | | |
| 93 | α-36th | Thr | Met | ACG | ATG | 1.36 times | 1.52 times |
| | α-148th | Gly | Asp | GGC | GAC | | |
| | α-204th | Val | Arg | GTC | CGC | | |
| | β-41st | Phe | Ile | TTC | ATC | | |
| | β-51st | Phe | Val | TTC | GTC | | |
| | β-108th | Glu | Asp | GAG | GAT | | |
| | β-206th | Pro | Leu | CCG | CTG | | |
| | β-230th | Ala | Glu | GCG | GAG | | |

Reference Example 39

Construction of a Transformant (94) Substituted Amino Acid Having Nitrile Hydratase Activity In order to obtain a transformant (94) expressing the nitrile hydratase variant obtained by mutating nitrile hydratase at (bo) amino acid substitution sites as shown in Table 35, introduction of site-specific mutation was performed using the mutagenesis kit described in the above Reference Example 2.

The plasmid (1) expressing nitrile hydratase with the modified ribosome binding sequence described in Example 1 was used as the template, and the primers having the sequence defined in SEQ ID Nos: 61 and 62 in the Sequence Listing were used for repeatedly carrying out the method described in Reference Example 2 per mutation point, whereby a plasmid (94) encoding the above nitrile hydratase variant was prepared. A competent cell of Escherichia coli HB101 (manufactured by Toyobo Co., Ltd.) was transformed with the plasmid to obtain a transformant (94).

TABLE 48

(Table 35)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 94 | β-150th | Ala | Ser | GCG | TCG |
| | β-217th | Asp | Cys | GAC | TGT |

Example 53

Construction of a Transformant (95) Substituted Amino Acid Having Improved Nitrile Hydratase Activity and Improved Thermal Stability In order to obtain a transformant (95) expressing the nitrile hydratase variant obtained by mutating nitrile hydratase at (l) and (ag) amino acid substitution sites as shown in Table 36, the plasmid (81) recovered from the transformant (81) described in the above Reference Example 35 was used as the template, and the primers having the sequence defined in SEQ ID Nos: 43, 46 and 57 in the Sequence Listing were used for repeatedly carrying out the method described in Reference Example 2 per mutation point, whereby a plasmid (95) encoding the above nitrile hydratase variant was prepared. A competent cell of Escherichia coli HB101 (manufactured by Toyobo Co., Ltd.) was transformed with the plasmid to obtain a transformant (95). Moreover, the plasmid was prepared from the above-mentioned microbial cells by the alkaline SDS extraction method, and the base sequence of the nitrile hydratase gene was determined using a DNA sequencer. Then, it was confirmed that the transformant (95) had sequences according to the purpose in which mutation of 13th Ile in the α-subunit with Leu, mutation of 27th Met in the α-subunit with Ile and mutation of 110th Glu in the β-subunit with Asn were newly added to the plasmid (81) of Reference Example 35. In the production of an amide compound using the thus obtained transformant (95) and the transformant (81) to be its base, the initial reaction rate and thermal stability were compared in the same manner as in Example 1.

As a result, it was found that mutation of 13th Ile in the α-subunit with Leu, mutation of 27th Met in the α-subunit with Ile and mutation of 110th Glu in the β-subunit with Asn were newly added to the transformant (95), so that the initial reaction rate was improved by 1.53 times and thermal stability was improved by 1.76 times, as compared to those of the transformant (81).

Example 54

Construction of a Transformant (96) Substituted Amino Acid Having Improved Nitrile Hydratase Activity and Improved Thermal Stability In order to obtain a transformant (96) expressing the nitrile hydratase variant obtained by mutating nitrile hydratase at (l) and (am) amino acid substitution sites as shown in Table 36, the plasmid (56) recovered from the transformant (56) described in the above Reference Example 25 was used as the template, and the primers having the sequence defined in SEQ ID Nos: 43, 46 and 57 in the Sequence Listing were used for repeatedly carrying out the method described in Reference Example 2 per mutation point, whereby a plasmid (96) encoding the above nitrile hydratase variant was prepared. A competent cell of Escherichia coli HB101 (manufactured by Toyobo Co., Ltd.) was transformed with the plasmid to obtain a transformant (96). Moreover, the plasmid was prepared from the above-mentioned microbial cells by the alkaline SDS extraction method, and the base sequence of the nitrile hydratase gene was determined using a DNA sequencer. Then, it was confirmed that the transformant (96) had sequences according to the purpose in which mutation of 13th Ile in the α-subunit with Leu, mutation of 27th Met in the α-subunit with Ile and mutation of 110th Glu in the β-subunit with Asn were newly added to the plasmid (56) of Reference Example 25. In the production of an amide compound using the thus obtained transformant (96) and the transformant (56) to be its base, the initial reaction rate and thermal stability were compared in the same manner as in Example 1.

As a result, it was found that mutation of 13th Ile in the α-subunit with Leu, mutation of 27th Met in the α-subunit with Ile and mutation of 110th Glu in the β-subunit with Asn were newly added to the transformant (96), so that the initial reaction rate was improved by 1.49 times and thermal stability was improved by 1.69 times, as compared to those of the transformant (56).

Example 55

Construction of a Transformant (97) Substituted Amino Acid Having Improved Nitrile Hydratase Activity and Improved Thermal Stability In order to obtain a transformant (97) expressing the nitrile hydratase variant obtained by mutating nitrile hydratase at (l) and (bo) amino acid substitution sites as shown in Table 36, the plasmid (94) recovered from the transformant (94) described in the above Reference Example 39 was used as the template, and the primers having the sequence defined in SEQ ID Nos: 43, 46 and 57 in the Sequence Listing were used for repeatedly carrying out the method described in Reference Example 2 per mutation point, whereby a plasmid (97) encoding the above nitrile hydratase variant was prepared. A competent cell of Escherichia coli HB101 (manufactured by Toyobo Co., Ltd.) was transformed with the plasmid to obtain a transformant (97). Moreover, the plasmid was prepared from the above-mentioned microbial cells by the alkaline SDS extraction method, and the base sequence of the nitrile hydratase gene was determined using a DNA sequencer. Then, it was confirmed that the transformant (97) had sequences according to the purpose in which mutation of 13th Ile in the α-subunit with Leu, mutation of 27th Met in the α-subunit with Ile and mutation of 110th Glu in the β-subunit with Asn were newly added to the plasmid (94) of Reference Example 39. In the production of an amide compound using the thus obtained transformant (97) and the transformant (94) to be its base, the initial reaction rate and thermal stability were compared in the same manner as in Example 1.

As a result, it was found that mutation of 13th Ile in the α-subunit with Leu, mutation of 27th Met in the α-subunit with Ile and mutation of 110th Glu in the β-subunit with Asn were newly added to the transformant (97), so that the initial reaction rate was improved by 1.37 times and thermal stability was improved by 1.83 times, as compared to those of the transformant (94).

TABLE 49

(Table 36)

| Transformant No. | Mutated Site | Change in Amino Acid Sequence | | Change in Base Sequence | | Improvement of Reaction Rate by α-113th, α-27th and β-110th Substitution | Improvement of Thermal Stability by α-13th, α-27th and β-110th Substitution |
|---|---|---|---|---|---|---|---|
| | | Before Substitution | After Substitution | Before Substitution | After Substitution | | |
| 95 | α-13th | Ile | Leu | ATC | CTC | 1.53 times | 1.76 times |
| | α-19th | Ala | Val | GCG | GTG | | |
| | α-27th | Met | Ile | ATG | ATC | | |
| | α-71st | Arg | His | CGT | CAT | | |
| | α-126th | Phe | Tyr | TTC | TAC | | |
| | β-110th | Glu | Asn | GAG | AAC | | |
| 96 | α-13th | Ile | Leu | ATC | CTC | 1.49 times | 1.69 times |
| | α-27th | Met | Ile | ATG | ATC | | |
| | β-46th | Met | Lys | ATG | AAG | | |
| | β-108th | Glu | Arg | GAG | CGG | | |
| | β-110th | Glu | Asn | GAG | AAC | | |
| | β-212th | Ser | Tyr | TCC | TAC | | |
| 97 | α-13th | Ile | Leu | ATC | CTC | 1.37 times | 1.83 times |
| | α-27th | Met | Ile | ATG | ATC | | |
| | β-110th | Glu | Asn | GAG | AAC | | |
| | β-150th | Ala | Ser | GCG | TCG | | |
| | β-217th | Asp | Cys | GAC | TGT | | |

Reference Example 40

Construction of a Transformant (98) Substituted Amino Acid Having Nitrile Hydratase Activity In order to obtain a transformant (98) expressing the nitrile hydratase variant obtained by mutating nitrile hydratase at (ab) amino acid substitution sites as shown in Table 37, the plasma described in Example 59 of Patent Document 2 was used as the template, and the ribosome binding sequence was modified according to the method described in Example 1 to prepare a plasmid (98) encoding the above nitrile hydratase variant. A competent cell of Escherichia coli HB101 (manufactured by Toyobo Co., Ltd.) was transformed with the plasmid to obtain a transformant (98).

TABLE 50

(Table 37)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 98 | α-148th | Gly | Asp | GGC | GAC |
| | α-204th | Val | Arg | GTC | CGC |

Example 56

Construction of a Transformant (99) Substituted Amino Acid Having Improved Nitrile Hydratase Activity and Improved Thermal Stability In order to obtain a transformant (99) expressing the nitrile hydratase variant obtained by mutating nitrile hydratase at (r) and (ab) amino acid substitution sites as shown in Table 38, the plasmid (98) recovered from the transformant (98) described in the above Reference Example 40 was used as the template, and the primers having the sequence defined in SEQ ID Nos: 43, 59 and 38 in the Sequence Listing were used for repeatedly carrying out the method described in Reference Example 2 per mutation point, whereby a plasmid (99) encoding the above nitrile hydratase variant was prepared. A competent cell of Escherichia coli HB101 (manufactured by Toyobo Co., Ltd.) was transformed with the plasmid to obtain a transformant (99). Moreover, the plasmid was prepared from the above-mentioned microbial cells by the alkaline SDS extraction method, and the base sequence of the nitrile hydratase gene was determined using a DNA sequencer. Then, it was confirmed that the transformant (99) had sequences according to the purpose in which mutation of 13th Ile in the α-subunit with Leu, mutation of 206th Pro in the β-subunit with Leu and mutation of 226th Val in the β-subunit with Ile were newly added to the plasmid (98) of Reference Example 40. In the production of an amide compound using the thus obtained transformant (99) and the transformant (98) to be its base, the initial reaction rate and thermal stability were compared in the same manner as in Example 1.

As a result, it was found that mutation of 13th Ile in the α-subunit with Leu, mutation of 206th Pro in the β-subunit with Leu and mutation of 226th Val in the β-subunit with Ile were newly added to the transformant (99), so that the initial reaction rate was improved by 1.85 times and thermal stability was improved by 1.36 times, as compared to those of the transformant (98).

Example 57

Construction of a Transformant (100) Substituted Amino Acid Having Improved Nitrile Hydratase Activity and Improved Thermal Stability In order to obtain a transformant (100) expressing the nitrile hydratase variant obtained by mutating nitrile hydratase at (r) and (ai) amino acid substitution sites as shown in Table 38, the plasmid (82) recovered from the transformant (82) described in the above Reference Example 36 was used as the template, and the primers having the sequence defined in SEQ ID Nos: 43, 59 and 38 in the Sequence Listing were used for repeatedly carrying out the method described in Reference Example 2 per mutation point, whereby a plasmid (100) encoding the above nitrile hydratase variant was prepared. A competent cell of Escherichia coli HB101 (manufactured by Toyobo Co., Ltd.) was transformed with the plasmid to obtain a transformant (100). Moreover, the plasmid was prepared from the above-mentioned microbial cells by the alkaline SDS extraction method, and the base sequence of the nitrile hydratase gene was determined using a DNA sequencer. Then, it was confirmed that the transformant (100) had sequences according to the purpose in which mutation of 13th Ile in the α-subunit with Leu, mutation of 206th Pro in the β-subunit with Leu and mutation of 226th Val in the β-subunit with Ile were newly added to the plasmid (82) of Reference Example 36. In the production of an amide compound using the thus obtained transformant (100) and the transformant (82) to be its base, the initial reaction rate and thermal stability were compared in the same manner as in Example 1.

As a result, it was found that mutation of 13th Ile in the α-subunit with Leu, mutation of 206th Pro in the β-subunit with Leu and mutation of 226th Val in the β-subunit with Ile were newly added to the transformant (100), so that the initial reaction rate was improved by 1.72 times and thermal stability was improved by 1.42 times, as compared to those of the transformant (82).

Example 58

Construction of a Transformant (101) Substituted Amino Acid Having Improved Nitrile Hydratase Activity and Improved Thermal Stability In order to obtain a transformant (101) expressing the nitrile hydratase variant obtained by mutating nitrile hydratase at (r) and (bh) amino acid substitution sites as shown in Table 38, the plasmid (4) recovered from the transformant (4) described in the above Reference Example 3 was used as the template, and the primers having the sequence defined in SEQ ID Nos: 43, 59 and 38 in the Sequence Listing were used for repeatedly carrying out the method described in Reference Example 2 per mutation point, whereby a plasmid (101) encoding the above nitrile hydratase variant was prepared. A competent cell of Escherichia coli HB101 (manufactured by Toyobo Co., Ltd.) was transformed with the plasmid to obtain a transformant (101). Moreover, the plasmid was prepared from the above-mentioned microbial cells by the alkaline SDS extraction method, and the base sequence of the nitrile hydratase gene was determined using a DNA sequencer. Then, it was confirmed that the transformant (101) had sequences according to the purpose in which mutation of 13th Ile in the α-subunit with Leu, mutation of 206th Pro in the β-subunit with Leu and mutation of 226th Val in the β-subunit with Ile were newly added to the plasmid (4) of Reference Example 3. In the production of an amide compound using the thus obtained transformant (101) and the transformant (4) to be its base, the initial reaction rate and thermal stability were compared in the same manner as in Example 1.

As a result, it was found that mutation of 13th Ile in the α-subunit with Leu, mutation of 206th Pro in the β-subunit with Leu and mutation of 226th Val in the β-subunit with Ile were newly added to the transformant (101), so that the initial reaction rate was improved by 1.65 times and thermal stability was improved by 1.29 times, as compared to those of the transformant (4).

TABLE 51

(Table 38)

| Trans-formant No. | Mutated Site | Change in Amino Acid Sequence Before Substitution | Change in Amino Acid Sequence After Substitution | Change in Base Sequence Before Substitution | Change in Base Sequence After Substitution | Improvement of Reaction Rate by α-13th, β-206th and β-226th Substitution | Improvement of Thermal Stability by α-13th, β-206th and β-226th Substitution |
|---|---|---|---|---|---|---|---|
| 99 | α-13th | Ile | Leu | ATC | CTC | 1.85 times | 1.36 times |
|  | α-148th | Gly | Asp | GGC | GAC |  |  |
|  | α-204th | Val | Arg | GTC | CGC |  |  |
|  | β-206th | Pro | Leu | CCG | CTG |  |  |
|  | β-226th | Val | Ile | GTC | ATC |  |  |
| 100 | α-13th | Ile | Leu | ATC | CTC | 1.72 times | 1.42 times |
|  | β-10th | Thr | Asp | ACC | GAC |  |  |
|  | β-118th | Phe | Val | TTC | GTC |  |  |
|  | β-200th | Ala | Glu | GCC | GAG |  |  |
|  | β-206th | Pro | Leu | CCG | CTG |  |  |
|  | β-226th | Val | Ile | GTC | ATC |  |  |
| 101 | α-13th | Ile | Leu | ATC | CTC | 1.65 times | 1.29 times |
|  | β-40th | Thr | Ile | ACG | ATT |  |  |
|  | β-61st | Ala | Val | GCC | GTC |  |  |
|  | β-206th | Pro | Leu | CCG | CTG |  |  |
|  | β-226th | Val | Ile | GTC | ATC |  |  |

Reference Example 41

Construction of a Transformant (102) Substituted Amino Acid Having Nitrile Hydratase Activity In order to obtain a transformant (102) expressing the nitrile hydratase variant obtained by mutating nitrile hydratase at (ac) amino acid substitution sites as shown in Table 39, the plasma described in Example 60 of Patent Document 2 was used as the template, and the ribosome binding sequence was modified according to the method described in Example 1 to prepare a plasmid (102) encoding the above nitrile hydratase variant. A competent cell of Escherichia coli HB101 (manufactured by Toyobo Co., Ltd.) was transformed with the plasmid to obtain a transformant (102).

TABLE 52

(Table 39)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 102 | β-51st | Phe | Val | TTC | GTC |
| | β-108th | Glu | Asp | GAG | GAT |

Example 59

Construction of a Transformant (103) Substituted Amino Acid Having Improved Nitrile Hydratase Activity and Improved Thermal Stability In order to obtain a transformant (103) expressing the nitrile hydratase variant obtained by mutating nitrile hydratase at (s) and (ab) amino acid substitution sites as shown in Table 40, the plasmid (98) recovered from the transformant (98) described in the above Reference Example 40 was used as the template, and the primers having the sequence defined in SEQ ID Nos: 16, 29 and 59 in the Sequence Listing were used for repeatedly carrying out the method described in Reference Example 2 per mutation point, whereby a plasmid (103) encoding the above nitrile hydratase variant was prepared. A competent cell of Escherichia coli HB101 (manufactured by Toyobo Co., Ltd.) was transformed with the plasmid to obtain a transformant (103). Moreover, the plasmid was prepared from the above-mentioned microbial cells by the alkaline SDS extraction method, and the base sequence of the nitrile hydratase gene was determined using a DNA sequencer. Then, it was confirmed that the transformant (103) had sequences according to the purpose in which mutation of 92nd Asp in the α-subunit with Glu, mutation of 4th Val in the β-subunit with Met and mutation of 206th Pro in the β-subunit with Leu were newly added to the plasmid (98) of Reference Example 40. In the production of an amide compound using the thus obtained transformant (103) and the transformant (98) to be its base, the initial reaction rate and thermal stability were compared in the same manner as in Example 1.

As a result, it was found that mutation of 92nd Asp in the α-subunit with Glu, mutation of 4th Val in the β-subunit with Met and mutation of 206th Pro in the β-subunit with Leu were newly added to the transformant (103), so that the initial reaction rate was improved by 2.50 times and thermal stability was improved by 1.57 times, as compared to those of the transformant (98).

Example 60

Construction of a Transformant (104) Substituted Amino Acid Having Improved Nitrile Hydratase Activity and Improved Thermal Stability In order to obtain a transformant (104) expressing the nitrile hydratase variant obtained by mutating nitrile hydratase at (s) and (ah) amino acid substitution sites as shown in Table 40, the plasmid (37) recovered from the transformant (37) described in the above Reference Example 18 was used as the template, and the primers having the sequence defined in SEQ ID Nos: 16, 29 and 59 in the Sequence Listing were used for repeatedly carrying out the method described in Reference Example 2 per mutation point, whereby a plasmid (104) encoding the above nitrile hydratase variant was prepared. A competent cell of Escherichia coli HB101 (manufactured by Toyobo Co., Ltd.) was transformed with the plasmid to obtain a transformant (104). Moreover, the plasmid was prepared from the above-mentioned microbial cells by the alkaline SDS extraction method, and the base sequence of the nitrile hydratase gene was determined using a DNA sequencer. Then, it was confirmed that the transformant (104) had sequences according to the purpose in which mutation of 92nd Asp in the α-subunit with Glu, mutation of 4th Val in the β-subunit with Met and mutation of 206th Pro in the β-subunit with Leu were newly added to the plasmid (37) of Reference Example 18. In the production of an amide compound using the thus obtained transformant (104) and the transformant (37) to be its base, the initial reaction rate and thermal stability were compared in the same manner as in Example 1.

As a result, it was found that mutation of 92nd Asp in the α-subunit with Glu, mutation of 4th Val in the β-subunit with Met and mutation of 206th Pro in the β-subunit with Leu were newly added to the transformant (104), so that the initial reaction rate was improved by 1.82 times and thermal stability was improved by 1.41 times, as compared to those of the transformant (37).

Example 61

Construction of a Transformant (105) Substituted Amino Acid Having Improved Nitrile Hydratase Activity and Improved Thermal Stability In order to obtain a transformant (105) expressing the nitrile hydratase variant obtained by mutating nitrile hydratase at (s) and (ac) amino acid substitution sites as shown in Table 40, the plasmid (102) recovered from the transformant (102) described in the above Reference Example 41 was used as the template, and the primers having the sequence defined in SEQ ID Nos: 16, 29 and 59 in the Sequence Listing were used for repeatedly carrying out the method described in Reference Example 2 per mutation point, whereby a plasmid (105) encoding the above nitrile hydratase variant was prepared. A competent cell of *Escherichia coli* HB101 (manufactured by Toyobo Co., Ltd.) was transformed with the plasmid to obtain a transformant (105). Moreover, the plasmid was prepared from the above-mentioned microbial cells by the alkaline SDS extraction method, and the base sequence of the nitrile hydratase gene was determined using a DNA sequencer. Then, it was confirmed that the transformant (105) had sequences according to the purpose in which mutation of 92nd Asp in the α-subunit with Glu, mutation of 4th Val in the β-subunit with Met and mutation of 206th Pro in the β-subunit with Leu were newly added to the plasmid (102) of Reference Example 41. In the production of an amide compound using the thus obtained transformant (105) and the transformant (102) to be its base, the initial reaction rate and thermal stability were compared in the same manner as in Example 1.

As a result, it was found that mutation of 92nd Asp in the α-subunit with Glu, mutation of 4th Val in the β-subunit with Met and mutation of 206th Pro in the β-subunit with Leu were newly added to the transformant (105), so that the initial reaction rate was improved by 1.67 times and thermal stability was improved by 1.61 times, as compared to those of the transformant (102).

TABLE 53

(Table 40)

| Transformant No. | Mutated Site | Change in Amino Acid Sequence | | Change in Base Sequence | | Improvement of Reaction Rate by α-92nd, β-4th and β-206th Substitution | Improvement of Thermal Stability by α-92nd, β-4th and β-206th Substitution |
|---|---|---|---|---|---|---|---|
| | | Before Substitution | After Substitution | Before Substitution | After Substitution | | |
| 103 | α-92nd | Asp | Glu | GAC | GAG | 2.50 times | 1.57 times |
| | α-148th | Gly | Asp | GGC | GAC | | |
| | α-204th | Val | Arg | GTC | CGC | | |
| | β-4th | Val | Met | GTG | ATG | | |
| | β-206th | Pro | Leu | CCG | CTG | | |
| 104 | α-36th | Thr | Met | ACG | ATG | 1.82 times | 1.41 times |
| | α-92nd | Asp | Glu | GAC | GAG | | |
| | α-148th | Gly | Asp | GGC | GAC | | |
| | α-204th | Val | Arg | GTC | CGC | | |
| | β-4th | Val | Met | GTG | ATG | | |
| | β-206th | Pro | Leu | CCG | CTG | | |
| 105 | α-92nd | Asp | Glu | GAC | GAG | 1.67 times | 1.61 times |
| | β-4th | Val | Met | GTG | ATG | | |
| | β-51st | Phe | Val | TTC | GTC | | |
| | β-108th | Glu | Asp | GAG | GAT | | |
| | β-206th | Pro | Leu | CCG | CTG | | |

Reference Example 42

Construction of a Transformant (106) Substituted Amino Acid Having Nitrile Hydratase Activity In order to obtain a transformant (106) expressing the nitrile hydratase variant obtained by mutating nitrile hydratase at (az) amino acid substitution sites as shown in Table 41, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 65 and 53 in the Sequence Listing were used for repeatedly carrying out the method described in Reference Example 2 per mutation point, whereby a plasmid (106) encoding the above nitrile hydratase variant was prepared. A competent cell of *Escherichia coli* HB101 (manufactured by Toyobo Co., Ltd.) was transformed with the plasmid to obtain a transformant (106).

TABLE 54

(Table 41)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 106 | α-48th | Asn | Glu | AAC | GAA |
| | α-146th | Arg | Gly | CGG | GGG |

Example 62

Construction of a Transformant (107) Substituted Amino Acid Having Improved Nitrile Hydratase Activity and Improved Thermal Stability In order to obtain a transformant (107) expressing the nitrile hydratase variant obtained by mutating nitrile hydratase at (t) and (ac) amino acid substitution sites as shown in Table 42, the plasmid (102) recovered from the transformant (102) described in the above Reference Example 41 was used as the template, and the primers having the sequence defined in SEQ ID Nos: 24, 37 and 60 in the Sequence Listing were used for repeatedly carrying out the method described in Reference Example 2 per mutation point, whereby a plasmid (107) encoding the above nitrile hydratase variant was prepared. A competent cell of *Escherichia coli* HB101 (manufactured by Toyobo Co., Ltd.) was transformed with the plasmid to obtain a transformant (107). Moreover, the plasmid was prepared from the above-mentioned microbial cells by the alkaline SDS extraction method, and the base sequence of the nitrile hydratase gene was determined using a DNA sequencer. Then, it was confirmed that the transformant (107) had sequences according to the purpose in which mutation of 197th Gly in the α-subunit with Cys, mutation of 107th Pro in the β-subunit with Met and mutation of 230th Ala in the β-subunit with Glu were newly added to the plasmid (102) of Reference Example 41. In the production of an amide compound using the thus obtained transformant (107) and the transformant (102) to be its base, the initial reaction rate and thermal stability were compared in the same manner as in Example 1.

As a result, it was found that mutation of 197th Gly in the α-subunit with Cys, mutation of 107th Pro in the β-subunit with Met and mutation of 230th Ala in the β-subunit with Glu were newly added to the transformant (107), so that the initial reaction rate was improved by 2.11 times and thermal stability was improved by 1.88 times, as compared to those of the transformant (102).

Example 63

Construction of a Transformant (108) Substituted Amino Acid Having Improved Nitrile Hydratase Activity and Improved Thermal Stability In order to obtain a transformant (108) expressing the nitrile hydratase variant obtained by mutating nitrile hydratase at (t) and (al) amino acid substitution sites as shown in Table 42, the plasmid (70) recovered from the transformant (70) described in the above Reference Example 30 was used as the template, and the primers having the sequence defined in SEQ ID Nos: 24, 37 and 60 in the Sequence Listing were used for repeatedly carrying out the method described in Reference Example 2 per mutation point, whereby a plasmid (108) encoding the above nitrile hydratase variant was prepared. A competent cell of *Escherichia coli* HB101 (manufactured by Toyobo Co., Ltd.) was transformed with the plasmid to obtain a transformant (108). Moreover, the plasmid was prepared from the above-mentioned microbial cells by the alkaline SDS extraction method, and the base sequence of the nitrile hydratase gene was determined using a DNA sequencer. Then, it was confirmed that the transformant (108) had sequences according to the purpose in which mutation of 197th Gly in the α-subunit with Cys, mutation of 107th Pro in the β-subunit with Met and mutation of 230th Ala in the β-subunit with Glu were newly added to the plasmid (70) of Reference Example 30. In the production of an amide compound using the thus obtained transformant (108) and the transformant (70) to be its base, the initial reaction rate and thermal stability were compared in the same manner as in Example 1.

As a result, it was found that mutation of 197th Gly in the α-subunit with Cys, mutation of 107th Pro in the β-subunit with Met and mutation of 230th Ala in the β-subunit with Glu were newly added to the transformant (108), so that the initial reaction rate was improved by 1.98 times and thermal stability was improved by 2.34 times, as compared to those of the transformant (70).

Example 64

Construction (109) of a Transformant (109) Substituted Amino Acid Having Improved Nitrile Hydratase Activity and Improved Thermal Stability In order to obtain a transformant (109) expressing the nitrile hydratase variant obtained by mutating nitrile hydratase at (t) and (az) amino acid substitution sites as shown in Table 42, the plasmid (106) recovered from the transformant (106) described in the above Reference Example 42 was used as the template, and the primers having the sequence defined in SEQ ID Nos: 24, 37 and 60 in the Sequence Listing were used for repeatedly carrying out the method described in Reference Example 2 per mutation point, whereby a plasmid (109) encoding the above nitrile hydratase variant was prepared. A competent cell of *Escherichia coli* HB101 (manufactured by Toyobo Co., Ltd.) was transformed with the plasmid to obtain a transformant (109). Moreover, the plasmid was prepared from the above-mentioned microbial cells by the alkaline SDS extraction method, and the base sequence of the nitrile hydratase gene was determined using a DNA sequencer. Then, it was confirmed that the transformant (109) had sequences according to the purpose in which mutation of 197th Gly in the α-subunit with Cys, mutation of 107th Pro in the β-subunit with Met and mutation of 230th Ala in the β-subunit with Glu were newly added to the plasmid (106) of Reference Example 43. In the production of an amide compound using the thus obtained transformant (109) and the transformant (106) to be its base, the initial reaction rate and thermal stability were compared in the same manner as in Example 1.

As a result, it was found that mutation of 197th Gly in the α-subunit with Cys, mutation of 107th Pro in the β-subunit with Met and mutation of 230th Ala in the β-subunit with Glu were newly added to the transformant (109), so that the initial reaction rate was improved by 2.05 times and thermal stability was improved by 1.62 times, as compared to those of the transformant (106).

TABLE 55

(Table 42)

| Transformant No. | Mutated Site | Change in Amino Acid Sequence | | Change in Base Sequence | | Improvement of Reaction Rate by α-197th, β-107th and β-230th Substitution | Improvement of Thermal Stability by α-197th, β-107th and β-230th Substitution |
|---|---|---|---|---|---|---|---|
| | | Before Substitution | After Substitution | Before Substitution | After Substitution | | |
| 107 | α-197th | Gly | Cys | GGC | TGC | 2.11 times | 1.88 times |
| | β-51st | Phe | Val | TTC | GTC | | |
| | β-107th | Pro | Met | CCC | ATG | | |
| | β-108th | Glu | Asp | GAG | GAT | | |
| | β-230th | Ala | Glu | GCG | GAG | | |
| 108 | α-197th | Gly | Cys | GGC | TGC | 1.98 times | 2.34 times |
| | β-41st | Phe | Ile | TTC | ATC | | |
| | β-51st | Phe | Val | TTC | GTC | | |
| | β-107th | Pro | Met | CCC | ATG | | |
| | β-108th | Glu | Asp | GAG | GAT | | |
| | β-230th | Ala | Glu | GCG | GAG | | |
| 109 | α-48th | Asn | Glu | AAC | GAA | 2.05 times | 1.62 times |
| | α-197th | Gly | Cys | GGC | TGC | | |
| | β-107th | Pro | Met | CCC | ATG | | |
| | β-146th | Arg | Gly | CGG | GGG | | |
| | β-230th | Ala | Glu | GCG | GAG | | |

Reference Example 43

Construction of a Transformant (110) Substituted Amino Acid Having Nitrile Hydratase Activity In order to obtain a transformant (110) expressing the nitrile hydratase variant obtained by mutating nitrile hydratase at (ba) amino acid substitution sites as shown in Table 43, introduction of site-specific mutation was performed using the mutagenesis kit described in the above Reference Example 2. The plasmid (1) expressing nitrile hydratase with the modified ribosome binding sequence described in Example 1 was used as the template, and the primers having the sequence defined in SEQ ID Nos: 66 and 67 in the Sequence Listing were used for repeatedly carrying out the method described in Reference Example 2 per mutation point, whereby a plasmid (110) encoding the above nitrile hydratase variant was prepared. A competent cell of *Escherichia coli* HB101 (manufactured by Toyobo Co., Ltd.) was transformed with the plasmid to obtain a transformant (110).

TABLE 56

(Table 43)

| Transformant No. | Mutated Site | Change in Amino Acid Sequence | | Change in Base Sequence | |
|---|---|---|---|---|---|
| | | Before Substitution | After Substitution | Before Substitution | After Substitution |
| 110 | α-36th | Thr | Trp | ACG | TGG |
| | β-176th | Tyr | Cys | TAC | TGC |

Example 65

Construction of a Transformant (111) Substituted Amino Acid Having Improved Nitrile Hydratase Activity and Improved Thermal Stability In order to obtain a transformant (111) expressing the nitrile hydratase variant obtained by mutating nitrile hydratase at (u) and (aq) amino acid substitution sites as shown in Table 44, the plasmid (38) recovered from the transformant (38) described in the above Reference Example 19 was used as the template, and the primers having the sequence defined in SEQ ID Nos: 33 and 69 in the Sequence Listing were used for repeatedly carrying out the method described in Reference Example 2 per mutation point, whereby a plasmid (111) encoding the above nitrile hydratase variant was prepared. A competent cell of *Escherichia coli* HB101 (manufactured by Toyobo Co., Ltd.) was transformed with the plasmid to obtain a transformant (111). Moreover, the plasmid was prepared from the above-mentioned microbial cells by the alkaline SDS extraction method, and the base sequence of the nitrile hydratase gene was determined using a DNA sequencer. Then, it was confirmed that the transformant (111) had sequences according to the purpose in which mutation of 79th His in the β-subunit with Asn, mutation of 230th Ala in the β-subunit with Glu and mutation of 231st Ala in the β-subunit with Val were newly added to the plasmid (38) of Reference Example 19. In the production of an amide compound using the thus obtained transformant (111) and the transformant (38) to be its base, the initial reaction rate and thermal stability were compared in the same manner as in Example 1.

As a result, it was found that mutation of 79th His in the β-subunit with Asn, mutation of 230th Ala in the β-subunit with Glu and mutation of 231st Ala in the β-subunit with Val were newly added to the transformant (111), so that the initial reaction rate was improved by 1.46 times and thermal stability was improved by 1.43 times, as compared to those of the transformant (38).

Example 66

Construction of a Transformant (112) Substituted Amino Acid Having Improved Nitrile Hydratase Activity and Improved Thermal Stability In order to obtain a transformant (112) expressing the nitrile hydratase variant obtained by mutating nitrile hydratase at (u) and (ap) amino acid substitution sites as shown in Table 44, the plasmid (9) recovered from the transformant (9) described in the above Reference Example 5 was used as the template, and the primers having the sequence defined in SEQ ID Nos: 33 and 69 in the Sequence Listing were used for repeatedly carrying out the method described in Reference Example 2 per mutation point, whereby a plasmid (112) encoding the above nitrile hydratase variant was prepared. A competent cell of *Escherichia coli* HB101 (manufactured by Toyobo Co., Ltd.) was transformed with the plasmid to obtain a transformant (112). Moreover, the plasmid was prepared from the above-mentioned microbial cells by the alkaline SDS extraction method, and the base sequence of the nitrile hydratase gene was determined using a DNA sequencer. Then, it was confirmed that the transformant (112) had sequences according to the purpose in which mutation of 79th His in the β-subunit with Asn, mutation of 230th Ala in the β-subunit with Glu and mutation of 231st Ala in the β-subunit with Val were newly added to the plasmid (9) of Reference Example 5. In the production of an amide compound using the thus obtained transformant (112) and the transformant (9) to be its base, the initial reaction rate and thermal stability were compared in the same manner as in Example 1.

As a result, it was found that mutation of 79th His in the β-subunit with Asn, mutation of 230th Ala in the β-subunit with Glu and mutation of 231st Ala in the β-subunit with Val were newly added to the transformant (112), so that the initial reaction rate was improved by 1.42 times and thermal stability was improved by 1.66 times, as compared to those of the transformant (9).

Example 67

Construction of a Transformant (113) Substituted Amino Acid Having Improved Nitrile Hydratase Activity and Improved Thermal Stability In order to obtain a transformant (113) expressing the nitrile hydratase variant obtained by mutating nitrile hydratase at (u) and (ba) amino acid substitution sites as shown in Table 44, the plasmid (110) recovered from the transformant (110) described in the above Reference Example 43 was used as the template, and the primers having the sequence defined in SEQ ID Nos: 33 and 69 in the Sequence Listing were used for repeatedly carrying out the method described in Reference Example 2 per mutation point, whereby a plasmid (113) encoding the above nitrile hydratase variant was prepared. A competent cell of *Escherichia coli* HB101 (manufactured by Toyobo Co., Ltd.) was transformed with the plasmid to obtain a transformant (113). Moreover, the plasmid was prepared from the above-mentioned microbial cells by the alkaline SDS extraction method, and the base sequence of the nitrile hydratase gene was determined using a DNA sequencer. Then, it was confirmed that the transformant (113) had sequences according to the purpose in which mutation of 79th His in the β-subunit with Asn, mutation of 230th Ala in the β-subunit with Glu and mutation of 231st Ala in the β-subunit with Val were newly added to the plasmid (110) of Reference Example 43. In the production of an amide compound using the thus obtained transformant (113) and the transformant (110) to be its base, the initial reaction rate and thermal stability were compared in the same manner as in Example 1.

As a result, it was found that mutation of 79th His in the β-subunit with Asn, mutation of 230th Ala in the β-subunit with Glu and mutation of 231st Ala in the β-subunit with Val were newly added to the transformant (113), so that the initial reaction rate was improved by 1.39 times and thermal stability was improved by 1.38 times, as compared to those of the transformant (110).

TABLE 57

(Table 44)

| Transformant No. | Mutated Site | Change in Amino Acid Sequence | | Change in Base Sequence | | Improvement of Reaction Rate by β-79th, β-230th and β-231st Substitution | Improvement of Thermal Stability by β-79th, β-230th and β-231st Substitution |
|---|---|---|---|---|---|---|---|
| | | Before Substitution | After Substitution | Before Substitution | After Substitution | | |
| 111 | α-6th | Leu | Thr | CTG | ACG | 1.46 times | 1.43 times |
| | α-19th | Ala | Val | GCG | GTG | | |
| | α-126th | Phe | Tyr | TTC | TAC | | |
| | β-48th | Leu | Val | CTG | GTG | | |
| | β-79th | His | Asn | CAC | AAC | | |
| | β-108th | Glu | Arg | GAG | CGG | | |
| | β-212th | Ser | Tyr | TCC | TAC | | |
| | β-230th | Ala | Glu | GCG | GAG | | |
| | β-231st | Ala | Val | GCC | GTC | | |
| 112 | α-6th | Leu | Thr | CTG | ACG | 1.42 times | 1.66 times |
| | α-19th | Ala | Val | GCG | GTG | | |
| | α-126th | Phe | Tyr | TTC | TAC | | |
| | β-46th | Met | Lys | ATG | AAG | | |
| | β-79th | His | Asn | CAC | AAC | | |
| | β-108th | Glu | Arg | GAG | CGG | | |
| | β-212th | Ser | Tyr | TCC | TAC | | |
| | β-230th | Ala | Glu | GCG | GAG | | |
| | β-231st | Ala | Val | GCC | GTC | | |
| 113 | α-36th | Thr | Trp | ACG | TGG | 1.39 times | 1.38 times |
| | β-79th | His | Asn | CAC | AAC | | |
| | β-176th | Tyr | Cys | TAC | TGC | | |
| | β-230th | Ala | Glu | GCG | GAG | | |
| | β-231st | Ala | Val | GCC | GTC | | |

Example 68

Construction of a Transformant (114) Substituted Amino Acid Having Improved Nitrile Hydratase Activity and Improved Thermal Stability In order to obtain a transformant (114) expressing the nitrile hydratase variant obtained by mutating nitrile hydratase at (v) and (al) amino acid substitution sites as shown in Table 45, the plasmid (70) recovered from the transformant (70) described in the above Reference Example 30 was used as the template, and the primers having the sequence defined in SEQ ID Nos: 16, 38 and 70 in the Sequence Listing were used for repeatedly carrying out the method described in Reference Example 2 per mutation point, whereby a plasmid (114) encoding the above nitrile hydratase variant was prepared. A competent cell of *Escherichia coli* HB101 (manufactured by Toyobo Co., Ltd.) was transformed with the plasmid to obtain a transformant (114). Moreover, the plasmid was prepared from the above-mentioned microbial cells by the alkaline SDS extraction method, and the base sequence of the nitrile hydratase gene was determined using a DNA sequencer. Then, it was confirmed that the transformant (114) had sequences according to the purpose in which mutation of 92nd Asp in the α-subunit with Glu, mutation of 24th Val in the β-subunit with Ile and mutation of 226th Val in the β-subunit with Ile were newly added to the plasmid (70) of Reference Example 30. In the production of an amide compound using the thus obtained transformant (114) and the transformant (70) to be its base, the initial reaction rate and thermal stability were compared in the same manner as in Example 1.

As a result, it was found that mutation of 92nd Asp in the α-subunit with Glu, mutation of 24th Val in the β-subunit with Ile and mutation of 226th Val in the β-subunit with Ile were newly added to the transformant (114), so that the initial reaction rate was improved by 2.43 times and thermal stability was improved by 1.63 times, as compared to those of the transformant (70).

Example 69

Construction of a Transformant (115) Substituted Amino Acid Having Improved Nitrile Hydratase Activity and Improved Thermal Stability In order to obtain a transformant (115) expressing the nitrile hydratase variant obtained by mutating nitrile hydratase at (w) and (al) amino acid substitution sites as shown in Table 46, the plasmid (70) recovered from the transformant (70) described in the above Reference Example 30 was used as the template, and the primers having the sequence defined in SEQ ID Nos: 24, 37, 60 and 70 in the Sequence Listing were used for repeatedly carrying out the method described in Reference Example 2 per mutation point, whereby a plasmid (115) encoding the above nitrile hydratase variant was prepared. A competent cell of *Escherichia coli* HB101 (manufactured by Toyobo Co., Ltd.) was transformed with the plasmid to obtain a transformant (115). Moreover, the plasmid was prepared from the above-mentioned microbial cells by the alkaline SDS extraction method, and the base sequence of the nitrile hydratase gene was determined using a DNA sequencer. Then, it was confirmed that the transformant (115) had sequences according to the purpose in which mutation of 197th Gly in the α-subunit with Cys, mutation of 24th Val in the β-subunit with Ile, mutation of 107th Pro in the β-subunit with Met, and mutation of 230th Ala in the β-subunit with Glu were newly added to the plasmid (70) of Reference Example 30. In the production of an amide compound using the thus obtained transformant (115) and the transformant (70) to be its base, the initial reaction rate and thermal stability were compared in the same manner as in Example 1.

As a result, it was found that mutation of 197th Gly in the α-subunit with Cys, mutation of 24th Val in the β-subunit with Ile, mutation of 107th Pro in the β-subunit with Met, and mutation of 230th Ala in the β-subunit with Glu were newly added to the transformant (115), so that the initial reaction rate was improved by 2.23 times and thermal stability was improved by 2.51 times, as compared to those of the transformant (70).

Example 70

Construction of a Transformant (116) Substituted Amino Acid Having Improved Nitrile Hydratase Activity and Improved Thermal Stability In order to obtain a transformant (116) expressing the nitrile hydratase variant obtained by mutating nitrile hydratase at (w) and (az) amino acid substitution sites as shown in Table 46, the plasmid (106) recovered from the transformant (106) described in the above Reference Example 42 was used as the template, and the primers having the sequence defined in SEQ ID Nos: 24, 37, 60 and 70 in the Sequence Listing were used for repeatedly carrying out the

TABLE 58

(Table 45)

| Transformant No. | Mutated Site | Change in Amino Acid Sequence | | Change in Base Sequence | | Improvement of Reaction Rate by α-92nd, β-24th and β-226th Substitution | Improvement of Thermal Stability by α-92nd, β-24th and β-226th Substitution |
|---|---|---|---|---|---|---|---|
| | | Before Substitution | After Substitution | Before Substitution | After Substitution | | |
| 114 | α-92nd | Asp | Glu | GAC | GAG | 2.43 times | 1.63 times |
| | β-24th | Val | Ile | GTC | ATC | | |
| | β-41st | Phe | Ile | TTC | ATC | | |
| | β-51st | Phe | Val | TTC | GTC | | |
| | β-108th | Glu | Asp | GAG | GAT | | |
| | β-226th | Val | Ile | GTC | ATC | | | method described in Reference Example 2 per mutation point, whereby a plasmid (116) encoding the above nitrile hydratase variant was prepared. A competent cell of *Escherichia coli* HB101 (manufactured by Toyobo Co., Ltd.) was transformed with the plasmid to obtain a transformant (116). Moreover, the plasmid was prepared from the above-mentioned microbial cells by the alkaline SDS extraction method, and the base sequence of the nitrile hydratase gene was determined using a DNA sequencer. Then, it was confirmed that the transformant (116) had sequences according to the purpose in which mutation of 197th Gly in the α-subunit with Cys, mutation of 24th Val in the β-subunit with Ile, mutation of 107th Pro in the β-subunit with Met, and mutation of 230th Ala in the β-subunit with Glu were newly added to the plasmid (106) of Reference Example 42. In the production of an amide compound using the thus obtained transformant (116) and the transformant (106) to be its base, the initial reaction rate and thermal stability were compared in the same manner as in Example 1.

As a result, it was found that mutation of 197th Gly in the α-subunit with Cys, mutation of 24th Val in the β-subunit with Ile, mutation of 107th Pro in the β-subunit with Met, and mutation of 230th Ala in the β-subunit with Glu were newly added to the transformant (116), so that the initial reaction rate was improved by 2.35 times and thermal stability was improved by 1.87 times, as compared to those of the transformant (106).

TABLE 59

(Table 46)

| Transformant No. | Mutated Site | Change in Amino Acid Sequence | | Change in Base Sequence | | Improvement of Reaction Rate by α-197th, β-24th, β-107th and β-230th Substitution | Improvement of Thermal Stability by α-197th, β-24th, β-107th and β-230th Substitution |
|---|---|---|---|---|---|---|---|
| | | Before Substitution | After Substitution | Before Substitution | After Substitution | | |
| 115 | α-197th | Gly | Cys | GGC | TGC | 2.23 times | 2.51 times |
| | β-24th | Val | Ile | GTC | ATC | | |
| | β-41st | Phe | Ile | TTC | ATC | | |
| | β-51st | Phe | Val | TTC | GTC | | |
| | β-107th | Pro | Met | CCC | ATG | | |
| | β-108th | Glu | Asp | GAG | GAT | | |
| | β-230th | Ala | Glu | GCG | GAG | | |
| 116 | α-48th | Asn | Glu | AAC | GAA | 2.35 times | 1.87 times |
| | α-197th | Gly | Cys | GGC | TGC | | |
| | β-24th | Val | Ile | GTC | ATC | | |
| | β-107th | Pro | Met | CCC | ATG | | |
| | β-146th | Arg | Gly | CGG | GGG | | |
| | β-230th | Ala | Glu | GCG | GAG | | |

Example 71

Construction of a Transformant (117) Substituted Amino Acid Having Improved Nitrile Hydratase Activity and Improved Thermal Stability In order to obtain a transformant (117) expressing the nitrile hydratase variant obtained by mutating nitrile hydratase at (x) and (aq) amino acid substitution sites as shown in Table 47, the plasmid (38) recovered from the transformant (38) described in the above Reference Example 19 was used as the template, and the primers having the sequence defined in SEQ ID Nos: 33, 69 and 70 in the Sequence Listing were used for repeatedly carrying out the method described in Reference Example 2 per mutation point, whereby a plasmid (117) encoding the above nitrile hydratase variant was prepared. A competent cell of *Escherichia coli* HB101 (manufactured by Toyobo Co., Ltd.) was transformed with the plasmid to obtain a transformant (117). Moreover, the plasmid was prepared from the above-mentioned microbial cells by the alkaline SDS extraction method, and the base sequence of the nitrile hydratase gene was determined using a DNA sequencer. Then, it was confirmed that the transformant (117) had sequences according to the purpose in which mutation of 24th Val in the β-subunit with Ile, mutation of 79th His in the β-subunit with Asn, mutation of 230th Ala in the β-subunit with Glu, and mutation of 231st Ala in the β-subunit with Val were newly added to the plasmid (38) of Reference Example 19. In the production of an amide compound using the thus obtained transformant (117) and the transformant (38) to be its base, the initial reaction rate and thermal stability were compared in the same manner as in Example 1.

As a result, it was found that mutation of 24th Val in the β-subunit with Ile, mutation of 79th His in the β-subunit with Asn, mutation of 230th Ala in the β-subunit with Glu, and mutation of 231st Ala in the β-subunit with Val were newly added to the transformant (117), so that the initial reaction rate was improved by 1.73 times and thermal stability was improved by 1.50 times, as compared to those of the transformant (38).

TABLE 60

(Table 47)

| Transformant No. | Mutated Site | Change in Amino Acid Sequence | | Change in Base Sequence | | Improvement of Reaction Rate by β-24th, β-79th, β-230th and β-231st Substitution | Improvement of Thermal Stability by β-24th, β-79th, β-230th and β-231st Substitution |
|---|---|---|---|---|---|---|---|
| | | Before Substitution | After Substitution | Before Substitution | After Substitution | | |
| 117 | α-6th | Leu | Thr | CTG | ACG | 1.73 times | 1.50 times |
| | α-19th | Ala | Val | GCG | GTG | | |
| | α-126th | Phe | Tyr | TTC | TAC | | |
| | β-24th | Val | Ile | GTC | ATC | | |
| | β-48th | Leu | Val | CTG | GTG | | |
| | β-79th | His | Asn | CAC | AAC | | |
| | β-108th | Glu | Arg | GAG | CGG | | |
| | β-212th | Ser | Tyr | TCC | TAC | | |
| | β-230th | Ala | Glu | GCG | GAG | | |
| | β-231st | Ala | Val | GCC | GTC | | |

The invention claimed is:

1. A recombinant nitrile hydratase variant with improved initial reaction rate and thermal stability consisting of the α-subunit defined in SEQ ID No: 1 in the Sequence Listing and the β-subunit defined in SEQ ID No: 2 in the Sequence Listing, and a Asp92Glu substitution in SEQ ID NO: 1 and no substitution in SEQ ID NO: 2.

* * * * *

SEQUENCE LISTING

<160> NUMBER OF SEQ ID NOS: 70

<210> SEQ ID NO 1
<211> LENGTH: 205
<212> TYPE: PRT
<213> ORGANISM: Pseudonocardia thermophila

<400> SEQUENCE: 1

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 2
<211> LENGTH: 233
<212> TYPE: PRT
<213> ORGANISM: Pseudonocardia thermophila

<400> SEQUENCE: 2

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu

Leu Val Asp Thr Lys Ala Ala Ala Ala
225             230

<210> SEQ ID NO 3
<211> LENGTH: 618
<212> TYPE: DNA
<213> ORGANISM: Pseudonocardia thermophila

<400> SEQUENCE: 3

| | | |
|---|---|---|
| atgaccgaga acatcctgcg caagtcggac gaggagatcc agaaggagat cacggcgcgg | 60 |
| gtcaaggccc tggagtcgat gctcatcgaa cagggcatcc tcaccacgtc gatgatcgac | 120 |
| cggatggccg agatctacga gaacgaggtc ggcccgcacc tcggcgcgaa ggtcgtcgtg | 180 |
| aaggcctgga ccgaccccga gttcaagaag cgtctgctcg ccgacggcac cgaggcctgc | 240 |
| aaggagctcg gcatcggcgg cctgcagggc gaggacatga tgtgggtgga gaacaccgac | 300 |
| gaggtccacc acgtcgtcgt gtgcacgctc tgctcctgct acccgtggcc ggtgctgggg | 360 |
| ctgccgccga actggttcaa ggagccgcag taccgctccc gcgtggtgcg tgagccccgg | 420 |
| cagctgctca aggaggagtt cggcttcgag gtcccgccga gcaaggagat caaggtctgg | 480 |
| gactccagct ccgagatgcg cttcgtcgtc ctcccgcagc gccccgcggg caccgacggg | 540 |
| tggagcgagg aggagctcgc cacccctcgtc acccgcgagt cgatgatcgg cgtcgaaccg | 600 |
| gcgaaggcgg tcgcgtga | 618 |

<210> SEQ ID NO 4
<211> LENGTH: 702
<212> TYPE: DNA
<213> ORGANISM: Pseudonocardia thermophila

<400> SEQUENCE: 4

| | | |
|---|---|---|
| atgaacggcg tgtacgacgt cggcggcacc gatgggctgg gcccgatcaa ccggcccgcg | 60 |
| gacgaaccgg tcttccgcgc cgagtgggag aaggtcgcgt tcgcgatgtt cccggcgacg | 120 |
| ttccgggccg gcttcatggg cctggacgag ttccggttcg gcatcgagca gatgaacccg | 180 |
| gccgagtacc tcgagtcgcc gtactactgg cactggatcc gcacctacat ccaccacggc | 240 |
| gtccgcaccg gcaagatcga tctcgaggag ctggagcgcc gcacgcagta ctaccgggag | 300 |
| aaccccgacg ccccgctgcc cgagcacgag cagaagccgg agttgatcga gttcgtcaac | 360 |
| caggccgtct acggcgggct gcccgcaagc cgggaggtcg accgaccgcc caagttcaag | 420 |
| gagggcgacg tggtgcggtt ctccaccgcg agcccgaagg ccacgcccg gcgcgcgcgg | 480 |
| tacgtgcgcg gcaagaccgg gacggtggtc aagcaccacg gcgcgtacat ctacccggac | 540 |
| accgccggca acggcctggg cgagtgcccc gagcacctct acaccgtccg cttcacggcc | 600 |
| caggagctgt gggggccgga agggacccg aactccagcg tctactacga ctgctgggag | 660 |
| ccctacatcg agctcgtcga cacgaaggcg gccgcggcat ga | 702 |

<210> SEQ ID NO 5
<211> LENGTH: 144
<212> TYPE: PRT
<213> ORGANISM: Pseudonocardia thermophila

<400> SEQUENCE: 5

Met Ser Ala Glu Ala Lys Val Arg Leu Lys His Cys Pro Thr Ala Glu
1               5                   10                  15

Asp Arg Ala Ala Ala Asp Ala Leu Leu Ala Gln Leu Pro Gly Gly Asp

```
            20                  25                  30
Arg Ala Leu Asp Arg Gly Phe Asp Glu Pro Trp Gln Leu Arg Ala Phe
        35                  40                  45

Ala Leu Ala Val Ala Ala Cys Arg Ala Gly Arg Phe Glu Trp Lys Gln
 50                  55                  60

Leu Gln Gln Ala Leu Ile Ser Ser Ile Gly Glu Trp Glu Arg Thr His
 65                  70                  75                  80

Asp Leu Asp Asp Pro Ser Trp Ser Tyr Tyr Glu His Phe Val Ala Ala
                85                  90                  95

Leu Glu Ser Val Leu Gly Glu Glu Gly Ile Val Glu Pro Glu Ala Leu
            100                 105                 110

Asp Glu Arg Thr Ala Glu Val Leu Ala Asn Pro Pro Asn Lys Asp His
        115                 120                 125

His Gly Pro His Leu Glu Pro Val Ala Val His Pro Ala Val Arg Ser
    130                 135                 140

<210> SEQ ID NO 6
<211> LENGTH: 435
<212> TYPE: DNA
<213> ORGANISM: Pseudonocardia thermophila

<400> SEQUENCE: 6
gtgagcgccg aggcgaaggt ccgcctgaag cactgcccca cggccgagga ccgggcggcg      60
gccgacgcgc tgctcgcgca gctgcccggc ggcgaccgcg cgctcgaccg cggcttcgac     120
gagccgtggc agctgcgggc gttcgcgctg gcggtcgcgg cgtgcagggc gggccggttc     180
gagtggaagc agctgcagca ggcgctgatc tcctcgatcg gggagtggga gcgcacccac     240
gatctcgacg atccgagctg gtcctactac gagcacttcg tcgccgcgct ggaatccgtg     300
ctcggcgagg aagggatcgt cgagccggag gcgctggacg agcgcaccgc ggaggtcttg     360
gccaacccgc cgaacaagga tcaccatgga ccgcatctgg agcccgtcgc ggtccacccg     420
gccgtgcggt cctga                                                     435

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 7
tacgaattct aaggaggtct cagcatgaac ggc                                   33

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide to act as a PCR primer

<400> SEQUENCE: 8
ctcggtcatg ccgcggccgc c                                                21

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide to act as a PCR primer
```

```
<400> SEQUENCE: 9
atcctcacct cgtcgatgat cgac                                          24

<210> SEQ ID NO 10
<211> LENGTH: 17
<212> TYPE: DNA
<213> ORGANISM: Artificial Sequence
<220> FEATURE:
<223> OTHER INFORMATION: Oligonucleotide to act as a PCR primer

<400> SEQUENCE: 10
caggaaacag ctatgac                                                  17

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide to act as a PCR primer

<400> SEQUENCE: 11
ggccagtgcc tagcttacat                                               20

<210> SEQ ID NO 12
<211> LENGTH: 17
<212> TYPE: DNA
<213> ORGANISM: Artificial Sequence
<220> FEATURE:
<223> OTHER INFORMATION: Oligonucleotide to act as a PCR primer

<400> SEQUENCE: 12
gttttcccag tcacgac                                                  17

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 13
gagaaggtcg tgttcgcgat gttc                                          24

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 14
ttcccggcga ttttccgggc cggc                                          24

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 15
atgaacccgg tcgagtacct cgag                                          24

<210> SEQ ID NO 16
<211> LENGTH: 24
```

```
<212> TYPE: DNA
<213> ORGANISM: Artificial Sequence
<220> FEATURE:
<223> OTHER INFORMATION: Oligonucleotide to act as a PCR primer

<400> SEQUENCE: 16
cagggcgagg agatgatgtg ggtg                                             24

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 17
atgaacccgg gcgagtacct cgag                                             24

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 18
ttctccacca atagcccgaa gggc                                             24

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 19
gaggacatga tgtgggtgga gaac                                             24

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 20
ttcccggcgg tgttccgggc cggc                                             24

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 21
tactacgaca tgtgggagcc ctac                                             24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 22
```
cggcgcgcgt gttacgtgcg cggc                                          24

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 23
aagaccgggg aggtggtcaa gcac                                          24

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 24
tcgatgatct gcgtcgaacc ggcg                                          24

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 25
atcctcaccg ggtcgatgat cgac                                          24

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 26
gagctcgccg gcctcgtcac ccgc                                          24

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 27
cacggcgcgg ccatctaccc ggac                                          24

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 28
gtctactacg tctgctggga gccc                                          24

<210> SEQ ID NO 29
<211> LENGTH: 24
<212> TYPE: DNA
<213> ORGANISM: Artificial Sequence

```
<220> FEATURE:
<223> OTHER INFORMATION: Oligonucleotide to act as a PCR primer

<400> SEQUENCE: 29
atgaacggca tgtacgacgt cggc                                              24

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 30
tacgacgtcg ccggcaccga tggg                                              24

<210> SEQ ID NO 31
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 31
gagaaggtca tgttcgcgat gttc                                              24

<210> SEQ ID NO 32
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 32
cacggcgcga ccatctaccc ggac                                              24

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 33
tacatccaca acggcgtccg cacc                                              24

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 34
cgccgcacgc gttactaccg ggag                                              24

<210> SEQ ID NO 35
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 35
atgaacccgt gggagtacct cgag                                              24
```

```
<210> SEQ ID NO 36
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 36
gtctactacc actgctggga gccc                                          24

<210> SEQ ID NO 37
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 37
gccccgctga tggagcacga gcag                                          24

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 38
atcgagctca tcgacacgaa ggcg                                          24

<210> SEQ ID NO 39
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 39
atgaacccgt cggagtacct cgag                                          24

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 40
cggcgcgcga tgtacgtgcg cggc                                          24

<210> SEQ ID NO 41
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 41
cacgagcagg tgccggagtt gatc                                          24

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide to act as a PCR primer
```

```
<400> SEQUENCE: 42
gtctactaca tgtgctggga gccc                                              24

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 43
gacgaggagc tccagaagga gatc                                              24

<210> SEQ ID NO 44
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 44
atcctcaccg cgtcgatgat cgac                                              24

<210> SEQ ID NO 45
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 45
atctacgagc aagaggtcgg cccg                                              24

<210> SEQ ID NO 46
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 46
ctggagtcga tcctcatcga acag                                              24

<210> SEQ ID NO 47
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 47
cacggcgcga tgatctaccc ggac                                              24

<210> SEQ ID NO 48
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 48
gtctactacg gctgctggga gccc                                              24

<210> SEQ ID NO 49
```

```
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 49
atgaacccgc tggagtacct cgag                                          24

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 50
cacgagcaga ttccggagtt gatc                                          24

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 51
atgaacccga cggagtacct cgag                                          24

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 52
tactacgact cctgggagcc ctac                                          24

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 53
gacgtggtgg ggttctccac cgcg                                          24

<210> SEQ ID NO 54
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 54
gtctactaca gctgctggga gccc                                          24

<210> SEQ ID NO 55
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 55
```

-continued ttcccggcgc tgttccgggc cggc                                           24

<210> SEQ ID NO 56
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 56
gtctactacc tctgctggga gccc                                           24

<210> SEQ ID NO 57
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 57
cccgagcaca accagaagcc ggag                                           24

<210> SEQ ID NO 58
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 58
acgaaggcgg tcgcggcatg accg                                           24

<210> SEQ ID NO 59
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 59
ctgtgggggc tggaagggga cccg                                           24

<210> SEQ ID NO 60
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 60
gacacgaagg aggccgcggc atga                                           24

<210> SEQ ID NO 61
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 61
ttctccacct cgagcccgaa gggc                                           24

<210> SEQ ID NO 62
<211> LENGTH: 24
<212> TYPE: DNA

```
<213> ORGANISM: Artificial Sequence
<220> FEATURE:
<223> OTHER INFORMATION: Oligonucleotide to act as a PCR primer

<400> SEQUENCE: 62
gtctactact gttgctggga gccc                                              24

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 63
acggtggtcg cgcaccacgg cgcg                                              24

<210> SEQ ID NO 64
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 64
gtctactaca cctgctggga gccc                                              24

<210> SEQ ID NO 65
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 65
atctacgagg aagaggtcgg cccg                                              24

<210> SEQ ID NO 66
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 66
atcctcacct ggtcgatgat cgac                                              24

<210> SEQ ID NO 67
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 67
cacggcgcgt gcatctaccc ggac                                              24

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 68
gccccgctga tggatcacga gcag                                              24
```

```
<210> SEQ ID NO 69
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 69
gacacgaagg aggcgcggca tgac                                          24

<210> SEQ ID NO 70
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 70
gacgaaccga tcttccgcgc cgag                                          24
```